US012708892B2

(12) United States Patent
Weems

(10) Patent No.: US 12,708,892 B2
(45) Date of Patent: Aug. 18, 2026

(54) SHAPE MEMORY POLY(β-HYDROXYTHIOETHER) FOAMS RAPIDLY PRODUCED FROM MULTIFUNCTIONAL EPOXIDES AND THIOLS

(71) Applicant: Ohio University, Athens, OH (US)

(72) Inventor: Andrew Weems, Athens, OH (US)

(73) Assignee: Ohio University, Athens, OH (US)

( * ) Notice: Subject to any disclaimer, the term of this patent is extended or adjusted under 35 U.S.C. 154(b) by 248 days.

(21) Appl. No.: 18/262,278

(22) PCT Filed: Jan. 24, 2022

(86) PCT No.: PCT/US2022/013481
§ 371 (c)(1),
(2) Date: Jul. 20, 2023

(87) PCT Pub. No.: WO2022/159801
PCT Pub. Date: Jul. 28, 2022

(65) Prior Publication Data
US 2024/0075455 A1 Mar. 7, 2024

Related U.S. Application Data

(60) Provisional application No. 63/140,487, filed on Jan. 22, 2021.

(51) Int. Cl.
*B01J 20/22* (2006.01)
*A61L 27/18* (2006.01)
(Continued)

(52) U.S. Cl.
CPC ............. *B01J 20/264* (2013.01); *A61L 27/18* (2013.01); *C08G 83/003* (2013.01);
(Continued)

(58) Field of Classification Search
CPC .. B01J 20/264; B01J 20/262; B01J 20/28045; A61L 27/18; A61L 2400/16;
(Continued)

(56) References Cited

U.S. PATENT DOCUMENTS 10,179,831 B2 1/2019 Weippert
2003/0055198 A1 3/2003 Langer et al.
(Continued)

FOREIGN PATENT DOCUMENTS

CN 108276739 A * 7/2018 ............. C08L 35/02

OTHER PUBLICATIONS

Ellson et al., "Tunable thiol-epoxy shape memory polymer foams," Smart Materials and Structures, 24, (2015), 1-11. (Year: 2015).*
(Continued)

*Primary Examiner* — K. Boyle
(74) *Attorney, Agent, or Firm* — Wood Herron & Evans LLP

(57) ABSTRACT

A shape memory polymer foam comprising a reaction product of a reaction of an epoxide and a thiol monomer in the presence of an organobase is provided. In addition, a method of making the shape memory polymer foam is provided. The method includes reacting an epoxide with thiol monomers in the presence of an organobase to form the shape memory polymer foam.

14 Claims, 47 Drawing Sheets

(51) Int. Cl.
*B01J 20/26* (2006.01)
*C08G 83/00* (2006.01)
*C08G 101/00* (2006.01)

(52) U.S. Cl.
CPC ...... *A61L 2400/16* (2013.01); *C08G 2101/00* (2013.01); *C08G 2280/00* (2013.01)

(58) Field of Classification Search
CPC .. A61L 24/001; A61L 24/046; A61L 24/0036; C08G 83/003; C08G 2101/00; C08G 2280/00; C08G 59/686; C08G 75/04; C08G 59/66; C08G 2381/02; C08G 75/02; B01D 17/0202; C08L 81/02; C08J 2363/02; C08J 2203/12; C08J 9/142; C08J 9/0028; C08J 2207/10; C08K 3/32
See application file for complete search history.

(56) References Cited

U.S. PATENT DOCUMENTS

2017/0174823 A1* 6/2017 Weippert ........... C08G 59/4021
2020/0165490 A1 5/2020 Kryger et al.

OTHER PUBLICATIONS

Translation of CN 108276739. (Year: 2018).*
King et al., “Shape Memory Poly(β-hydroxythioether) Foams for Oil Remediation in Aquatic Environments,” Applied Materials & Interfaces, 2021, 13, 20641-20652 (Year: 2021).*
International Searching Authority, International Search Report and Written Opinion issued in corresponding PCT Application No. PCT/US2022/013481, dated May 4, 2022.
Rodriguez JN, et al., “Reticulation of low density shape memory polymer foam with an in vivo demonstration of vascuar occlusion”, Journal of the Mechanical Behavior of Biomedical Materials, Amsterdahm, NL, vol. 40, Aug. 11, 2014, pp. 102-114.
Landsman TL, et al., “A shape memory foam composite with enhanced fluid uptake and bactericidal properties as a hemostatic agent”, Acta Biomaterialia 47 (2017), pp. 91-99.

* cited by examiner

BADGE

N Epoxide

IDPI Epoxide 1. 5 min, room temp
2. 24 h, 120 °C

FIG. 1

BADGE or

Neopentyl 1. 5 min, room temp
2. 24 h, 120 C

SHAPE MEMORY POLY(β-HYDROXYTHIOETHER) FOAMS RAPIDLY PRODUCED FROM MULTIFUNCTIONAL EPOXIDES AND THIOLS

RELATED APPLICATION

This application is a National Stage Application that claims the benefit of, and priority to, International PCT Application No. PCT/US22/13481, entitled "SHAPE MEMORY POLY (β-HYDROXYTHIOETHER) FOAMS RAPIDLY PRODUCED FROM MULTIFUNCTIONAL EPOXIDES AND THIOLS" filed on Jan. 24, 2022, the disclosure of which is hereby incorporated by reference herein in its entirety. This application also claims the benefit of, and priority to, U.S. Provisional Patent Application No. 63/140,487, entitled "SHAPE MEMORY POLY (β-HYDROXYTHIOETHER) FOAMS RAPIDLY PRODUCED FROM MULTIFUNCTIONAL EPOXIDES AND THIOLS" filed on Jan. 22, 2021, the disclosure of which is hereby incorporated by reference herein in its entirety.

BACKGROUND OF THE INVENTION

Environmental remediation after oil spills is an ongoing concern, in part due to the long-lasting nature of clean-ups after catastrophes such as the British Petroleum oil spill in the Gulf of Mexico, among many other high-profile occurrences. However, despite the publicity and public outrage that has occurred after such events, there are still few viable options to allow for the salvaging or reclamation of the spilled oil and the cleaning of the local environments. In fact, the Environmental Protection Agency often is required to maintain a permanent presence after waterway spills due, at least in part, to the persistent presence of surface oil slick, even if larger oil residues have been cleaned. Just as importantly, human contact with the current cleaning methods, including dispersants, often leads to concerning long-term complications including altered blood and liver enzymes as well as concerning outcomes for various levels of life in the surrounding regions.

Shape memory polymer (SMP) foams have been touted as offering a variety of different fields access to low-density, stimuli-responsive materials capable of changing their respective industries, and may be of great interest to oil remediation strategies moving forward. Many different species of SMPs have been developed and examined as porous media, including polyurethanes, polyureas, polyesters, polyethers (derived from epoxides as well as those from other sources), polyamides, polycarbonates, and many others. Foams have been produced from many of these materials, with a huge range of morphologies, pore/cell sizes, strut thicknesses and geometries, densities, and physical properties. However, in fields such as biomedical engineering, these materials have been limited by their final material properties compared with the design criteria of the application. For example, aromatic polyurethanes have been linked with hydrolytic degradation in instances where biostability is required (breast implant coatings). Conversely, certain species of aliphatic polyurethanes have been linked with oxidative degradation, which may limit their translational potential. Additionally, polyurethane foams, among others, often rely on a two-step synthetic approach, where the pre-polymer step may require as long as 48 h before the foaming may proceed, after which additional thermal treatments and post processing is needed, making the process a week or more from start to finish, a distinct disadvantage for many applications.

Epoxy-thiol resins have seen use in a variety of different uses, ranging from biomedical devices to aerospace, adhesives, and coatings. Traditional epoxy resins typically make use of amine hardeners or utilize other nucleophiles to facilitate rapid ring opening of the epoxides. The use of thiols has been more recently explored as part of the thiol-epoxy "click" reaction, which has been explored for a range of applications including self-assembly reactions, thermoset resins, and even vitrimer materials. In particular, the use of difunctional epoxide monomers has been explored for these purposes, with commodity materials providing a wide array of possible combinations for production of polymers, including bisphenol A derivatives. Importantly, this reaction has been utilized to yield materials within hours of mixing the components, which, while still too slow for conventional foaming, has been utilized to produce porous scaffolds through the incorporation of different particulates and salts.

As discussed herein, thiol-epoxy "click" reactions are performed using different epoxides in conjunction with a multifunctional, commercially available Pentaerythritoltetra (3-mercaptopropionate) (PETMP) in the presence of the super organobase DBU. Rheology, spectroscopy, and physical experimentation are used to demonstrate rapid foam blowing within seconds of mixing the reactants. The resulting materials are characterized for thermomechanical behaviors, degradability, shape memory properties, and even potential for scavenging oil in aquatic environments through the use of a model study. These materials, and their post-foaming functionalized equivalents, demonstrated potential for environmental remediation, biomedical engineering applications, and beyond.

Furthermore, porous media is used in a variety of applications including environmental remediation and medicine. Recently, porous tissue scaffolds have grown to become one of the most important types of implantable material classes in clinical use. In general, porosity allows for cellular infiltration that leads to healing, while simultaneously allowing for the diffusion of waste and nutrients needed to promote vascularization and healing. Compared with non-porous implants, the biological response to such materials is moderated with improved healing rates, reduced fibrous capsule formation, and a reduced inflammatory load at the implant site. Simply by introducing or tailoring pores in foams, the biocompatibility of materials may be enhanced.

Previous work with polymer foam biomaterials has focused on polyurethanes (PUs), polyethers, polyesters, and polycarbonates, where PUs have perhaps been the most widely utilized clinically. PUs have been proposed for applications ranging from aneurysm occlusive devices to breast implant coatings, one of the most well-known applications. The limitations of PUs in breast implants, and to some extent other applications, has been suspicions of toxic degradation products, namely the formation of toluene diamine during hydrolysis. While the conditions required to cleave the aromatic urethane linkages are unlikely to occur in vivo (the in vitro testing conditions utilized to achieve the oligomeric and monomeric degradation products were wildly exaggerated compared with those found in the body), the concern surrounding these products was sufficient to limit PUs foam utility in breast implant coatings to this day. This is despite the limited negative outcomes reported by patients or the adverse events reported by clinicians, and the benefits achieved by introducing porous media rather than merely texturing the implant's surface (which did not achieve nearly the same biocompatibility benefits as the foams). There is a need for alternative foam chemistries that can be utilized for soft and hard void implant devices which do not suffer from the potential to produce carcinogenic or toxic degradation products.

SUMMARY OF THE INVENTION

Poly(β-hydroxythioether) are a newer class of material suitable for foaming that have several distinct advantages compared with other biomaterials. Notably, β-hydroxythioether are synthesized as part of a thio-epoxy "click" reaction that is highly efficient, robust, bio-orthogonal, and even stereoselective in some cases. This combination of factors means that the thermoset network required for crosslinked foams, which in shape memory (4D) materials reduces the expansion force to negligible values, may form rapidly and robustly without requiring elevated temperatures or prolonged curing times, and the synthetic process does not present the same level of risk as diisocyanate exposure will to manufacturing personnel.

Here, a novel series of poly(β-hydroxythioether) foams as proposed implantable biomaterials are described. Two bifunctional epoxide monomers are used to tune the physical properties of the porous scaffolds, requiring the transition to salt-leached foaming as opposed to gas-blown foaming, and the physical and chemical properties of the resulting foams are characterized. Importantly, shape memory responsiveness, hydrolytic stability, and cytocompatibility are demonstrated, being important criteria for clinical translational potential.

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

To address the aforementioned issues, in an embodiment of the present invention a shape memory polymer foam is provided. The shape memory polymer foam is formed of a reaction product of a reaction of an epoxide and a thiol monomer in the presence of an organobase.

In another embodiment of the invention, a method of making a shape memory polymer foam is provided. The method includes reacting an epoxide with a thiol monomer in the presence of an organobase to form the shape memory polymer foam.

In another embodiment of the invention, a method of medically treating a patient with a shape memory polymer foam is provided. The method includes administering an amount of shape memory polymer foam into the patient's bloodstream and stabilizing the patient's blood flow.

In another embodiment of the invention, a method of reclaiming crude oil is provided. The method includes administering a shape memory polymer foam to absorb an amount of crude oil. The method further includes collecting the shape memory polymer foam with the absorbed crude oil. The method further includes treating the shape memory polymer foam to collect the absorbed crude oil.

In another embodiment of the invention, a method of making a shape memory polymer foam is provided. The method includes reacting an epoxide with a thiol monomer in the presence of an organobase, a salt, and acetone to form a shape memory polymer foam-salt composite. The method further includes removing at least a portion of the salt from the shape memory the shape memory polymer foam-salt composite to form the shape memory polymer foam.

In another embodiment of the invention, a method of making a shape memory polymer foam is provided. The method includes reacting pentaerythritoltetra(3-mercaptopropionate) and bisphenol A diglycidyl ether in the presence of 1,8-diazabicyclo[5.4.0]undec-7-ene to form a filament. The method further includes printing the filament into a form using a 3-D printer.

BRIEF DESCRIPTION OF THE DRAWINGS

FIG. 1 shows a schematic of bisphenol A diglycidyl ether (BADGE) monomer reaction with Pentaerythritoltetra(3-mercaptopropionate) (PETMP) in the presence of 1,8-diazabicyclo[5.4.0]undec-7-ene (DBU).

FIG. 53 shows the idealized reaction scheme for thiol-epoxy "click" network formation of the β-hydroxythioethers, catalyzed by the organobase DBU, with the two diepoxides of interest.

FIG. 57 shows a graph plotting the weight percentage of a salt template in the foam being tested after 120 hours of exposure of the foam to a given temperature.

FIG. 58 shows a representative thermogravimetric analysis of a foam according to an embodiment of the invention formed using neopentyl monomer (NEO). FIG. 58 shows a graph plotting the weight percentage of a salt template in the foam being tested after 120 hours of exposure of the foam to a given temperature.

DETAILED DESCRIPTION

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Figure 1:
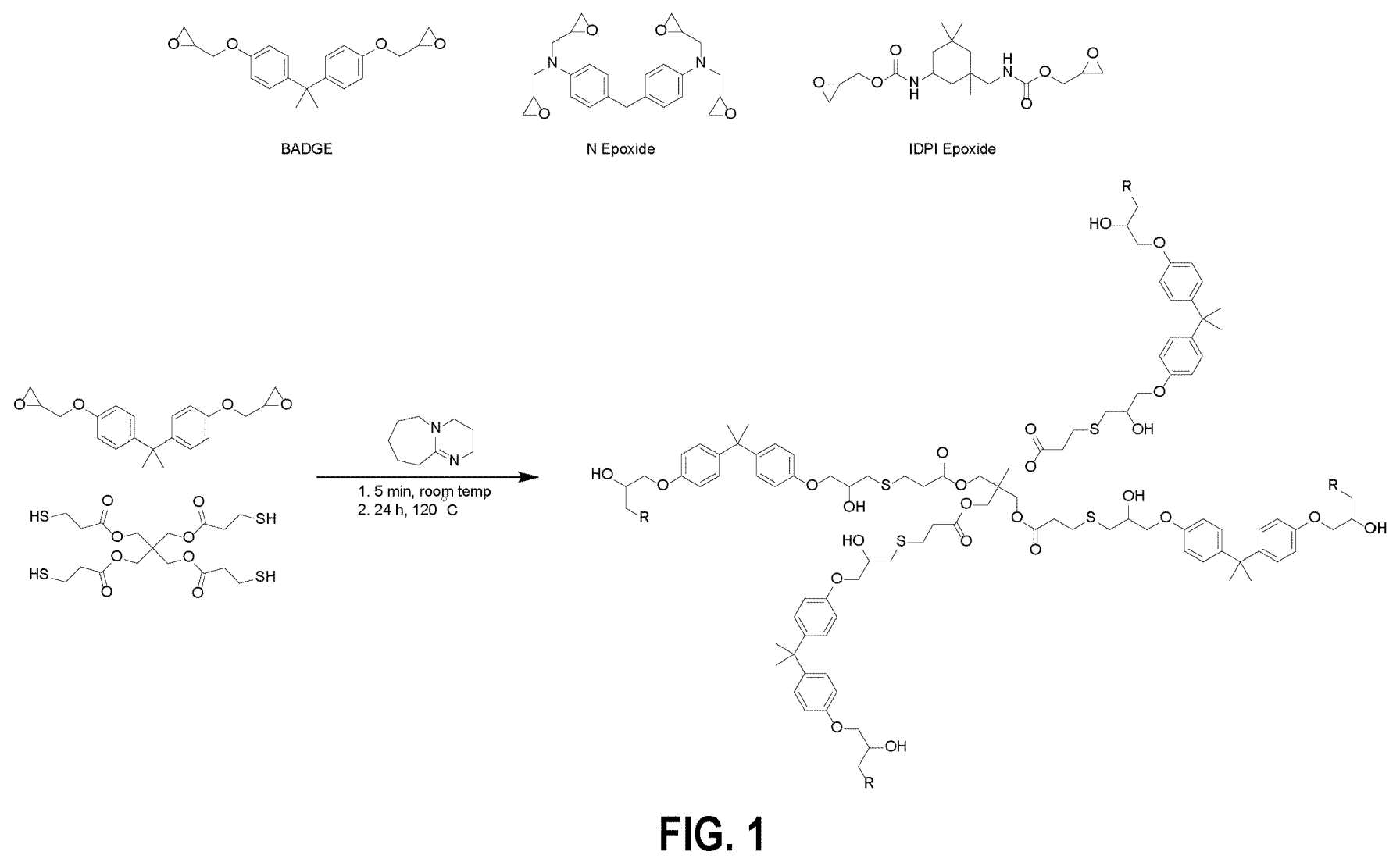

To address the aforementioned issues, aspects of the present invention include shape memory polymer (SMP) foam including a reaction product of a reaction of an epoxide and a thiol monomer in the presence of an organobase, as shown in FIG. 1. FIG. 1 shows a particular embodiment of the invention, that is, a reaction between BADGE and a thiol monomer in the presence of an organobase, shown in FIG. 1 as 1,8-Diazabicyclo[5.4.0]undec-7-ene (DBU). The reaction product according to the invention is a shape memory polymer foam, an embodiment of which is shown in FIG. 1 as a poly(β-hydroxythioether).

Figure 20:
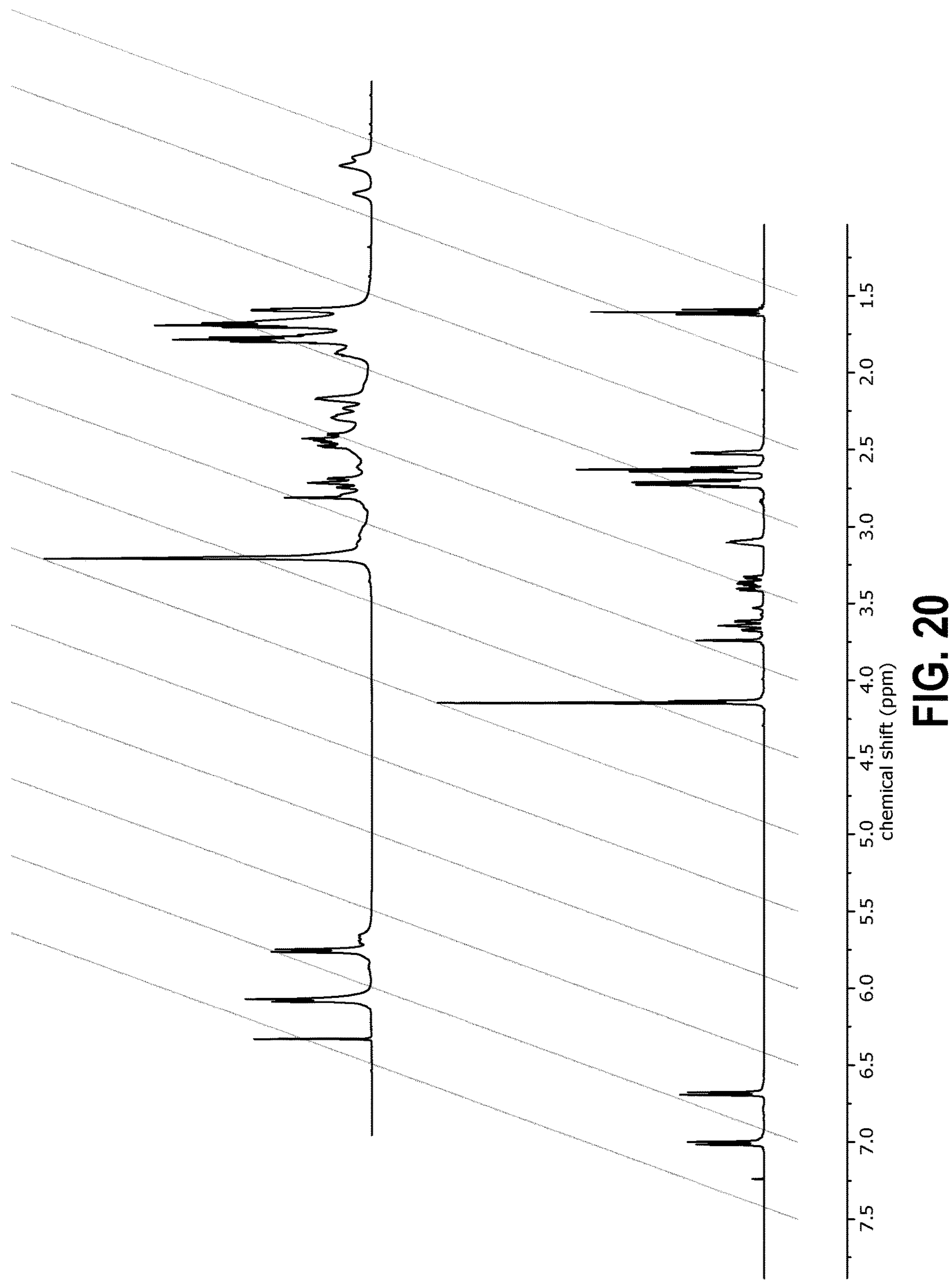
FIG. 20 shows a 1H NMR before and after comparison of N epoxide and PETMP.
Figure 21:
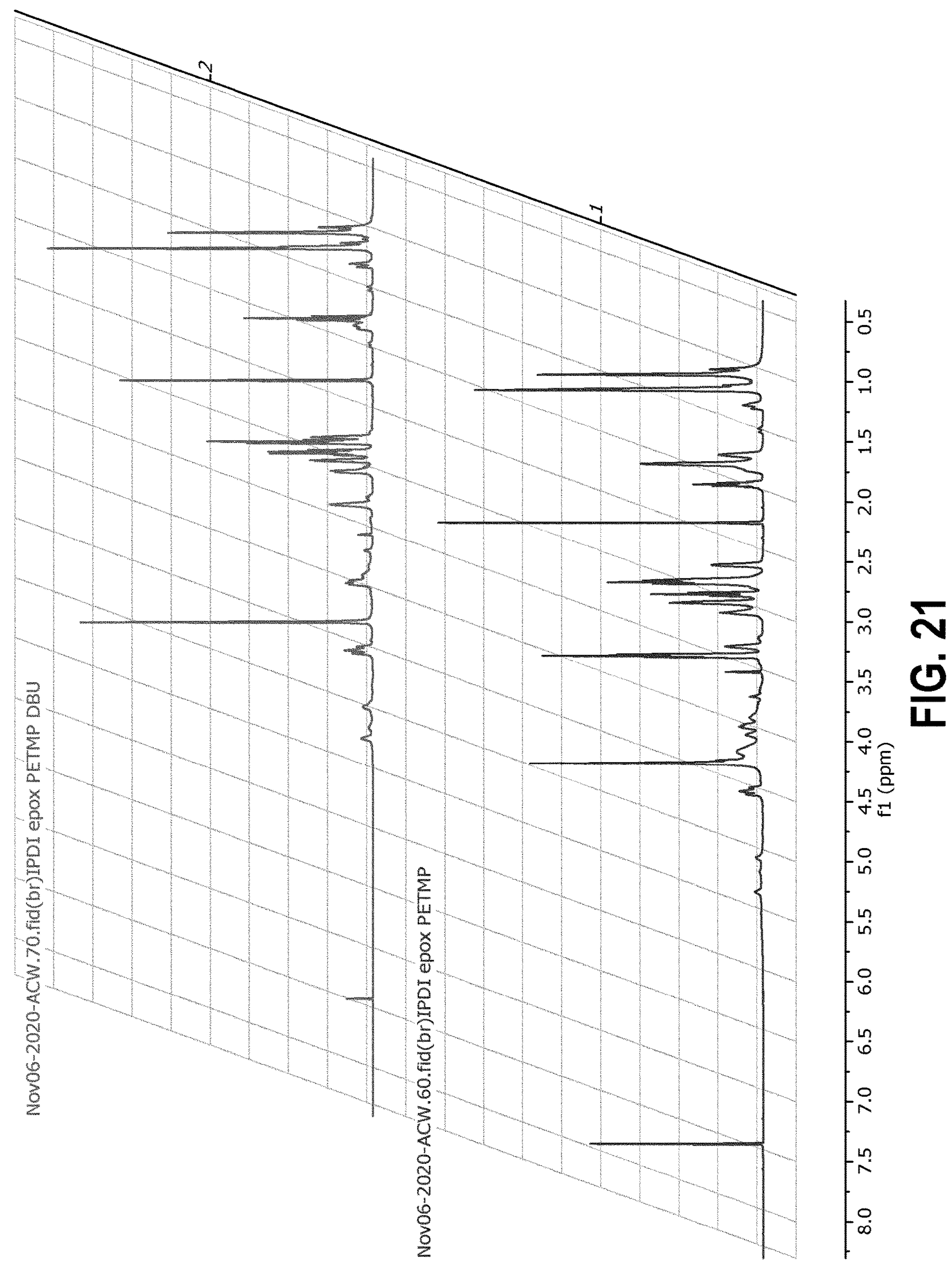
FIG. 21 shows a 1H NMR before and after comparison of IPDI epoxide and PETMP.
Figure 23:
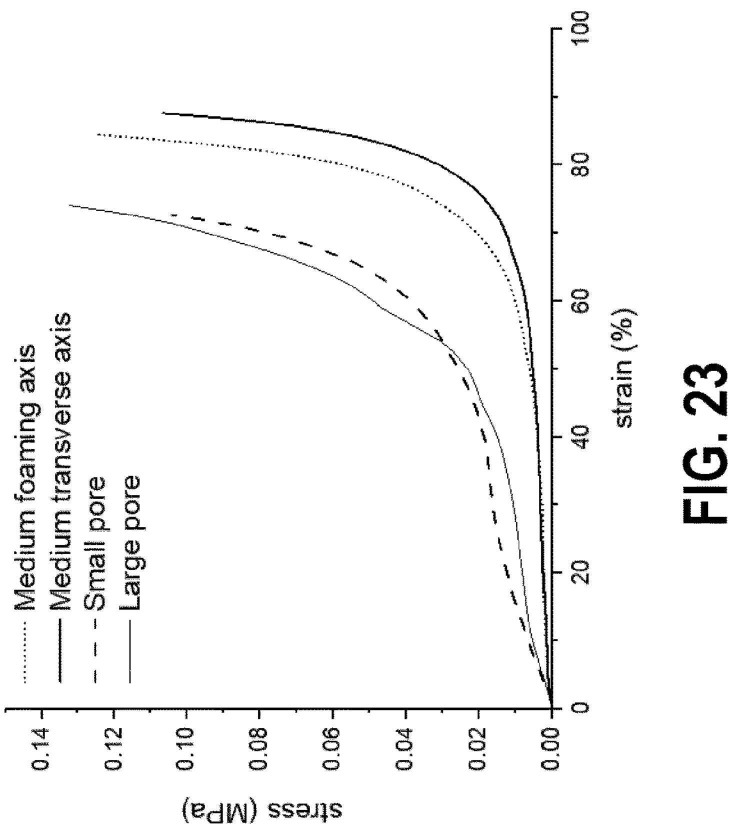
FIG. 23 shows a representative compressive stress-strain plot, compressed at 5 mm×$min^{-1}$ to yield using the DMA at room temperature and ambient atmosphere.
Figure 22:
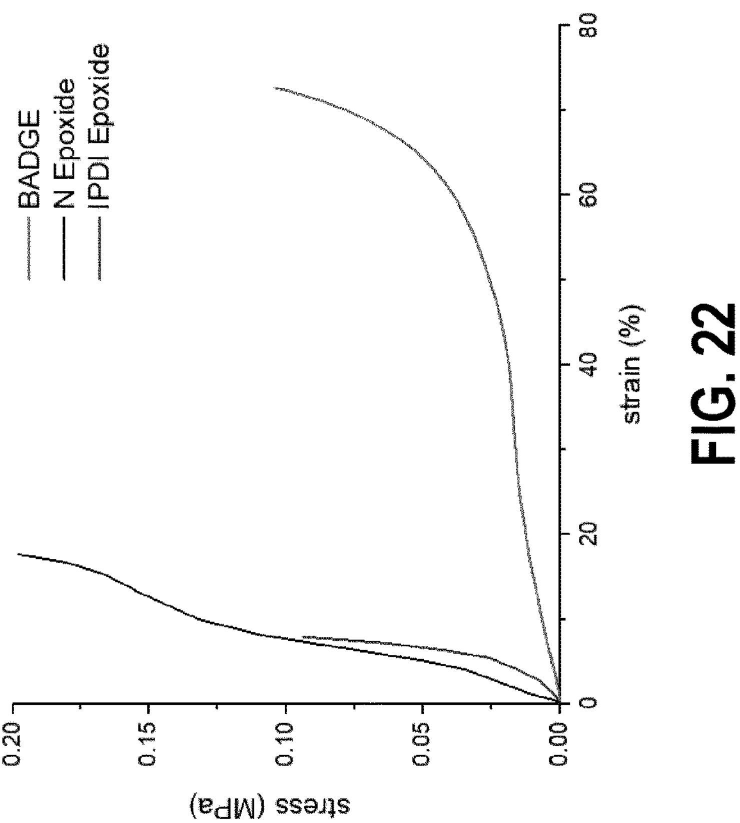
FIG. 22 shows a representative compressive stress-strain plot, compressed at 5 mm×$min^{-1}$ to yield using the DMA at room temperature and ambient atmosphere.
Figure 28:
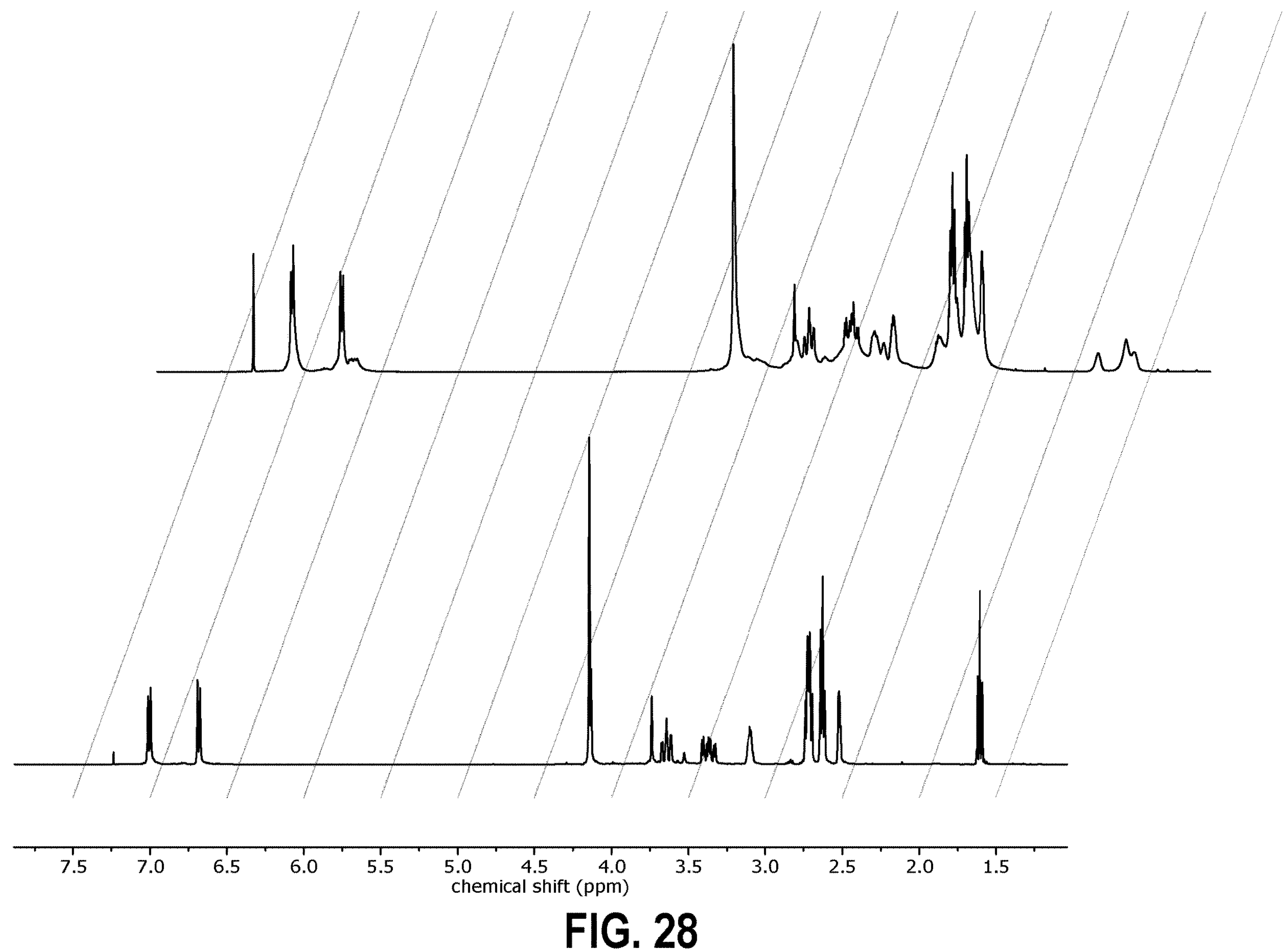
FIG. 28 shows a $^{1}H$ NMR before and after comparison of N epoxide and PETMP (300 MHz, 298 K, $CDCl_3$).
Figure 29:
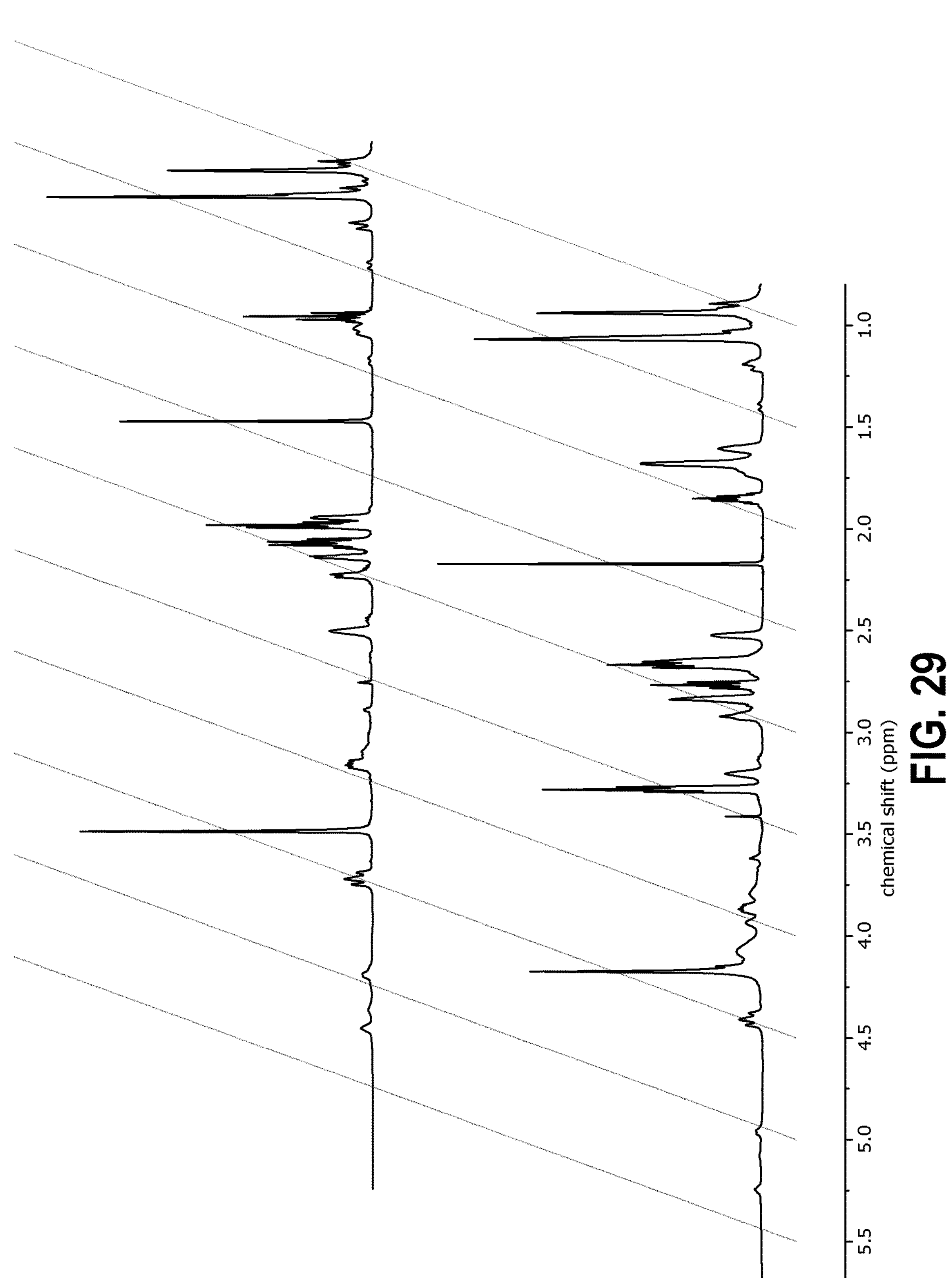
FIG. 29 show a $^{1}H$ NMR before and after comparison of IPDI epoxide and PETMP (300 MHz, 298 K, $CDCl_3$).

The epoxide used in the reaction to form the SMP foam may be any epoxide configured to form an SMP foam when reacted with a thiol monomer in the presence of an organobase catalyst. In some examples, the epoxide used in the reaction is selected from a group consisting of bisphenol A diglycidyl ether (BADGE), BADGE derivatives, neopentyl monomer (NEO), NEO derivatives, N epoxide, Isophorone di(oxiran-2-methyl carbamate) (IDPI) epoxide, IDPI epoxide derivatives, and combinations thereof. FIG. 20 shows a comparative $^1$H NMR from N epoxide to an N epoxide and PETMP-derived foam. Another comparative $^1$H NMR is shown in FIG. 28, which shows a before and after comparison of N epoxide and PETMP (300 MHz, 298 K, $CDCl_3$). FIG. 21 shows a comparative $^1$H NMR from IPDI to an IPDI and PETMP-derived foam. Another comparative $^1$H NMR is shown in FIG. 29, which shows a before and after comparison of IPDI epoxide and PETMP (300 MHz, 298 K, $CDCl_3$). Further representative compressive stress-strain plots of a variety of foams, compressed at 5 mm×min$^{-1}$ to yield using the DMA at room temperature and ambient atmosphere is shown in FIG. 22 and FIG. 23.

The thiol monomer used in the reaction to form the SMP foam may be any thiol monomer configured to form an SMP foam when reacted with an epoxide in the presence of an organobase catalyst. In some examples, the thiol monomer used in the reaction is selected from a group consisting of pentaerythritoltetra(3-mercaptopropionate).

Stoichiometric amounts of each of the epoxide and the thiol monomer may be reacted to form the SMP foam according to an embodiment of the invention. The reaction is encouraged if performed in the presence of an organobase. The epoxide and the thiol monomer may be combined in a container, such as a beaker, in the presence of an organobase and mixed. Alternatively or in addition, the reaction may occur in the presence of acetone, which may aid in dissolving reactants and to serve as a physical blowing agent for foam creation.

In another embodiment, a method of making an SMP foam is described. The method includes reacting an epoxide with a thiol monomer in the presence of an organobase, a salt, and, optionally, acetone to form a shape memory polymer foam-salt composite. The shape memory polymer foam-salt composite may include a salt template formed from the salt used in the reaction previously described. The salt template may be removed by washing, for example by a water extraction, resulting in porous scaffolds of SMP foam. In some examples, the formed SMP foam includes β-hydroxythioether as a product of the above-described reaction.

Applications of the SMP foams described herein are myriad, with examples including cleaning environments that have been contaminated with oil, salvaging oil from environments into which oil has seeped or spilled, harvesting crude oil, or even medical applications.

At least because the SMP foams may be safe for treatment of humans, such as through implantation, in some examples, the SMP foams described herein may be used to medically treat a patient. The method may include administering an amount of the SMP foam into the patient's bloodstream followed by stabilizing the patient's blood flow. In these examples, the SMP foam may include poly(β-hydroxythioether). In some examples, the poly(β-hydroxythioether) used in the SMP foams is formed by the reactions described herein between an epoxide and one or more thiol monomers in the presence of an organobase catalyst. Specifically, in an embodiment, the SMP foam used in medically treating a patient includes a poly(β-hydroxythioether) formed from a reaction between BADGE and PETMP in the presence of an organobase such as DBU.

Alternatively or in addition, the SMP foams described herein may be used in harvesting crude oil. Such methods may include administering the SMP foam described herein to absorb an amount of crude oil, collecting the SMP foam with the absorbed crude oil included therein, and subsequently treating the SMP foam to extract the crude oil absorbed in the SMP foam. In these examples, the SMP foam may include poly(β-hydroxythioether). In some examples, the poly(β-hydroxythioether) used in the SMP foams is formed by the reactions described herein between an epoxide and one or more thiol monomers in the presence of an organobase catalyst. Specifically, in an embodiment, the SMP foam used in medically treating a patient includes a poly(β-hydroxythioether) formed from a reaction between BADGE and PETMP in the presence of an organobase such as DBU.

Alternatively or in addition, the SMP foams described herein may be used in breast implants. For example, a breast implant may include a housing and an SMP foam as described herein may be encased in the housing. At least because the SMP foams may be acceptable material for implantation into a human body, it is possible to implant the SMP foams described herein in the breast of a human.

EXAMPLES

Example 1

General: Chemicals were purchased and used without purification from VWR®, a subsidiary of Avantor®, having its corporate headquarters in Radnor, PA, USA. Spectroscopic analysis was conducted on a NMR spectra (400 MHz for $^{1}H$ and 125 MHz for $^{13}C$) were recorded on a Bruker® 400 spectrometer and processed using MestReNova® v9.0.1 (from Mestrelab® Research, having a place of business in S.L., Santiago de Compostela, Spain). Chemical shifts were referenced to residual solvent peaks at 6=7.26 ppm ($^{1}H$) and δ=77.16 ppm ($^{13}C$) for $CDCl_3$. Fourier transform infrared spectroscopy (FT-IR) was performed in attenuated total reflectance (ATR) mode on a Bruker® infrared spectrometer (Bruker®, having a place of business in Billerica, MA, USA) using 50 scans with background subtraction and a resolution of 2 $cm^{1}$. Rheology was conducted on a TA Instruments DH3® rheometer (TA Instruments Inc®, having a place of business in Delaware, USA) fitted with a Peltier parallel plate system (40 mm stainless steel plate with 0° surface, TA Instruments®, having a place of business in New Castle, Delaware, USA) and adjusted to a gap of 500 μm for all studies. Dynamic mechanical analysis (DMA) was conducted using a TA Instruments® DMA 800 (TA Instruments Inc®, having a place of business in Delaware, USA).

Synthesis of Isophorone di(oxiran-2-methyl carbamate) (IPDI Epaxide)

Figure 19:
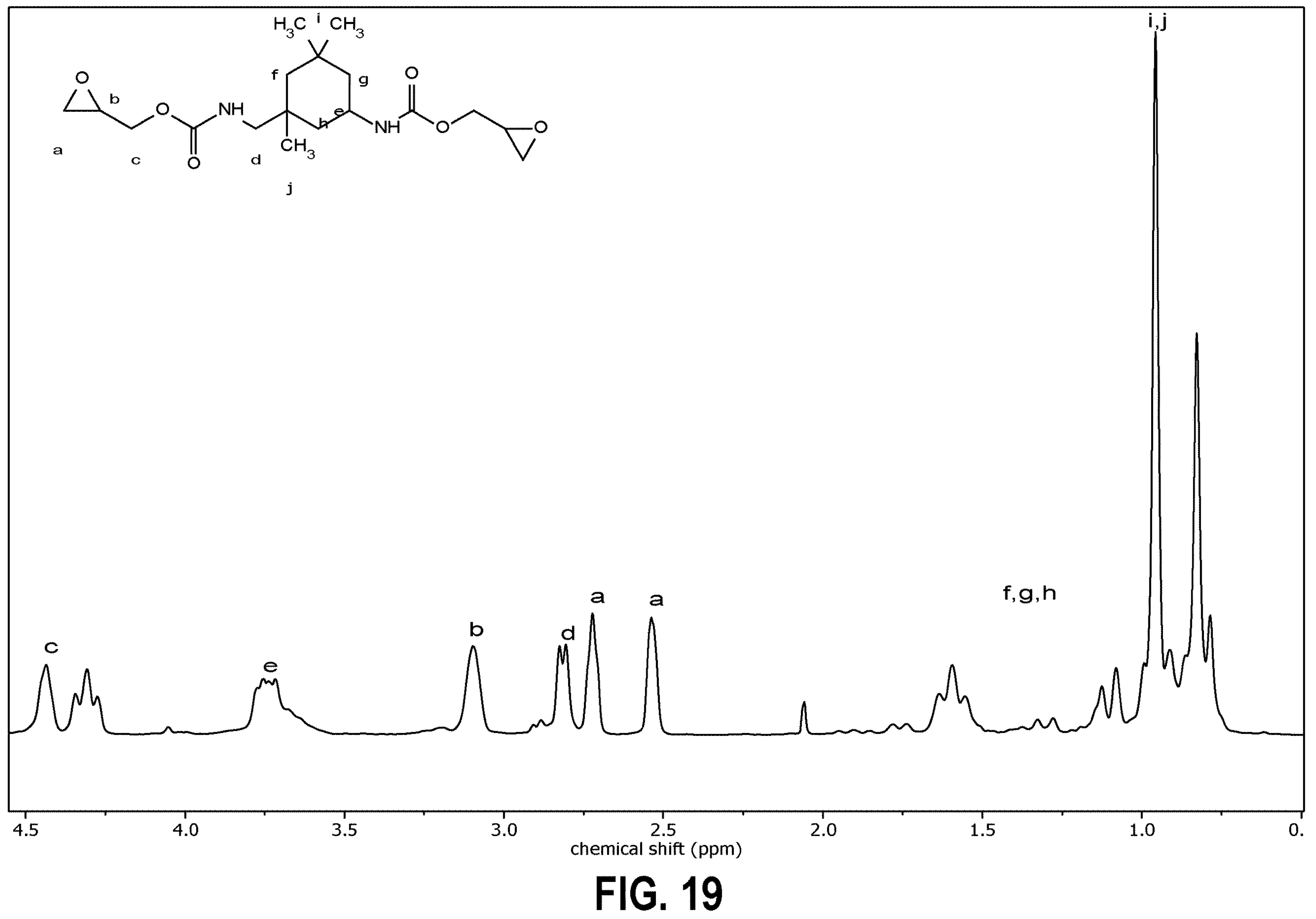
FIG. 19 shows a 300 MHz $^{1}H$ NMR of IPDI Epoxide monomer (298 K, $CDCl_3$).
Figure 26:
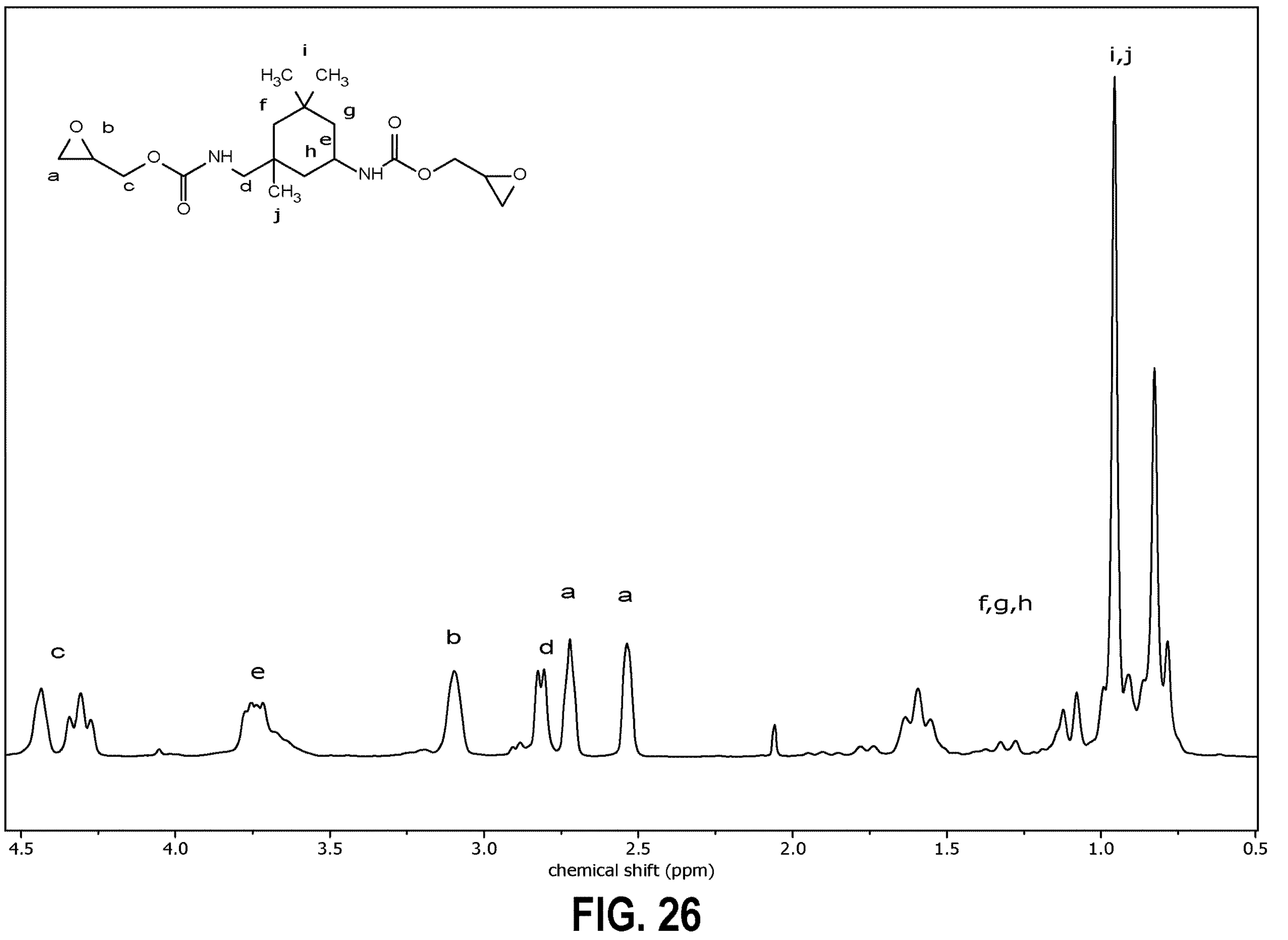
FIG. 26 shows a 300 MHz $^{1}H$ NMR of IPDI Epoxide monomer (298 K, $CDCl_3$).

Isophorone diisocyanate (IPDI) was added to a round bottom flask equipped with a stir bar, along with a stoichiometric amount of glycidol and 20 mL of dry acetone. The reaction vessel was sealed and heated to 50° C. for 24 h, over which time the viscosity of the mixture dramatically increased until the stir bar could no longer move. The crude product was taken up in ethyl acetate after removing residual acetone, and washed once with 0.1 M HCl and once with brine. The collected product was a clear high viscosity liquid at room temperature (Yield=81%) ESI MS: 370.45 (theoretical), 388.48 (mass+$NH_4$) $^{1}H$ NMR (CDCl3): (FIGS. 19 and 26).

Figure 27:
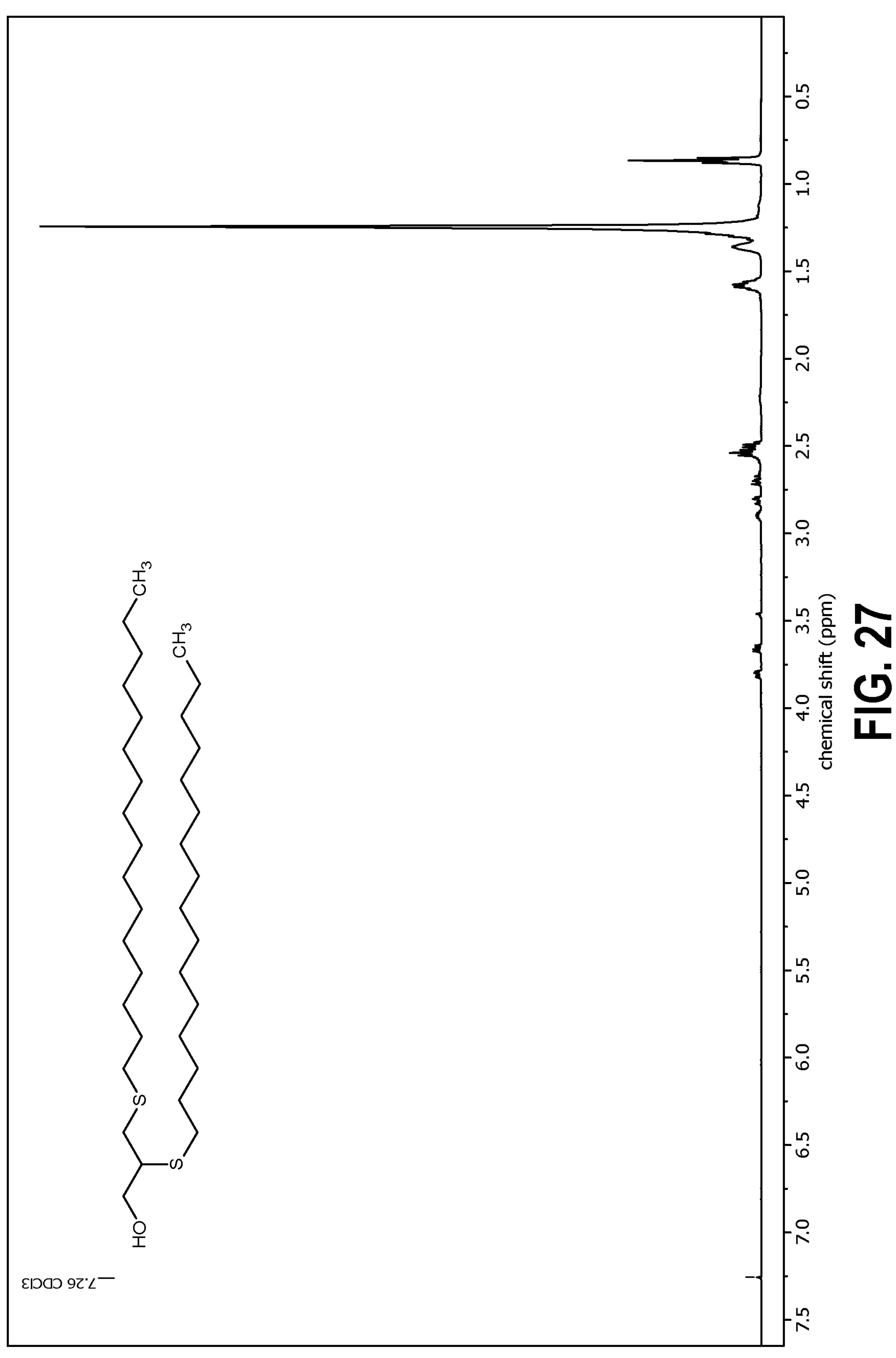
FIG. 27 shows a 300 MHz $^{1}H$ NMR of 2,3-di(hexadecanethioether) propyl alcohol monomer (298 K, $CDCl_3$).

Synthesis of 3,3-bis(hexadecylthio)propan-1-ol: Propargyl alcohol was added to a dry vial containing a stir bar, after which a stoichiometric amount of hexadecanethiol, and Irgacure 819 (1% wt), were added. The vial was heated while stirring to 80° C. and held isothermal for 24 h. During the isothermal treatment, the vial was irradiated with 365 to 420 nm (50 W) and was a yellowish liquid. Upon cooling, the product was a yellowish waxy solid, which was precipitated into cold methanol and collected as a white solid (Yield=92%) $^{1}H$ NMR ($CDCl_3$): (FIG. 27).

Film Synthesis: Stoichiometric amounts of the epoxide monomer and PETMP were mixed in a vial along with 5 wt % acetone until a homogeneous solution was achieved, and the solution was then cooled to 0° C. To this solution, DBU was added and the solution was poured onto a flat, smooth silicone sheet. The film was allowed to warm to ambient temperature over a 24 h period, after which the film was heated for an additional 24 h period at 120° C.

Foam Synthesis: Polymer foam was produced by adding the epoxide monomer, PETMP, the surfactant, acetone (for dissolving reactants and to serve as a physical blowing agent), and the organobase catalyst into a single container. For the BADGE foam synthesis, BADGE monomer was added to a beaker and dissolved in 2 mL of acetone. Stoichiometric amounts of PETMP and 2 g of Silslab 2790 were added to the same beaker and mixed until all reagents were dissolved into a homogenous, low viscosity solution. To a second beaker, 0.260 g DBU and 2 mL were added and mixed. While stirring the beaker containing BADGE, the DBU solution was added as a single unit as quickly as possible, and the mixture was stirred for an additional 20 s before being placed on a room temperature surface. At this time, the foam rose and solidified over a 30 s period. The reaction was carried to completion by incubating the foam in a 120° C. oven for 12 h afterwards. Following this, the foam was removed, cut into cubes and rectangular prisms, and washed with an alternating organic solvent and water washes using a modified protocol previously described, substituting acetone for isopropyl alcohol. After washing, foams were dried overnight and then used for subsequent characterizations.

Figure 33:
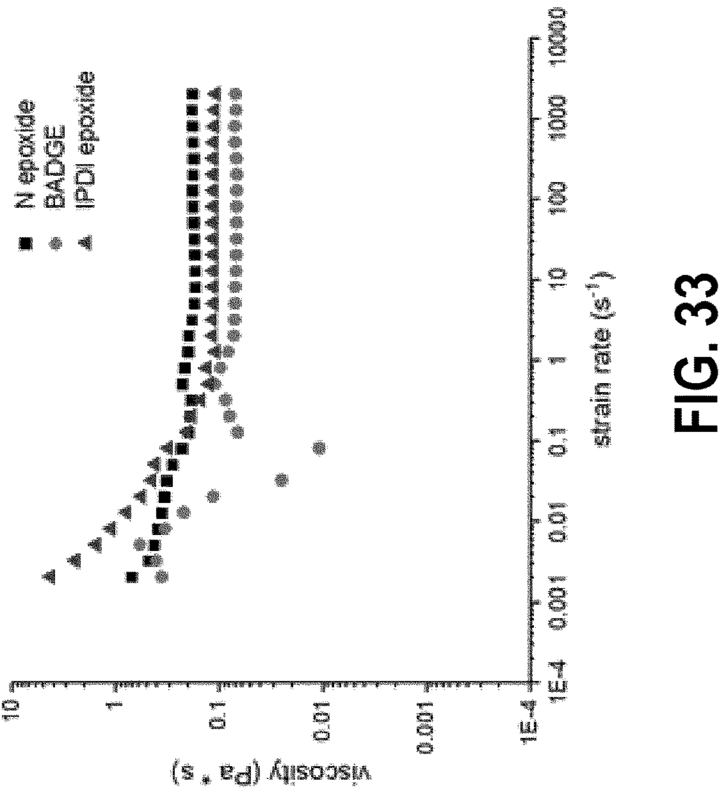
FIG. 33 shows a rheological characterization of the epoxide-thiol premixes, displaying the shear strain rate sweeps. Samples were tested at ambient conditions, 500 μm gap, 40 mm parallel plates.
Figure 32:
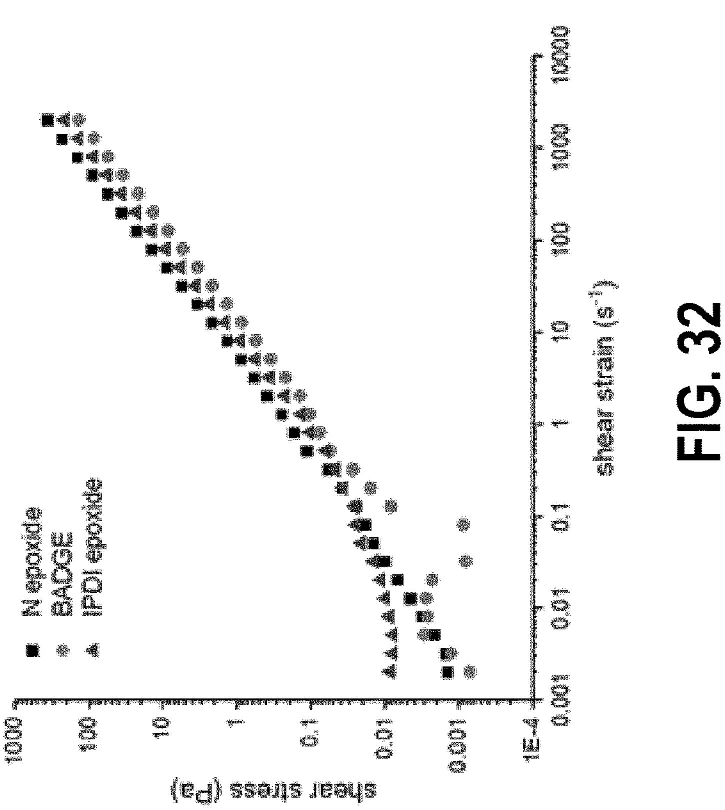
FIG. 32 shows a rheological characterization of the epoxide-thiol premixes, displaying the shear strain rate sweeps. Samples were tested at ambient conditions, 500 μm gap, 40 mm parallel plates.
Figure 35:
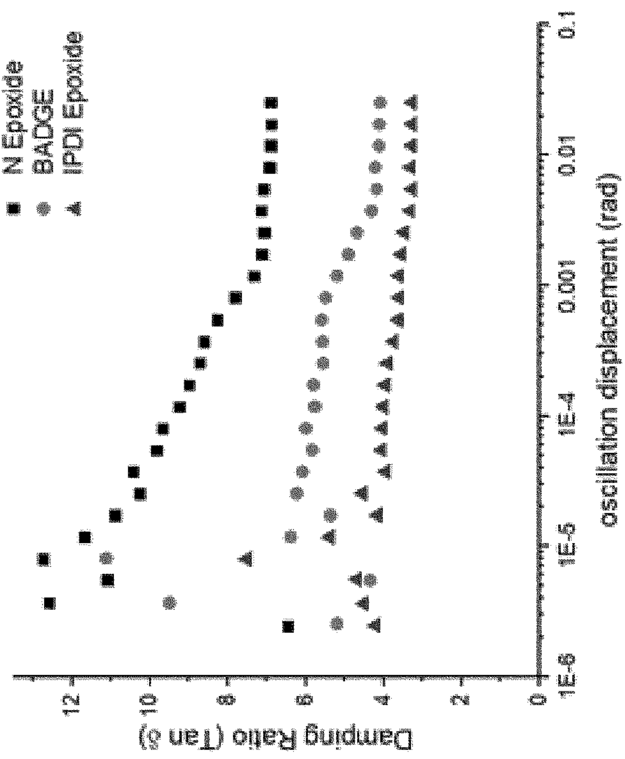
FIG. 35 shows a rheological characterization of the epoxide-thiol premixes displaying the oscillation displacement sweeps. Samples were tested at ambient conditions, 500 μm gap, 40 mm parallel plates.
Figure 34:
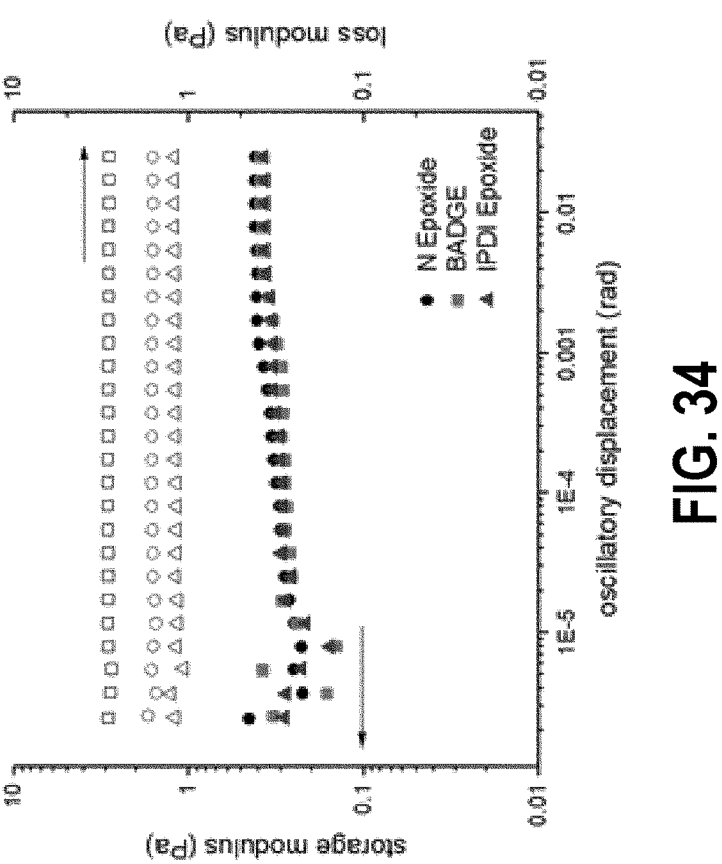
FIG. 34 shows a rheological characterization of the epoxide-thiol premixes displaying the oscillation displacement sweeps. Samples were tested at ambient conditions, 500 μm gap, 40 mm parallel plates.

Data relating to the premixes for the foams are shown in FIG. 32. Specifically, FIG. 32 shows a rheological characterization of the epoxide-thiol premixes, displaying the shear strain rate sweeps. Samples were tested at ambient conditions, 500 μm gap, 40 mm parallel plates. Furthermore, FIG. 33 shows a rheological characterization of the epoxide-thiol premixes, displaying the shear strain rate sweeps. Samples were tested at ambient conditions, 500 μm gap, 40 mm parallel plates. In addition, FIG. 34 shows a rheological characterization of the epoxide-thiol premixes displaying the oscillation displacement sweeps. Samples were tested at ambient conditions, 500 μm gap, 40 mm parallel plates. Even further, FIG. 35 shows a rheological characterization of the epoxide-thiol premixes displaying the oscillation displacement sweeps. Samples were tested at ambient conditions, 500 μm gap, 40 mm parallel plates.

Rheological Characterization: Stoichiometric amounts of PETMP and the corresponding epoxide were first mixed together and then added to the parallel plate geometry on the rheometer (500 μm) at room temperature, at which time the samples were subjected to uniaxial rotation and oscillatory shears. Subsequent testing of the reaction kinetics was done including 0.1 wt % DBU.

Foaming kinetics were studied using the foam mixture composition, including surfactants and solvent, with the gap set to 700 μm specifically for this test only in a customized testing array allowing for videography from below. A kinetic sweep (timed flow) was performed, with a constant oscillatory rotation of 1% at 1 Hz conducted. At 100 s, a 0.1 wt % solution of DBU on the reactive components (0.5 mL volume total in acetone) was added at a rate of 10 mL×min$^{-1}$. The foaming was recorded both optically and by the rheometer.

Compressive and Tensile Thermomechanical Testing: A TA Instruments DMA 800® in compression mode was used for analyzing mechanical properties of the SMP foams. 1 cm$^3$ foams were centered in the test platens, and the sample was first equilibrated at 25° C. for 1 min, after which the sample was compressed at 5 mm×min$^{-1}$ to failure as defined by the instrument, specifically the static force or yield point of the sample. Elastic moduli, ultimate stress and strain, toughness, and strain at failure (corresponding to the aforementioned definition) were calculated from the corresponding stress-strain curves.

Figure 48:
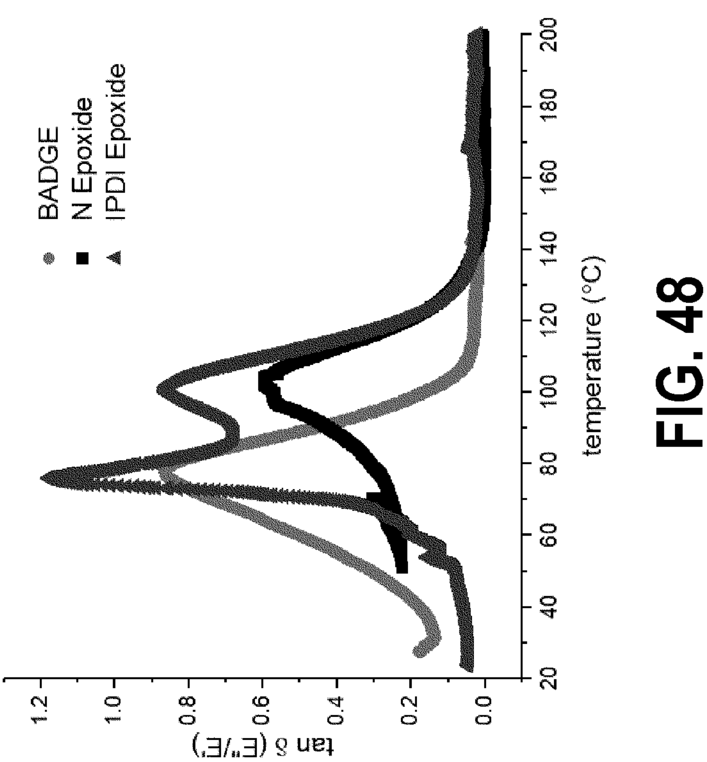
FIG. 48 shows a representative thermomechanical analysis of porous, thermoset SMP foams, displaying the damping ratio (tan 8). Cylindrical samples (1 $cm^3$) were tested in compression at 1 Hz, preload force of 0.01 N, heated from 20° C. to 200° C. at 10° C.×$min^{-1}$ at ambient atmosphere, n=3 for each species.
Figure 47:
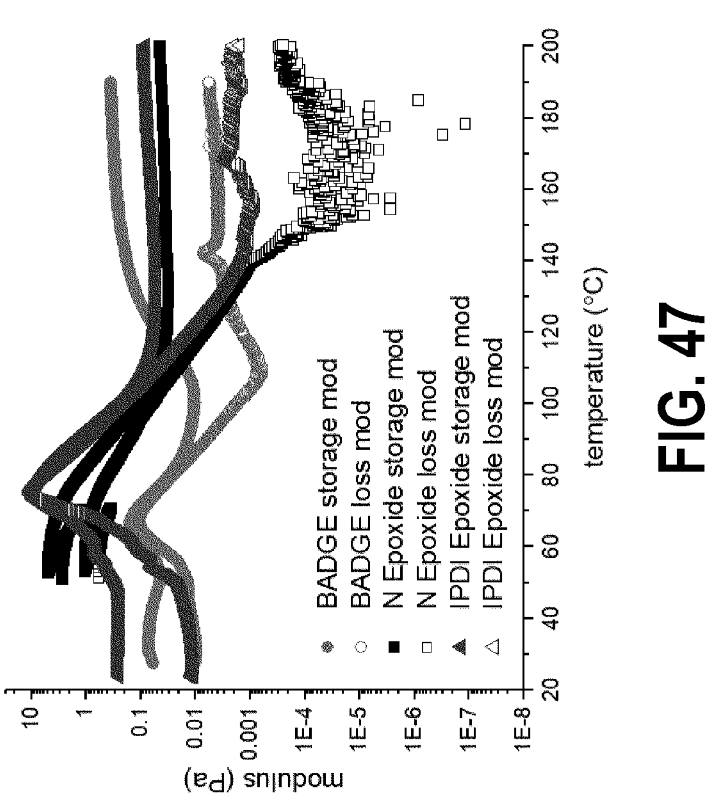
FIG. 47 shows a representative thermomechanical analysis of porous, thermoset SMP foams, displaying the moduli. Cylindrical samples (1 $cm^3$) were tested in compression at 1 Hz, preload force of 0.01 N, heated from 20° C. to 200° C. at 10° C.×$min^{-1}$ at ambient atmosphere, n=3 for each species.

Thermal properties of foams were characterized using the same instrument, with samples incubated at 25° C. followed by a 2° C.×min$^{-1}$ ramp to 220° C. During heating, samples were compressed with a 5 mN force, with a 10 Hz oscillatory load applied over the course of the test. Representative thermomechanical analysis of the porous, thermoset SMP foams was conducted. FIG. 47 shows a representative thermomechanical analysis of porous, thermoset SMP foams, displaying the moduli. Cylindrical samples (1 cm$^3$) were tested in compression at 1 Hz, preload force of 0.01 N, heated from 20° C. to 200° C. at 10° C.×min$^{-1}$ at ambient atmosphere, n=3 for each species. FIG. 48 shows a representative thermomechanical analysis of porous, thermoset SMP foams, displaying the damping ratio (tan 8). Cylindrical samples (1 cm3) were tested in compression at 1 Hz, preload force of 0.01 N, heated from 20° C. to 200° C. at 10° C.×min$^{-1}$ at ambient atmosphere, n=3 for each species.

Figure 25:
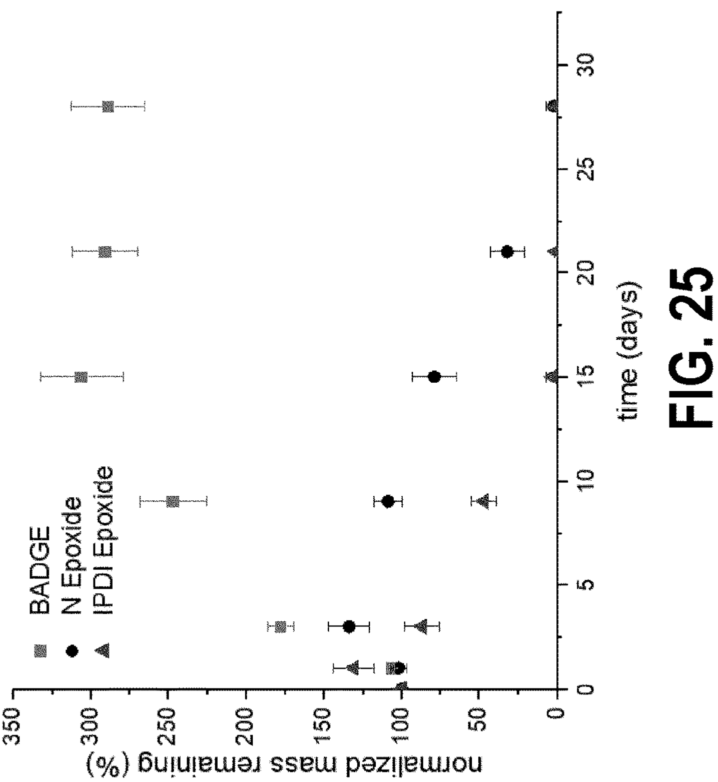
FIG. 25 shows a gravimetric analysis of SMP foams in 30% H2O2 at 37° C. PBS, temperature maintained in a shaker, 1 Hz, n=5.
Figure 24:
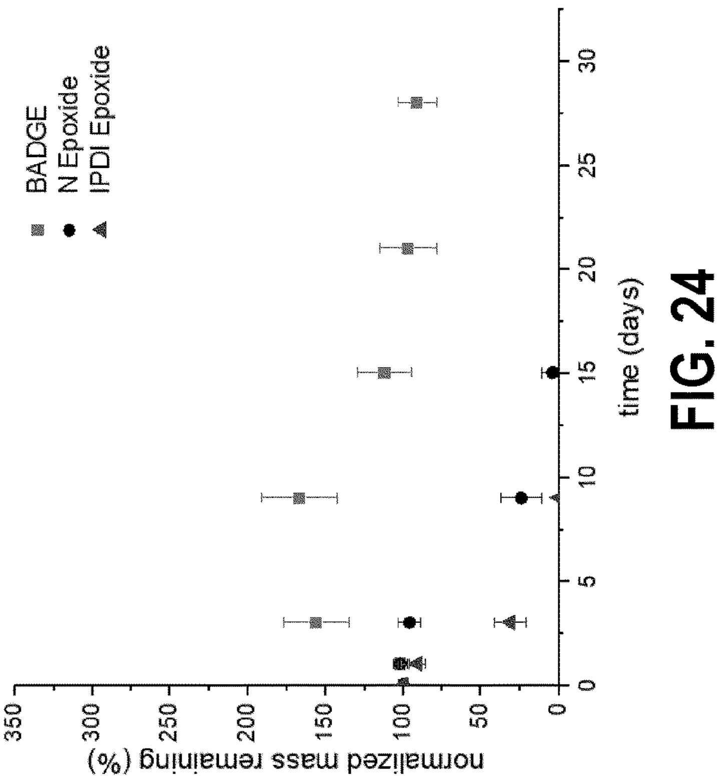
FIG. 24 shows a gravimetric analysis of SMP foams in 1 M NaOH at 37° C. PBS, temperature maintained in a shaker, 1 Hz, n=5.

Degradation: Cubes (~2 cm$^3$) were cut using a hot wire cutter and weighed in milligrams. Each cube was then immersed in 10 mL of either 35% $H_2O_2$ or 1.0 M NaOH, respectively. At discrete timepoints, samples were removed from the degradation solutions, blotted dry, and weighed. At the same time, the used degradation solution was replaced with fresh solution, and the samples were again immersed and incubated. FIG. 24 and FIG. 25 show gravimetric analyses of SMP foams in 1 M NaOH at 37° C. PBS, temperature maintained in a shaker, 1 Hz, n=5.

These conditions, as well as the 37° C. incubation temperature and 1 Hz solution perturbation, were selected to both address possible translation of these materials towards biological applications as well as using the aggressive conditions as the most likely problematic to be experienced.

Oil Reclamation and Surface Funcdionalization: Cubes (~1 cm$^3$) were cut using a hot wire cutter and immersed in acetone at 37° C. for 24 h, after which they were immersed in isophorone diisocyanate solution (50 wt %) for another 24 h at 50° C. Samples were washed in clean acetone, sponged dry, and then immersed immediately in either 20 mL hexadecanethiol (with 1 wt % DBU) or 20 mL of 2,3-di(hexadecanethioether) propyl alcohol. FIG. 27 shows a 300 MHz $^1$H NMR of 2,3-di(hexadecanethioether) propyl alcohol monomer (298 K, $CDCl_3$). After 48 h incubation at 50° C., samples were washed with acetone and allowed to dry for 48 h at 50° C. Samples were then immersed in a 1:1 (vol:vol) tube of oil and DI $H_2O$ for varying times in both the expanded and compressed states, with samples examined at both 20° C. and 30° C.

Referring to FIG. 1, the use of three different epoxide-containing monomers to produce porous polymer foams leveraged the nucleophilicity of the PETMP monomer in the presence of the organobase DBU. BADGE and N Epoxide monomers are commercially available and have been explored for a host of different applications, however IPDI was first synthesized from a reaction of isophorone diisocyanate and glycidol, resulting in a dual-epoxide functionalized monomer containing two urethane linkages.

Figure 2:
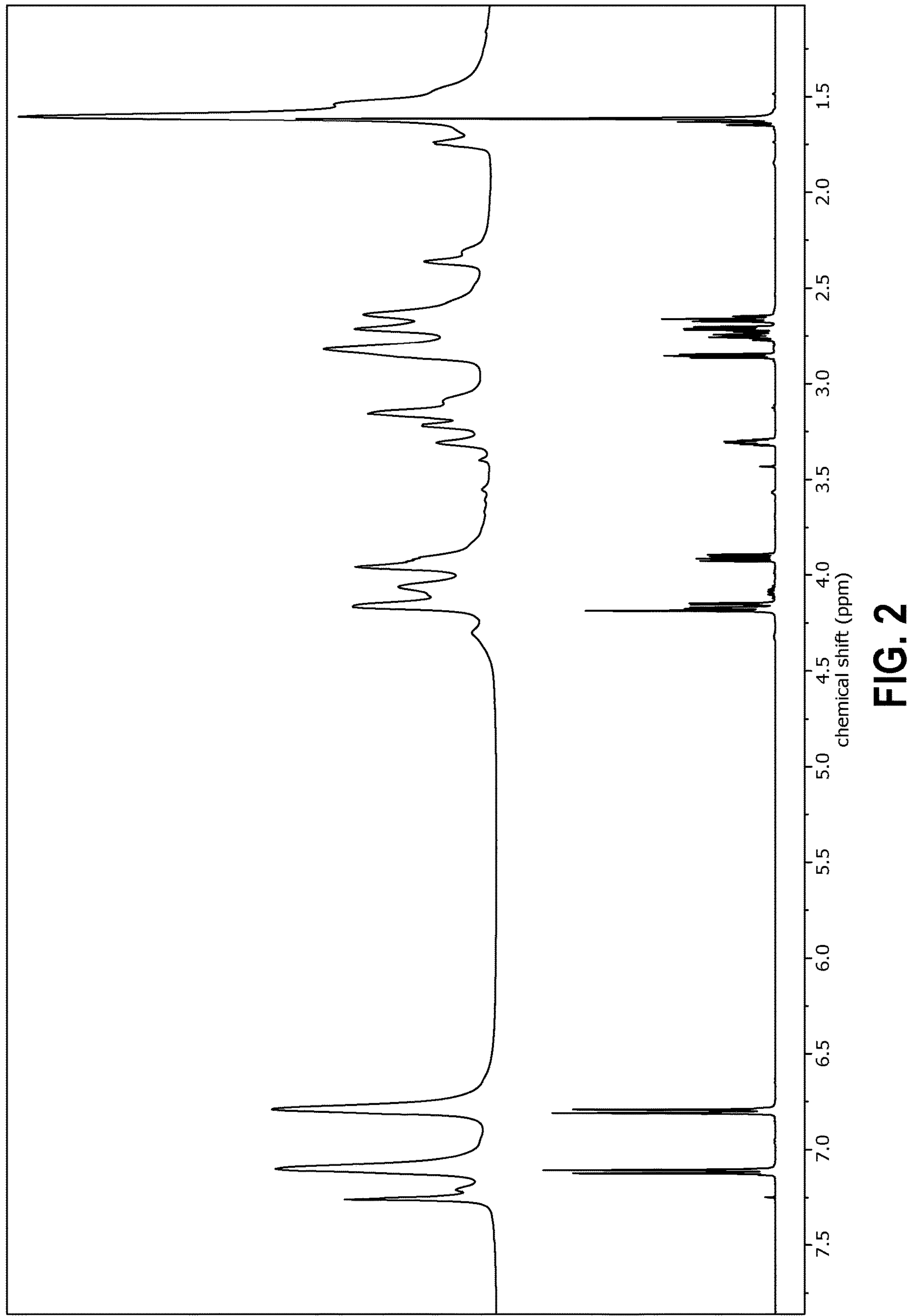
FIG. 2 shows a representative $^{1}H$ NMR of monomers BADGE and PETMP in CDCl3 (bottom) and after 5 min incubation with DBU at room temperature (top; resulted in solidification of the NMR solution); conducted on 300 MHz Bruker NMR, 298 K, ambient atmosphere.

The reaction of the epoxide moiety with the thiol nucleophile on the PETMP molecule, qualitatively, took place rapidly, and was denoted by an increase in vessel temperature as well as gas formation in solution. Spectroscopically, crosslinking was noted by the broadening of most peaks, as well as the formation of peaks at 2.36 and 2.14 ppm (shown in FIG. 2), likely associated with ring opening of the epoxide and the alpha protons from the thioether bond. The shifting of peaks from 3.917 to 3.957 ppm also denotes the ring opening by the organobase, DBU. This trend was repeated with the other formulations. Finally, the solutions within the NMR tube were found to have gelled into a solid over the course of the experiment.

Additionally, the formation of the peak at 3.15 indicates the formation of disulfide bonds, which are likely a side product of an organobase-catalyzed epoxy ring opening. It was hypothesized that the disulfide formation is likely 5% byproduct for in-air reactions.

Figure 30:
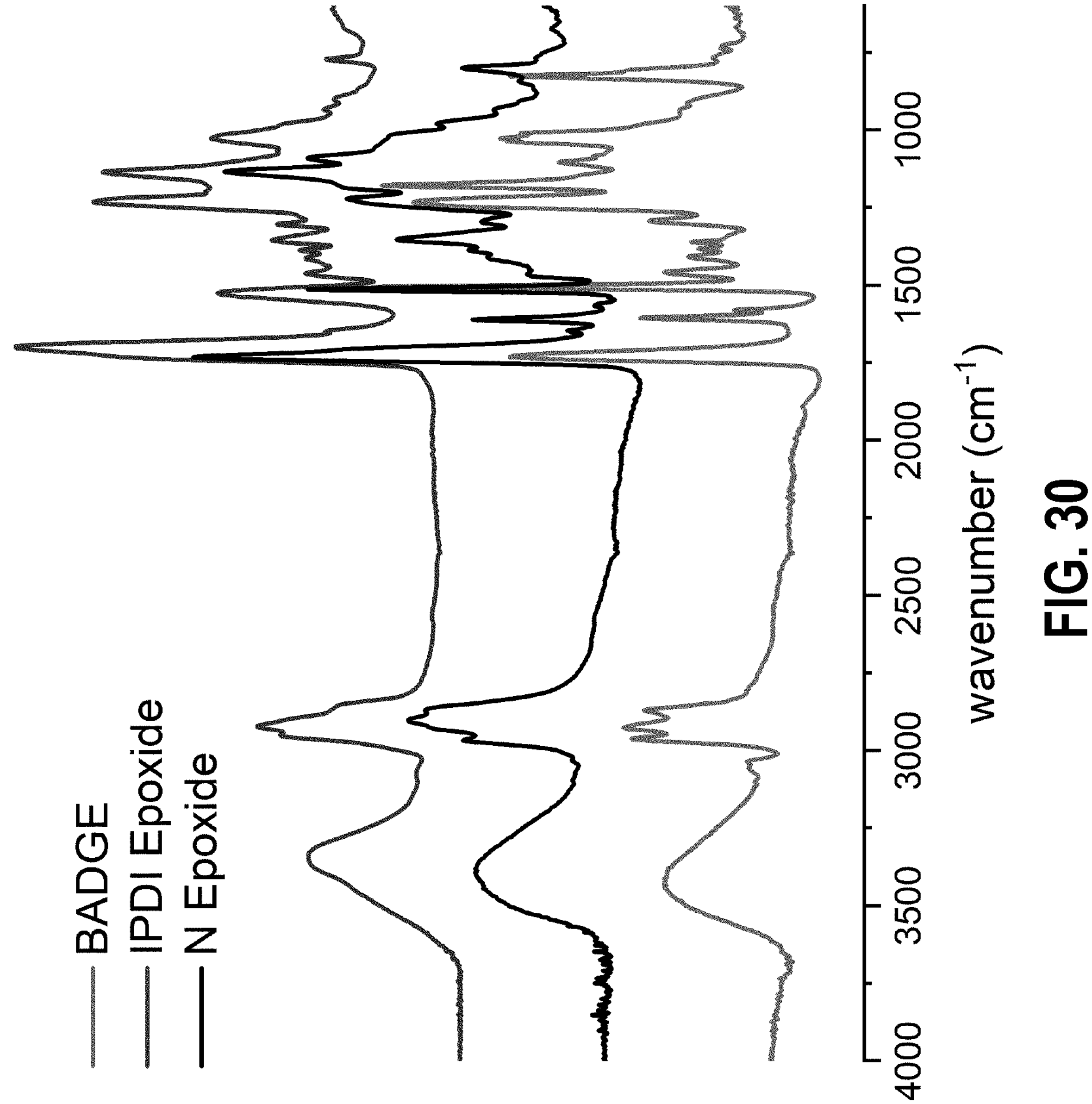
FIG. 30 shows a FTIR comparisons of the film and foam BADGE materials (lowest) and comparing the foamed materials of IPDI epoxide (middle) and N epoxide (top).
Figure 31:
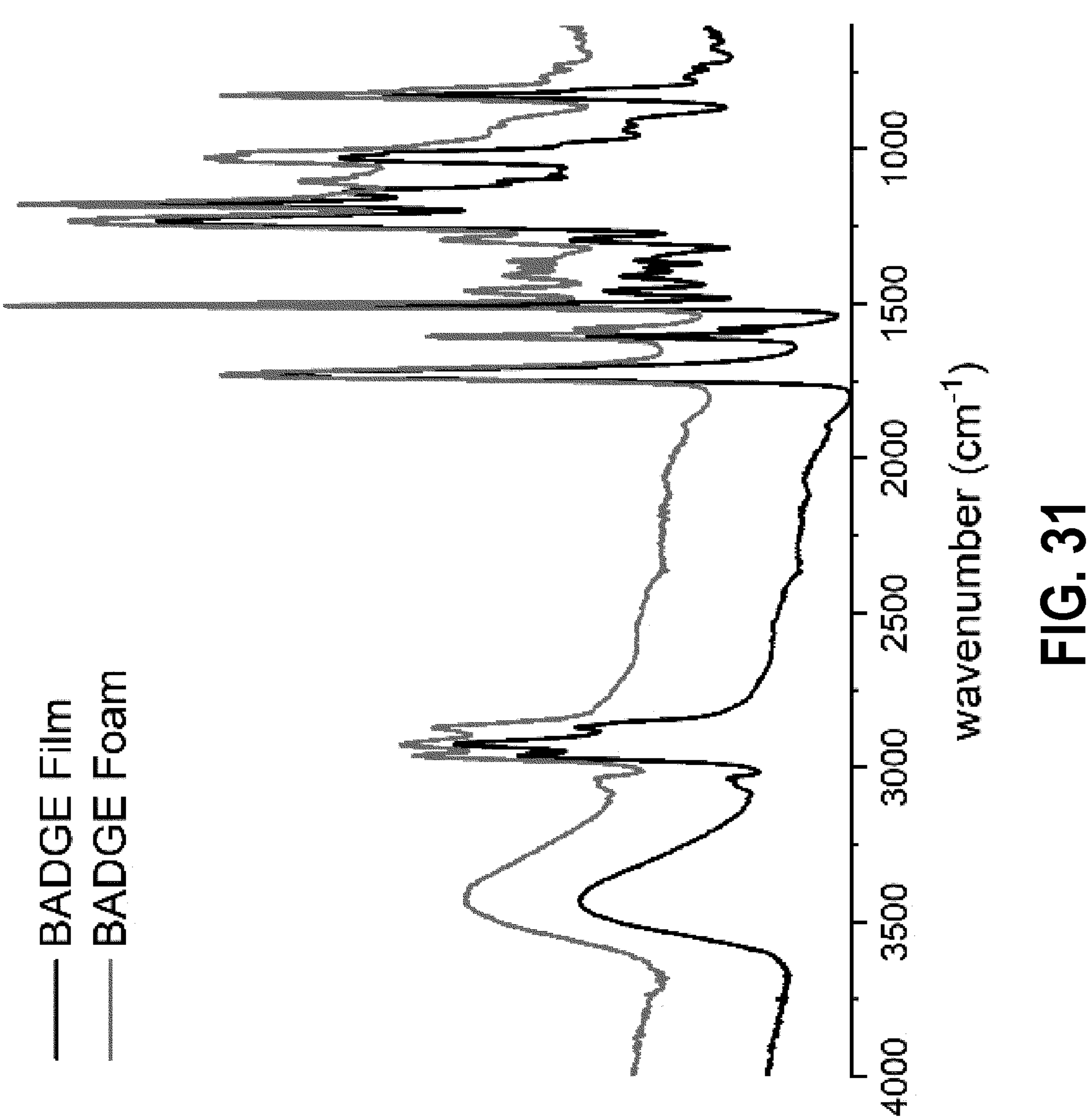
FIG. 31 shows a representative FT-IR spectra of films (lower) and foams (upper) of BADGE-derived poly(β-hydroxythioethers)

FT-IR ATR was further conducted to analyze both the resultant film and foam materials (FIG. 30 and FIG. 31). While polyurethane chemistry often displays differences between the foam and non-porous media forms of the materials due to the numerous side reactions, including oligomeric formation of polyureas within even crosslinked materials, these poly(β-hydroxythioether)s are shown to be similar.

The carbonyl peak, a characteristic peak found in many different foams, appeared at 1731 (±1) $cm^{-1}$ for the BADGE and N Epoxide materials, while the IPDI Epoxide carbonyl peak was found at 1698 $cm^{-1}$. The BADGE and N Epoxide materials possess a carbonyl peak solely because of the PETMP monomer, and thus the peak is narrow and sharp as characteristic of aliphatic esters. Furthermore, the in-chain ester linkage has no hydrogen bonding, and therefore will appear at a higher wavenumber. By comparison, the IPDI Epoxide materials possess three different carbonyl linkages: PETMP esters, and both a primary and secondary carbamate. Previous work with aliphatic polyurethanes has indicated that the hydrogen bonding of urethane linkages (carbamates) will shift the carbonyl stretch to lower wavenumbers as found here. Additionally, a very slight shoulder is found at 1647 $cm^{-1}$, associated with bidentate ureas (both amines participating in hydrogen bonding with another carbonyl) and possibly indicating slight impurities in the final material. The lack of peaks in the 2500 to 2700 $cm^{-1}$ region indicates that the thiols are consumed during synthesis. Peaks at 772 $cm^{-1}$ (IPDI Epoxide), 800 $cm^{-1}$ (N Epoxide) and 827 $cm^{-1}$ (BADGE) are indicative of the thioether linkage.

In fact, differences between the materials will be primarily due to incomplete extraction of surfactants and residual solvents, as the foaming reaction is purely physical, with the thiol-epoxy "click" reaction being sufficiently exothermic to evaporate the acetone as the polymer network forms. These bubble nucleation sites will then form the pores within the foam, with gaseous diffusion enabled by the presence of the surfactant. While this is similar to the more traditional polyurethane two-step foaming method, the synthesis of foams was conducted over a 5 min period, where the epoxide and thiol monomers were added in a single pot along with a surfactant, acetone as a blowing agent, and the organobase DBU. Stoichiometric balances were maintained, while acetone and DBU concentrations were varied, resulting in different foam pore sizes and distributions. During the foaming process itself, the best results were obtained by mixing all components together at room temperature and allowing the reaction to proceed spontaneously (over the course of approximately 1 min).

Figure 4:
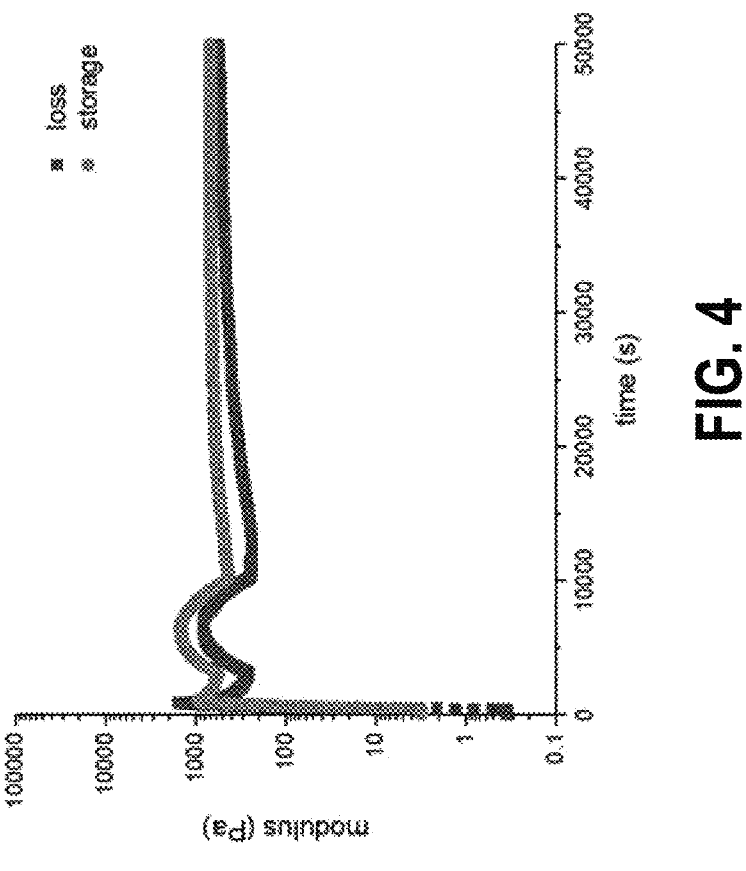
FIG. 4 shows the reaction kinetics of the BADGE-PETMP thermoset during oscillatory parallel plate shearing.
Figure 37:
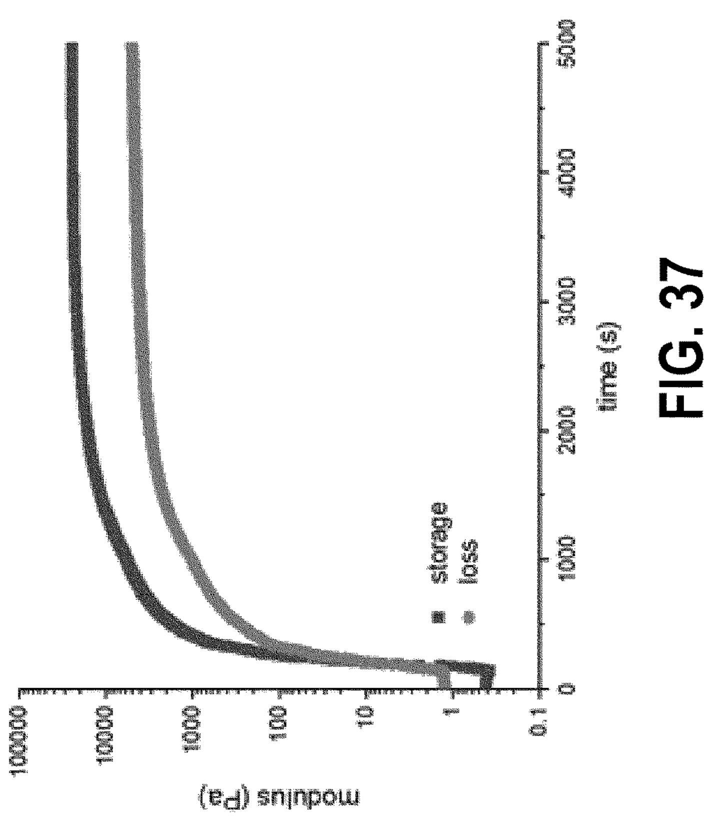
FIG. 37 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation.
Figure 36:
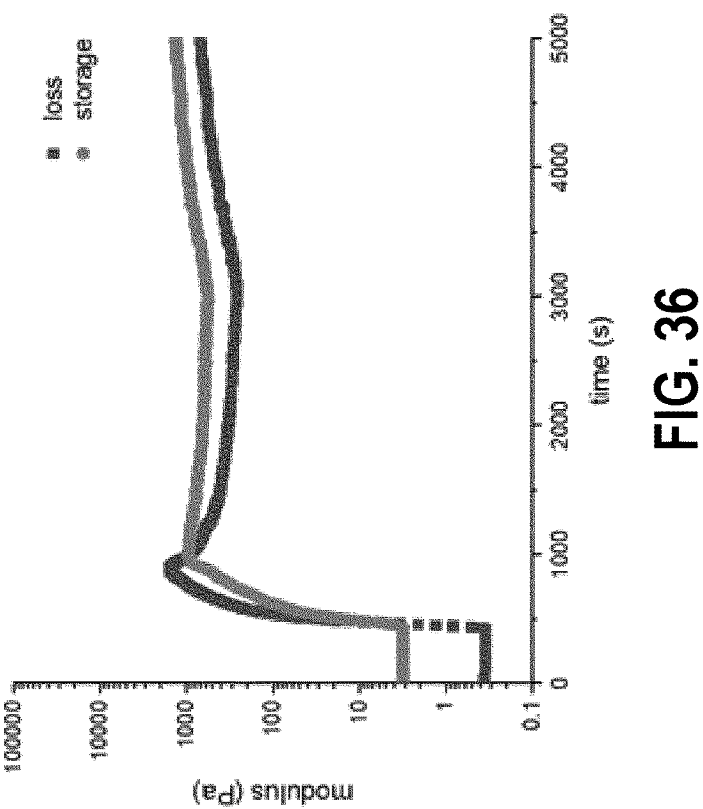
FIG. 36 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation.
Figure 39:
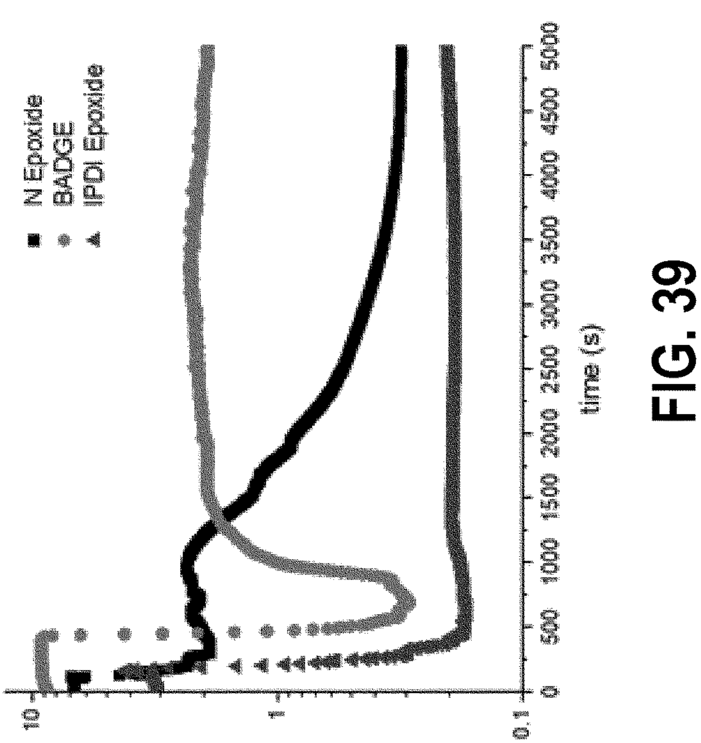
FIG. 39 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation.
Figure 38:
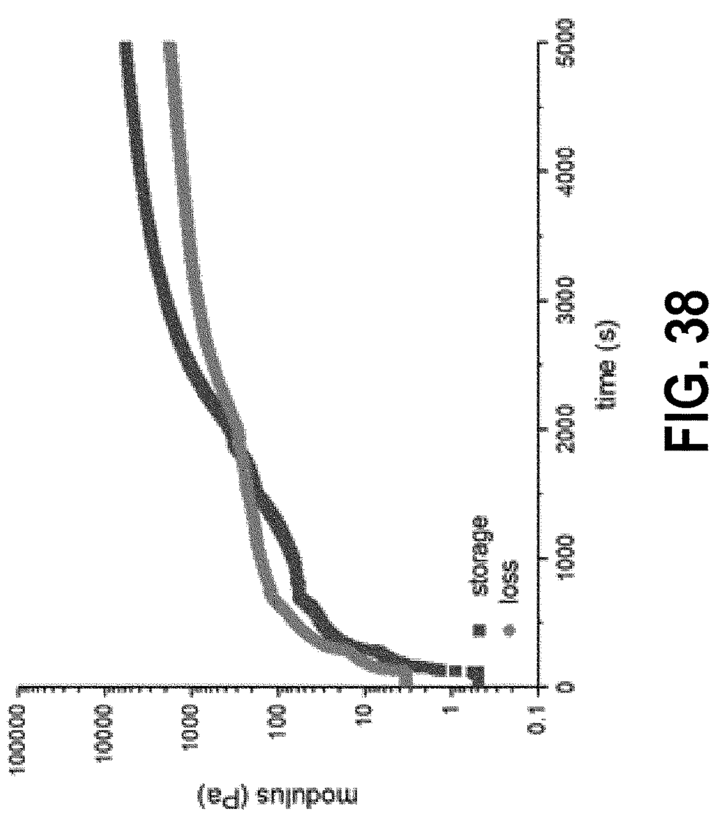
FIG. 38 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation.

The behavior of the materials during and prior to the foaming process were characterized using rheology, with the mixtures displaying Newtonian fluid behavior prior to the addition of the DBU catalyst (as evidenced by the data shown in FIG. 3 and FIGS. 32-35). The kinetics of the reaction between the epoxide and thiol monomers was further characterized without the presence of surfactants and catalysts (as shown in FIG. 4) and with these additives to assist with foaming (as shown in FIG. 5 and FIGS. 36-39). Specifically, FIG. 36 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation. FIG. 37 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation. FIG. 38 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation. FIG. 39 shows a rheological characterization of the reaction kinetics of the BADGE-PETMP, the IPDI Epoxide PETMP mixture, and the N Epoxide-PETMP mixtures during oscillatory parallel plate shearing, with the DBU catalyst introduced at 100 s, gap of 700 μm, 40 mm parallel plate, 1 Hz oscillation.

Figures 5, 6:
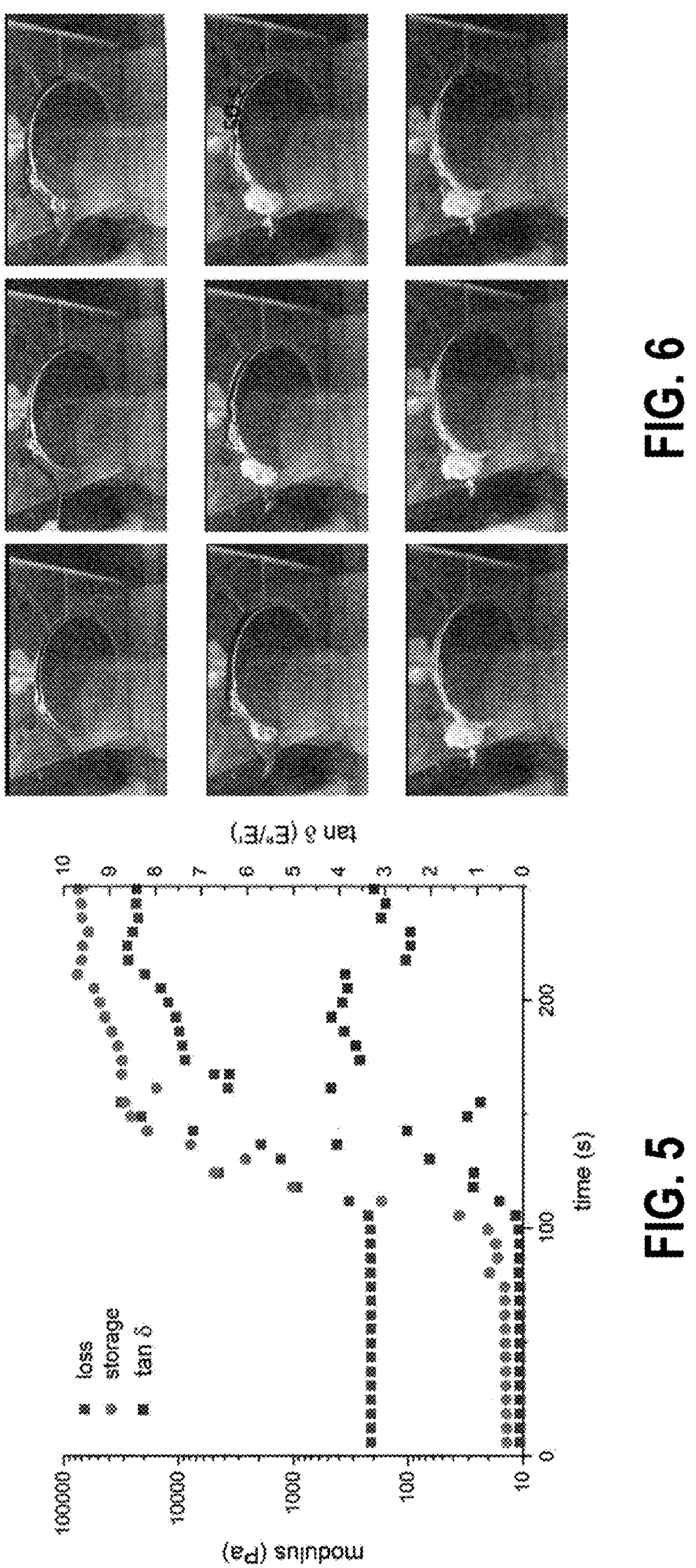
FIG. 5 shows a rheology of the BADGE-PETMP SMP foaming process, which took place in the 700 μm gap after the introduction of the organobase catalyst DBU at 80 s, foaming and rheology conducted at ambient conditions, 40 mm diameter parallel plate, 1 Hz oscillation frequency.
FIG. 6 shows images corresponding to a rheology of the BADGE-PETMP SMP foaming process which took place in the 700 μm gap after the introduction of the organobase catalyst DBU at 80 s, foaming and rheology conducted at ambient conditions, 40 mm diameter parallel plate, 1 Hz oscillation frequency.
Figure 7:
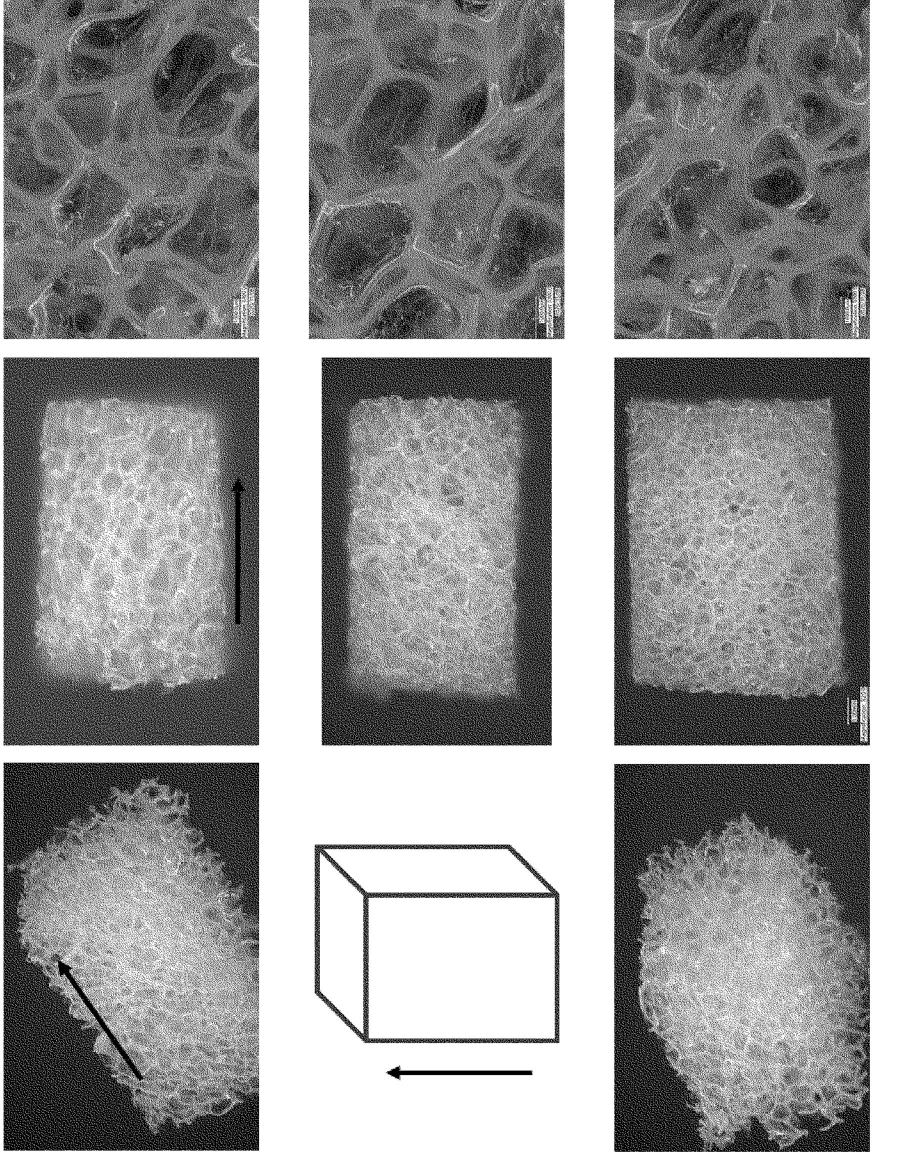
FIG. 7 shows microscopy images of BADGE foam in the axial, transverse, and foam growth axes, along with representative close images of the same foam directions.

The BADGE monomer was found to result in the most rapid reactions, although all systems reacted within minutes to form a gelled material. This is further supported by images collected during the parallel plate shear test, which displayed the rapid foaming after addition of the DBU, and are shown in FIG. 6. Specifically, the images shown in FIG. 6 correspond to a rheology of the BADGE-PETMP SMP foaming process which took place in the 700 μm gap after the introduction of the organobase catalyst DBU at 80 s, foaming and rheology conducted at ambient conditions, 40 mm diameter parallel plate, 1 Hz oscillation frequency. Furthermore, FIG. 7 shows microscopy images of these BADGE foams in the axial, transverse, and foam growth axes, along with representative close images of the same foam directions. As shown in FIG. 7, the foams formed by a method according to the invention are porous and structurally stable. While homogenous mixing was limited by the shearing profile and diffusion within the material itself, the formation of a solid foam is seen to occur within seconds of the catalysts addition (at 100 s) and corresponds to the dramatic increase in moduli as well as the phase transition of the material (tan S peak), which is similar to the behaviors found for the unfoamed (neat) thermoset materials (FIG. 33). By comparison with studies utilizing diamines and difunctional epoxides, the use of thiols with DBU was found to display rapid changes in the storage and loss moduli, with a peak tan S (denoting a material phase transition) 87 s after the addition of the catalyst.

Figure 3:
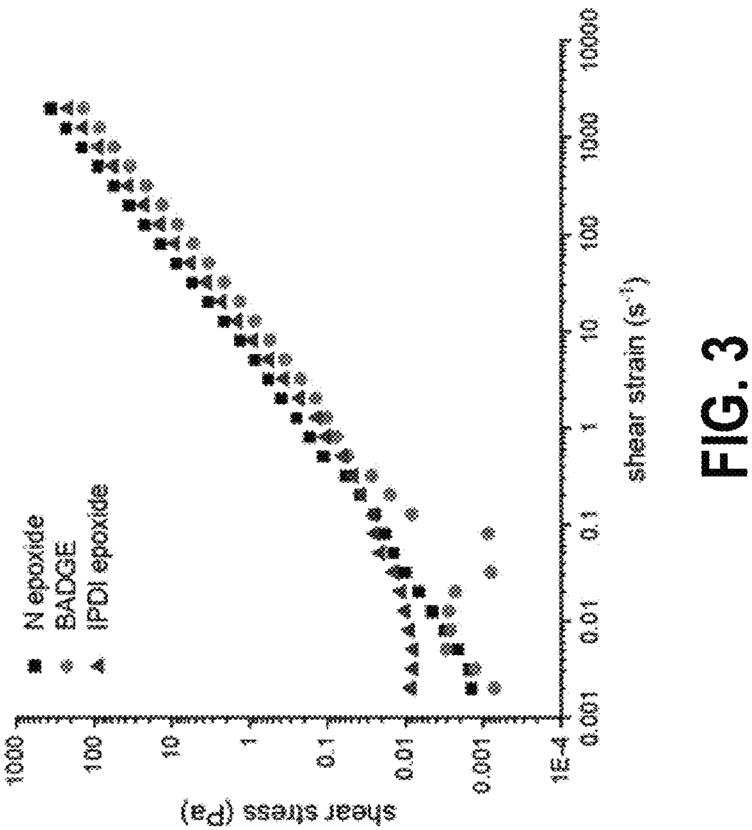
FIG. 3 shows a rheological characterization of the epoxide-thiol premixes.

Referring to FIGS. 3-5, thermomechanical analysis of the materials was conducted using dynamic mechanical analysis (DMA), with bars tested under tensile loading conditions. It was found that the foamed materials undergo a phase transition temperature at approximately 70° C. (BADGE, initial IPDI epoxide transition) and 110° C. (N Epoxide and second IPDI Epoxide peak), as measured from the tan S peak, prior to a final thermal cure. After thermal post-treatment, the samples were found to have substantially enhanced mechanical behaviors, which is significantly improved over previous attempts using different organobases and thiols as well as a timely, complicated foaming procedure involving microparticles.

IPDI Epoxide foams displayed the interesting dual-peak tan S behaviors, indicating the possibility of multi-shape recovery behaviors. The plasticized behavior of the materials displayed a single peak that is both reduced in magnitude and the temperature at which the event occurs. This type of relaxation is not unusual for polymers, where the thermosolvation of the chains causes plasticization.

TABLE 1

SMP FOAM PHYSICAL MATERIAL PROPERTIES

| BADGE Morphology | Density ($g/cm^3$) | Gel fraction (%) | Swelling Ratio (%) |
|---|---|---|---|
| Small | 0.333 ± 0.006 | 94.02 ± 0.55 | 261.5 ± 45.5 |
| Medium | 0.018 ± 0.003 | 93.64 ± 0.49 | 215.2 ± 59.1 |

TABLE 1-continued

| SMP FOAM PHYSICAL MATERIAL PROPERTIES | | | |
|---|---|---|---|
| BADGE Morphology | Density ($g/cm^3$) | Gel fraction (%) | Swelling Ratio (%) |
| Medium Large | 0.022 ± 0.002 | 91.22 ± 1.22 | 275.8 ± 36.6 |
| Large | 0.028 ± 0.003 | 90.91 ± 0.34 | 271.8 ± 17.1 |

Shape Memory Response

Figure 9:
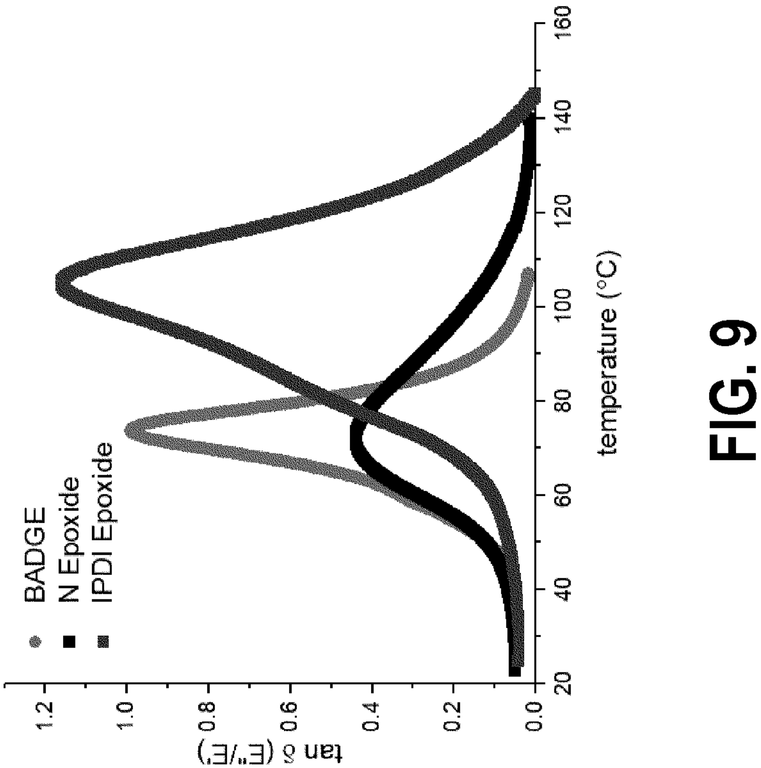
FIG. 9 shows a representative thermomechanical analysis of porous, thermoset polymer film.
Figure 8:
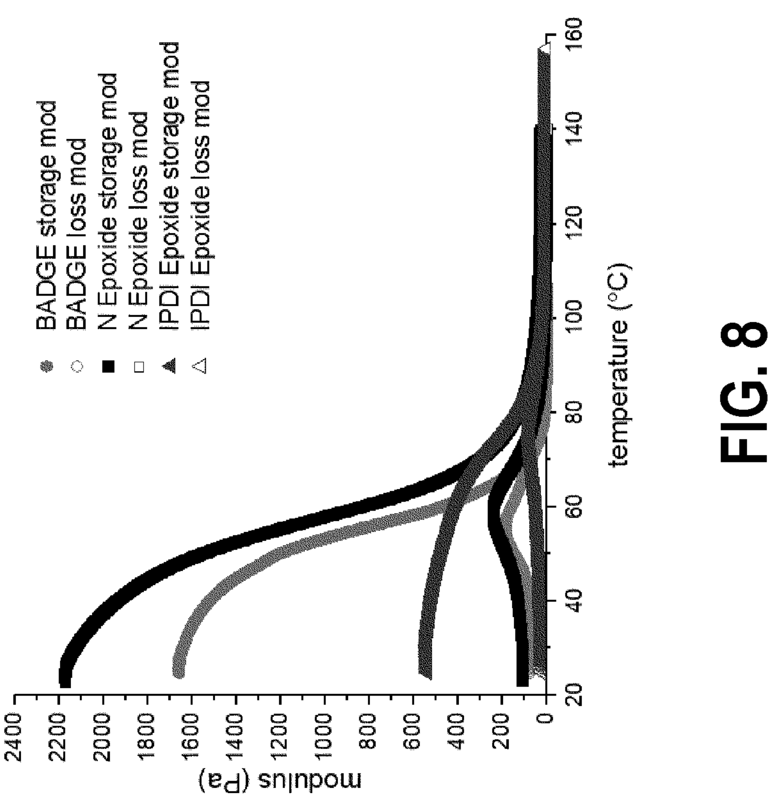
FIG. 8 shows a representative thermomechanical analysis of porous, thermoset polymer film.
Figure 10:
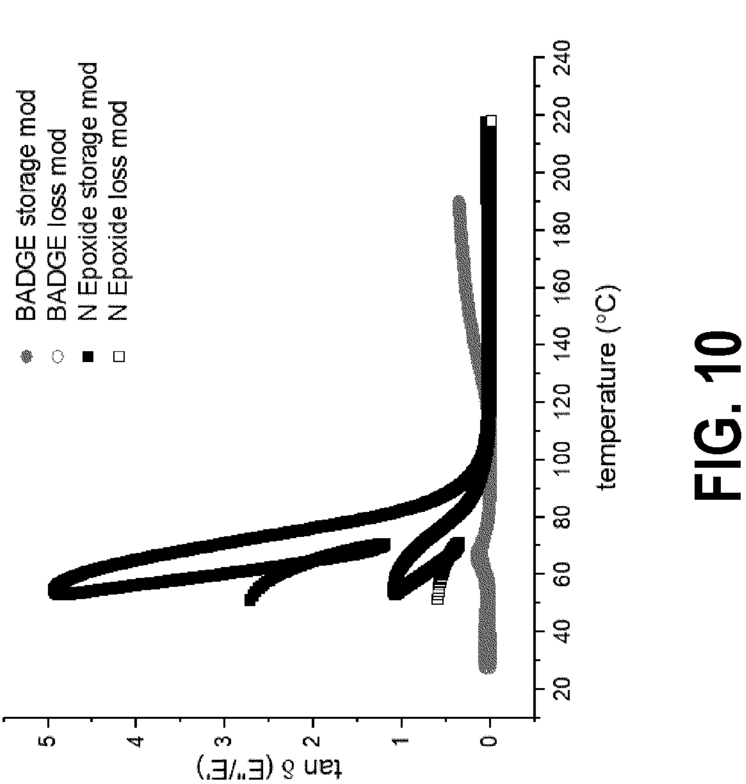
FIG. 10 shows a representative thermomechanical analysis of porous, thermoset SMP foam.
Figure 11:
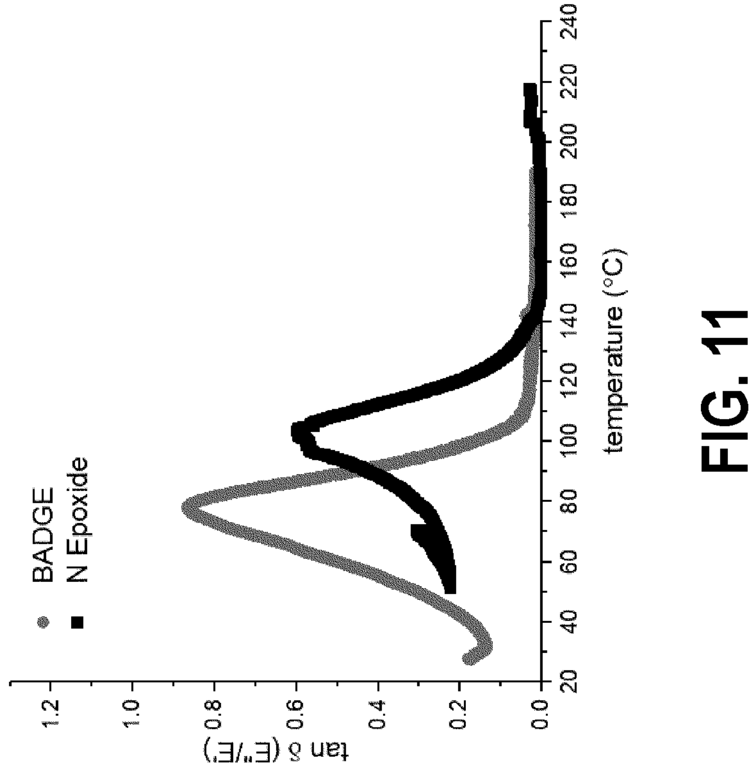
FIG. 11 shows a representative thermomechanical analysis of porous, thermoset SMP foam.
Figure 41:
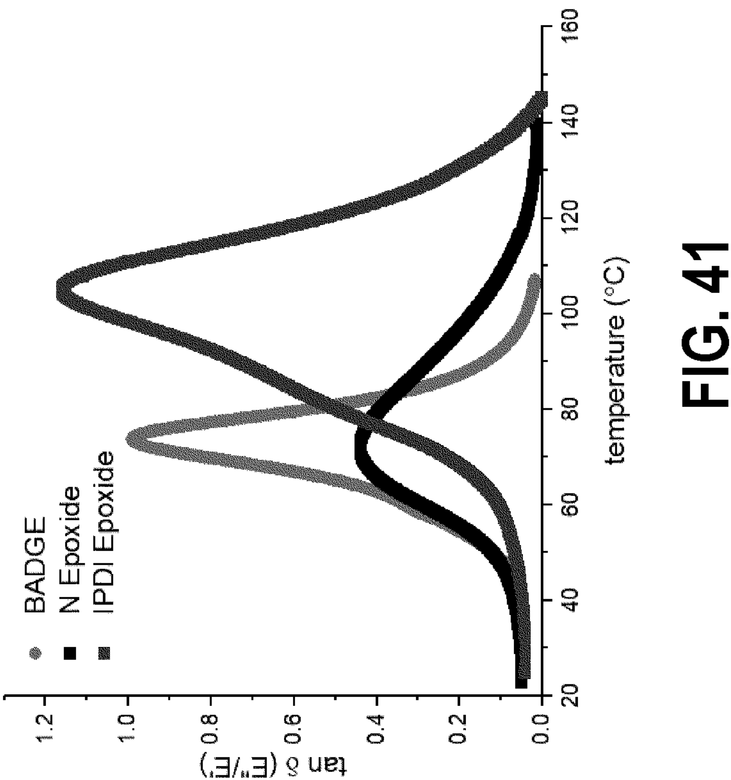
FIG. 41 shows representative DMA curves of thermoset films produced from the same thiol-epoxide reactions as the foams, were tested in tension at 1 Hz, preload force of 0.01 N, heated from 20° C. to 200° C. at 10° C.×$min^{-1}$ at ambient atmosphere, n=3 for each species.
Figure 40:
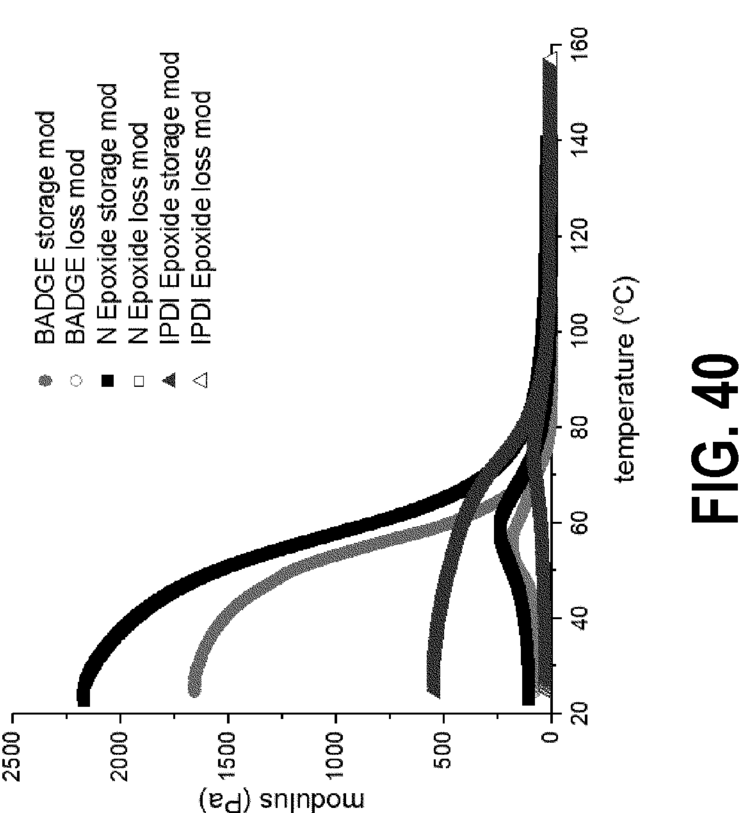
FIG. 40 shows representative DMA curves of thermoset films produced from the same thiol-epoxide reactions as the foams, were tested in tension at 1 Hz, preload force of 0.01 N, heated from 20° C. to 200° C. at 10° C.×$min^{-1}$ at ambient atmosphere, n=3 for each species.

Referring to FIGS. 6-9, the shape memory response of the materials was first examined using polymer films (data showing polymer films formed from various epoxides are shown in FIGS. 8 and 9), after which polymer foams (data showing polymer foams formed from various epoxides are shown in FIGS. 10 and 11) were used to examine changes in strain recovery as a function of total occupied volume. Regarding the films, FIG. 40 shows representative DMA curves of thermoset films produced from the same thiol-epoxide reactions as the foams, were tested in tension at 1 Hz, preload force of 0.01 N, heated from 20° C. to 200° C. at 10° C.×$min^{-1}$ at ambient atmosphere, n=3 for each species. FIG. 41 shows representative DMA curves of thermoset films produced from the same thiol-epoxide reactions as the foams, were tested in tension at 1 Hz, preload force of 0.01 N, heated from 20° C. to 200° C. at 10° C.×$min^{-1}$ at ambient atmosphere, n=3 for each species.

Figure 12:
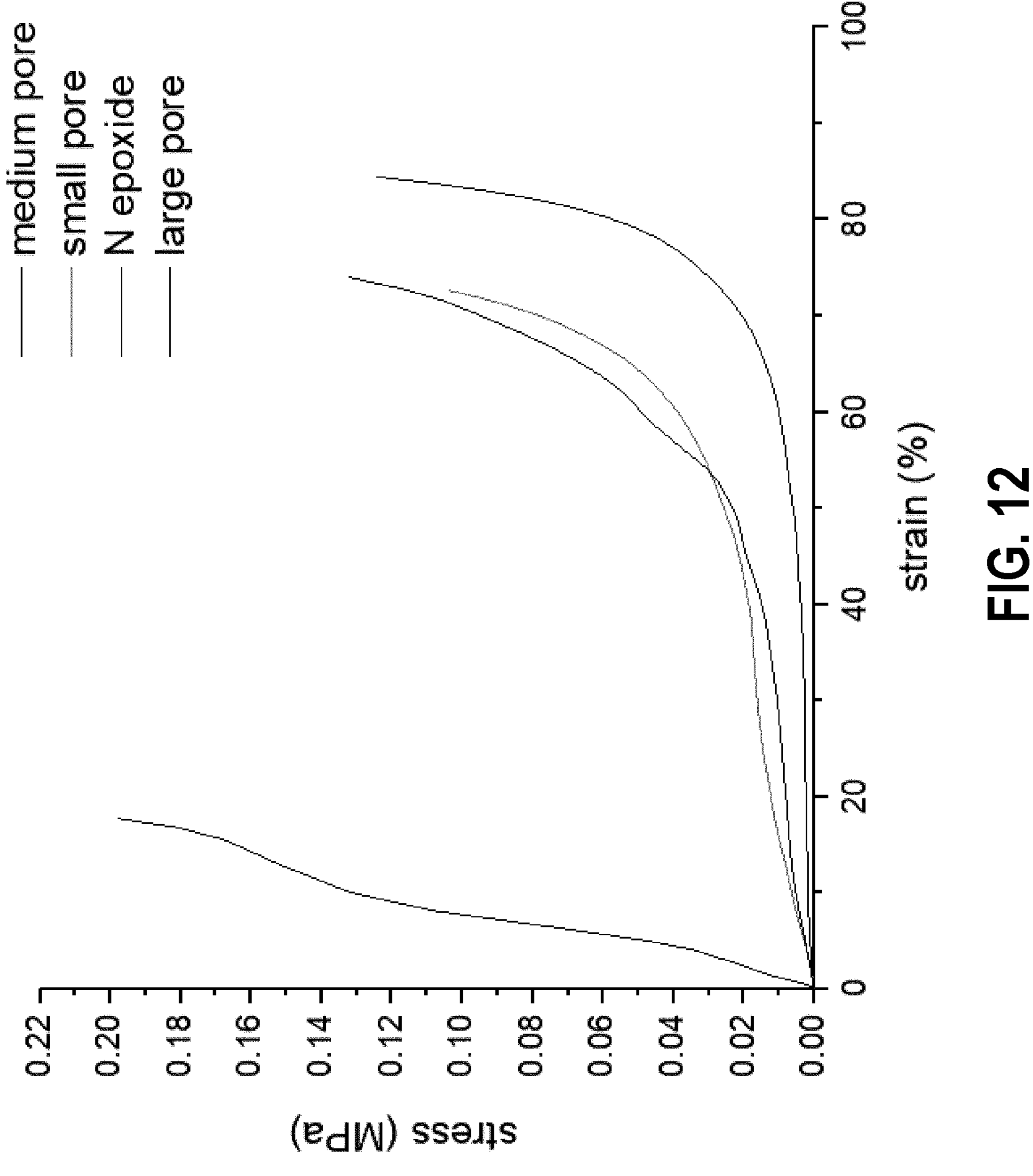
FIG. 12 shows a representative compressive stress-strain plots, compressed at 5 mm×min$^{-1}$ to yield using the dynamic mechanical analysis (DMA) at room temperature and ambient atmosphere.
Figure 13:
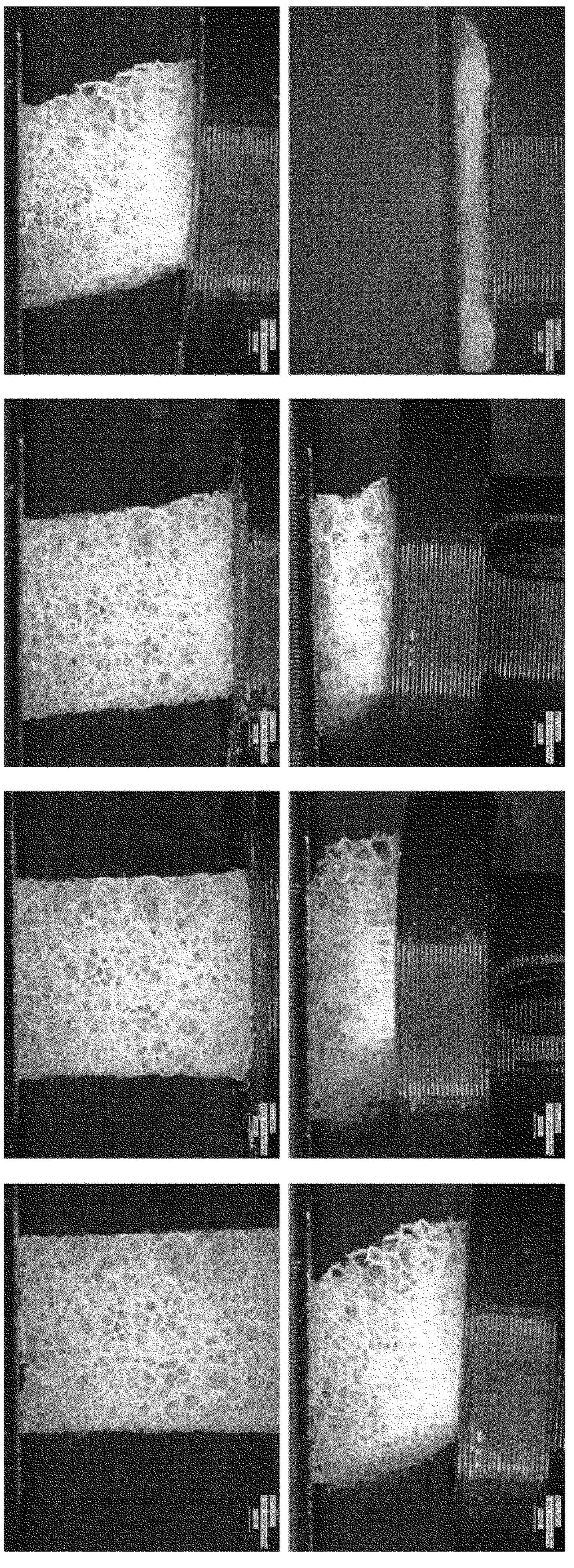
FIG. 13 shows representative microscopic images of the compressive deformation of a BADGE-PETMP SMP foam at room temperature.
Figure 43:
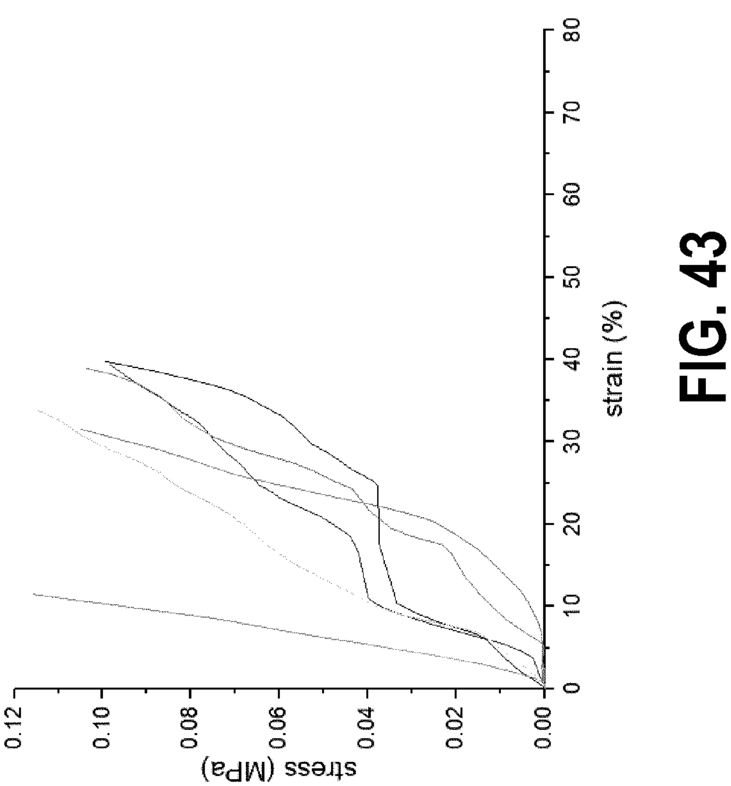
FIG. 43 shows raw stress strain curves for compressed SMP foams, compressed at 5 mm×$min^{-1}$ to yield using the DMA at room temperature and ambient atmosphere.
Figure 42:
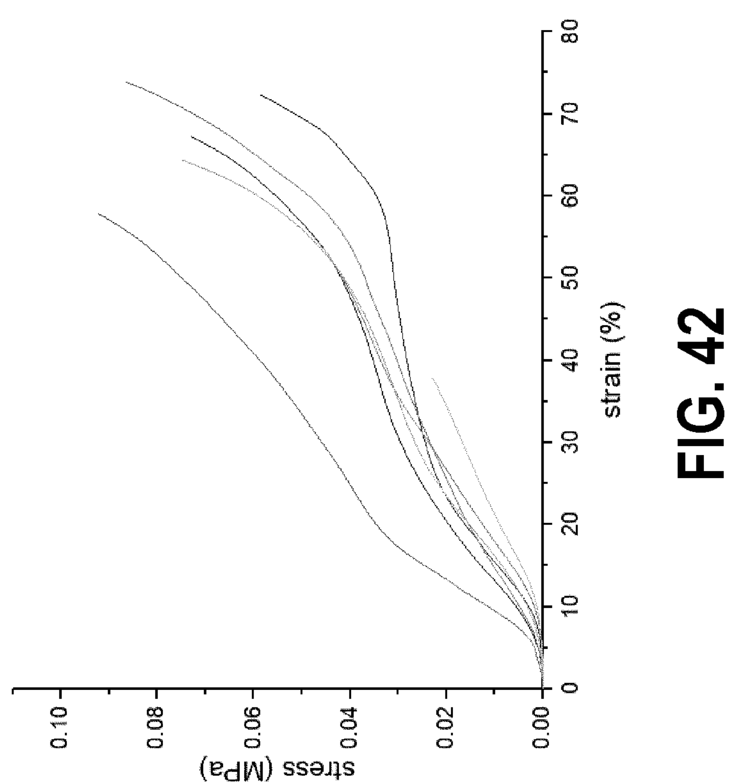
FIG. 42 shows raw stress strain curves for compressed SMP foams, compressed at 5 mm×$min^{-1}$ to yield using the DMA at room temperature and ambient atmosphere.
Figure 44:
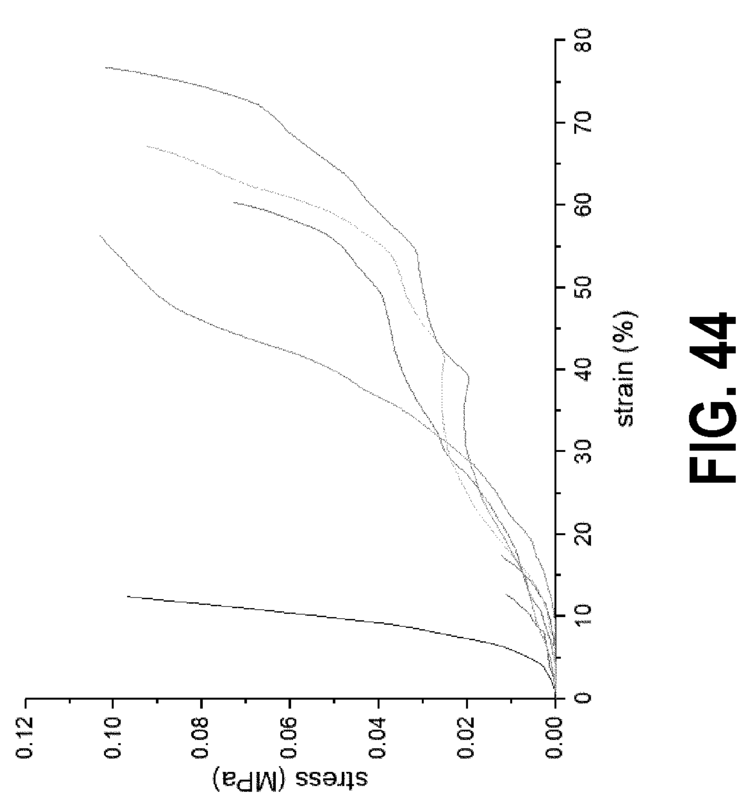
FIG. 44 shows raw stress strain curves for compressed SMP foams, compressed at 5 mm×$min^{-1}$ to yield using the DMA at room temperature and ambient atmosphere.

Polyurethane-based SMP foams have demonstrated a range of strain recoveries, ranging from complete recovery (coupled with a thermo-solvation swelling effect) to less than 10% strain. The residual presence of alcohols in aliphatic polyurethane systems has been hypothesized to induce excess tackiness and reduce strain, and therefore volumetric, recovery. Representative compressive stress-strain plots of a variety of foams, compressed at 5 mm×$min^{-1}$ to yield using the DMA at room temperature and ambient atmosphere is shown in FIG. 12. As shown in FIG. 12, a foam formed by N Epoxide, as in an embodiment of the invention, exhibits far less strain per stress applied thereto as comparative foams. To further emphasize a utility of the invention, FIG. 13 shows photographs of representative microscopic images of the compress deformation of a BADGE-PETMP SMP foam at room temperature. Further, FIG. 42 shows raw stress strain curves for compressed SMP foams, compressed at 5 mm×$min^{-1}$ to yield using the DMA at room temperature and ambient atmosphere. FIG. 43 shows raw stress strain curves for compressed SMP foams, compressed at 5 mm×$min^{-1}$ to yield using the DMA at room temperature and ambient atmosphere. FIG. 44 shows raw stress strain curves for compressed SMP foams, compressed at 5 mm×$min^{-1}$ to yield using the DMA at room temperature and ambient atmosphere.

Figure 46:
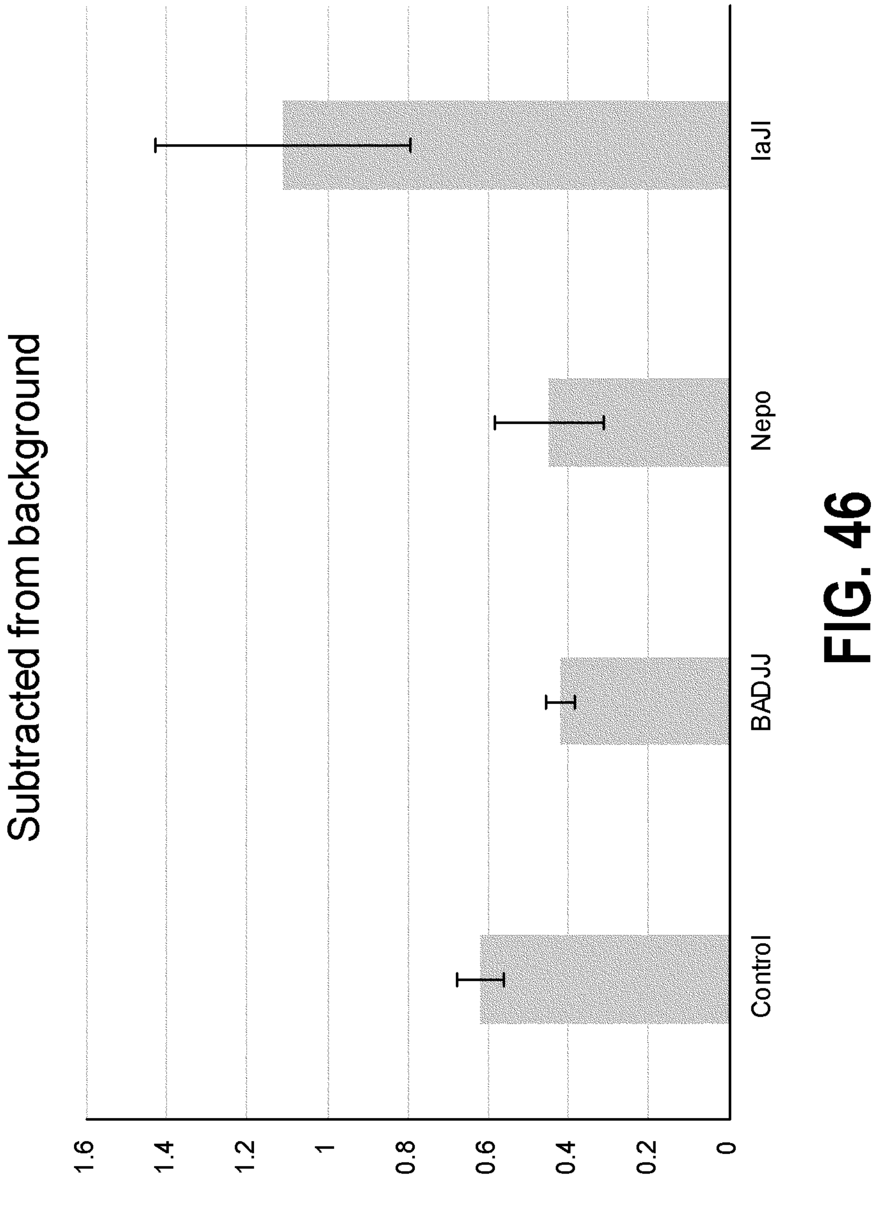
FIG. 46 shows a bar graph of four different samples of the foams comparing growth of each foam.

Furthermore, FIG. 46 shows a bar graph of four different samples of the foams. The bar graph in FIG. 46 shows that the cells are growing, confirming that they can survive as a surface compared with tissue culture polystyrene. In FIG. 46, the "control" foam is polystyrene. In the field of SMP foams, polystyrene is a common material used to make well plates and other cell culture items.

TABLE 2

Shape memory properties of SMP foams such as poly(thioethers), with strain fixation examined at ambient conditions and strain recovery examined at 30° C. and 40° C. DI $H_2O$ (n = 3)

| Species | Morphology | Strain Fixation (1 h) (%) | Strain Fixation (1 day) (%) | Strain Recovery (1 h) (%) (30° C.) | Strain Recovery (1 day) (%) (30° C.) | Strain Recovery (1 h) (%) (40° C.) | Strain Recovery (1 day) (%) (40° C.) |
|---|---|---|---|---|---|---|---|
| BADGE | Film | 99 | 99 | | | | |
| | Foam | 98 | 96 | 16 | 31 | 83 | 100 |
| N Epoxide | Film | 99 | 99 | | | | |
| | Foam | 96 | 92 | | | | |
| IPDI | Film | 99 | 99 | | | | |
| Epoxide | Foam | 98 | 97 | | | | |

TABLE 3

Shape memory properties of SMP poly(thioethers), with strain fixation examined at ambient conditions and strain recovery examined at 30° C. (columns 4th and 3rd from the right) and 100° C. DI $H_2O$ (columns 2nd and 1st from the right). (n = 3)

| Species | Morphology | Strain Fixation (1 h) (%) | Strain Fixation (1 day) (%) | Strain Recovery (1 h) (%) | Strain Recovery (1 day) (%) | Strain Recovery (1 h) (%) | Strain Recovery (1 day) (%) |
|---|---|---|---|---|---|---|---|
| BADGE | Film | 99 | 99 | <5% | <5% | 100 | 100 |
| | Foam | 98 | 96 | 6.1 | 9.4 | 100 | 100 |
| N | Film | 99 | 99 | <5% | <5% | 82 | 94 |
| Epoxide | Foam | 96 | 92 | <5% | <5% | 100 | 100 |
| IPDI | Film | 99 | 99 | <5% | <5% | 100 | 100 |
| Epoxide | Foam | 98 | 97 | <5% | <5% | 100 | 100 |

TABLE 4

Thermomechanical properties of porous SMP foams tested in compression at ambient conditions, 5 mm × $min^{-1}$ to yield, n = 7.

| Species | Elastic Modulus (kPa) | Stress at Failure (kPa) | Ultimate Stress (N × $mm^2$) | Stress at Yield (kPa) | Strain at Failure (%) | Stress at Yield (%) |
|---|---|---|---|---|---|---|
| BADGE | 1.171 ± 0.44 | 65.271 ± 22.30 | 75.143 ± 41.36 | 26.671 ± 5.25 | 61.171 ± 11.47 | 25.340 ± 7.03 |
| N Epoxide | 3.786 ± 3.26 | 97.986 ± 21.31 | 55.957 ± 26.50 | 34.414 ± 18.17 | 28.268 ± 13.72 | 14.079 ± 7.62 |
| IPDI Epoxide | 1.171 ± 0.72 | 70.271 ± 38.00 | 60.671 ± 39.57 | 22.223 ± 11.60 | 43.206 ± 25.92 | 23.165 ± 14.36 |

TABLE 5

Thermomechanical properties of SMP films (non-porous) and SMP porous foams measured by DMA. (n = 3)

| Species | Tan δ onset (° C.) | Tan δ peak (° C.) | Tan δ FWHM (° C.) | E* (25° C.) (MPa) | E' inflection point (° C.) | E' inflection point (MPa) | E'' peak (° C.) | E'' inflection point (MPa) |
|---|---|---|---|---|---|---|---|---|
| BADGE | 47.6 | 73.6 | 16.3 | 1661± | 56.8 | 702.1 | 55.4 | 185.0 |
| N epoxide | 48.6 | 71.5 | 38.1 | 2172± | 56.7 | 1079 | 58.6 | 243.1 |
| IPDI epoxide | 61.4 | 105.2 | 35.3 | 538 | 75.4 | 179 | 75.6 | 74.8 |

Figure 14:
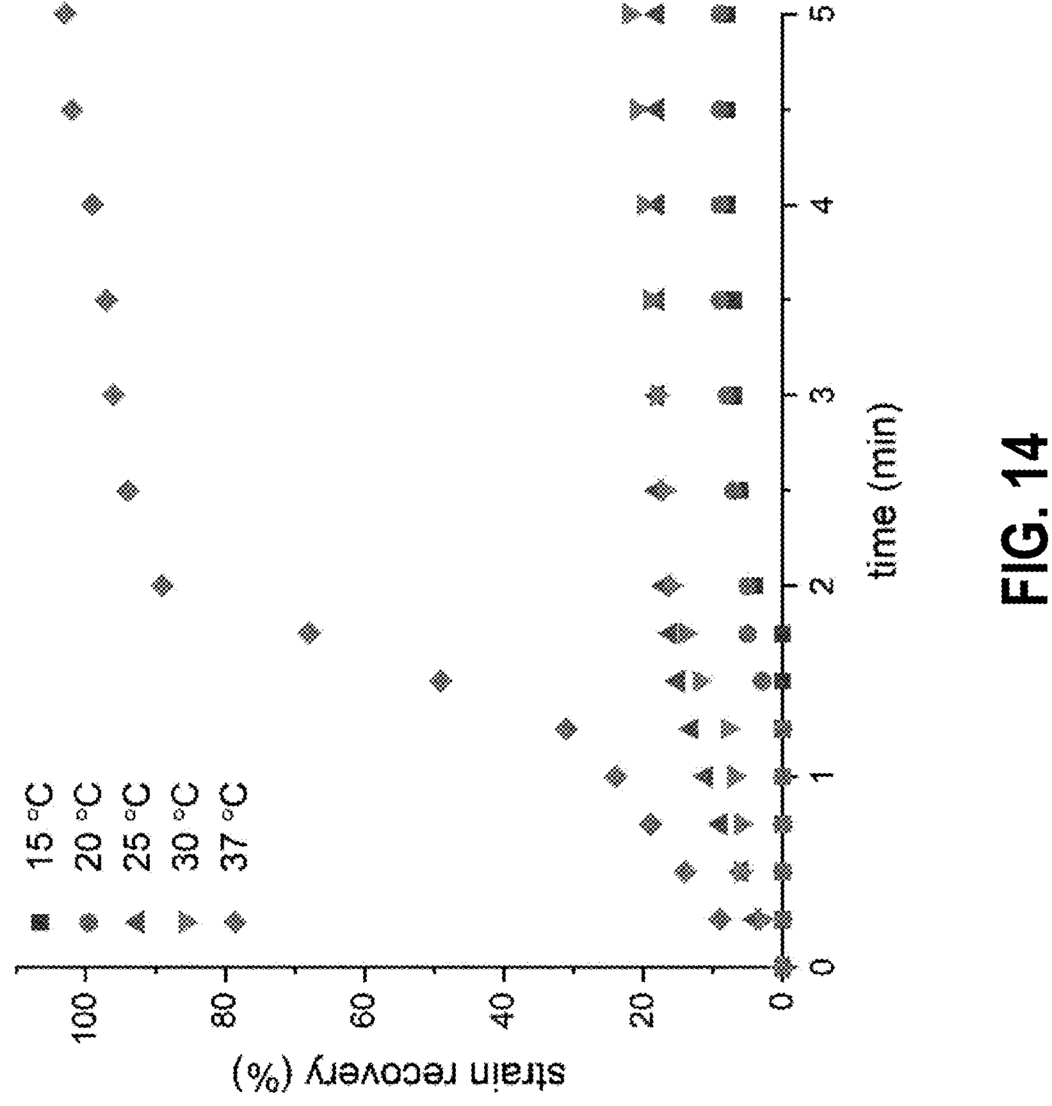
FIG. 14 shows strain recovery of BADGE foam in DI $H_2O$ at different temperatures and the strain recovery behaviors for the different SMP formulations at 37° C. in DI $H_2O$.
Figure 45:
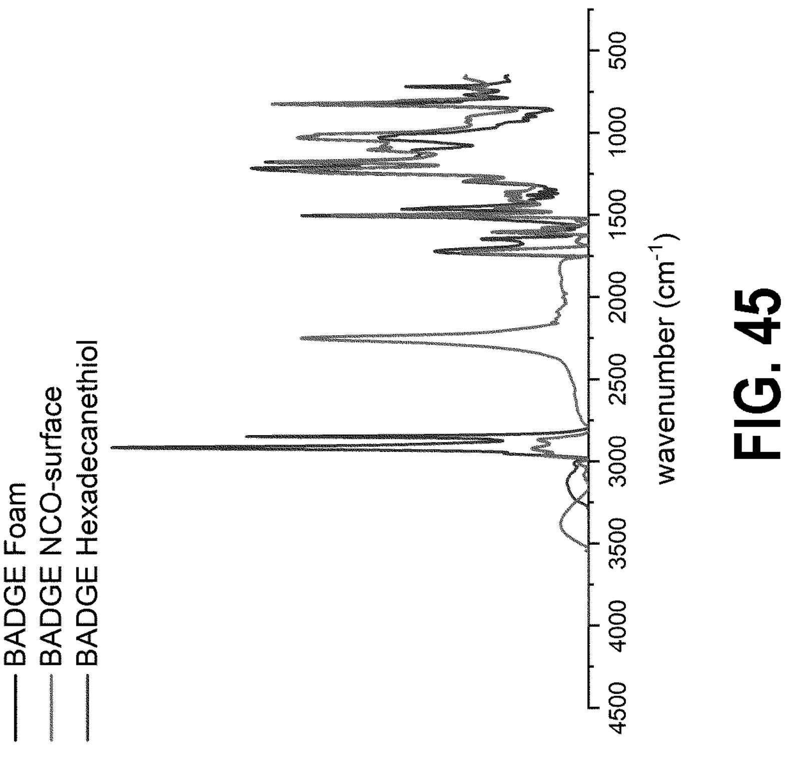
FIG. 45 shows FT-IR spectra of BADGE foams after cleaning, after 6 h incubation in IPDI solution (with peak at about 2300 nm), and after 6 h incubation in hexadecanethiol solution (with 1 wt % DBU for a catalyst)(with large peak at about 2800 nm).

The shape memory response of the foams in DI $H_2O$ was a thermo-solvated plasticization-driven strain recovery mechanism. At temperatures below the plasticized $T_g$, less than 20% recovery was found. Data showing strain recovery of BADGE foam in DI $H_2O$ at different temperatures and the strain recovery behaviors for different SMP formulations according to the invention at 37° C. in DI $H_2O$ is shown in FIG. 14. Furthermore, FIG. 45 shows FT-IR spectra of BADGE foams after cleaning, after 6 h incubation in IPDI solution (with peak at about 2300 nm), and after 6 h incubation in hexadecanethiol solution (with 1 wt % DBU for a catalyst)(with large peak at about 2800 nm).

The shape memory response of the foam was also examined to determine if pore orientation impacted the response (without solvent-induced swelling) by compressing sections along the foaming axis (z-axis), as well as in the xy plane. The recoverable strain was not impacted, with compression in any dimension providing for approximately 100% strain fixation and 100% strain recovery (with greater than 100% volumetric recovery possible in solvent).

Material Stability

The degradation of foams has been widely reported, especially in biomaterials, with degradable formulations displaying often exaggerated behavior because of the greatly increased surface area-to-volume ratios.

Mechanistically, all of the foams contain thioether linkages, which will oxidize, thereby scavenging hydroxyl radical concentrations. In the BADGE and N Epoxide foams, reduces the subsequent chain cleavage which results from the corresponding oxidation-reduction reactions of the ether and tertiary amine linkages, respectively. In the IPDI Epoxide foams, oxidation of the urethanes linkages was previously revealed in similar conditions to be highly unfavored and slow.

Hydrolytically, the IPDI Epoxide materials displayed the most rapid degradation of any examined composition. Within 18 h of immersion in 1 M NaOH at ° C., only 5% of mass is remaining. The N epoxide materials, while more hydrolytically stable relative to the aliphatic foams, still displayed rapid gravimetric changes in this environment. By comparison, BADGE foams displayed swelling.

Post-Foaming Modifications

Figure 15:
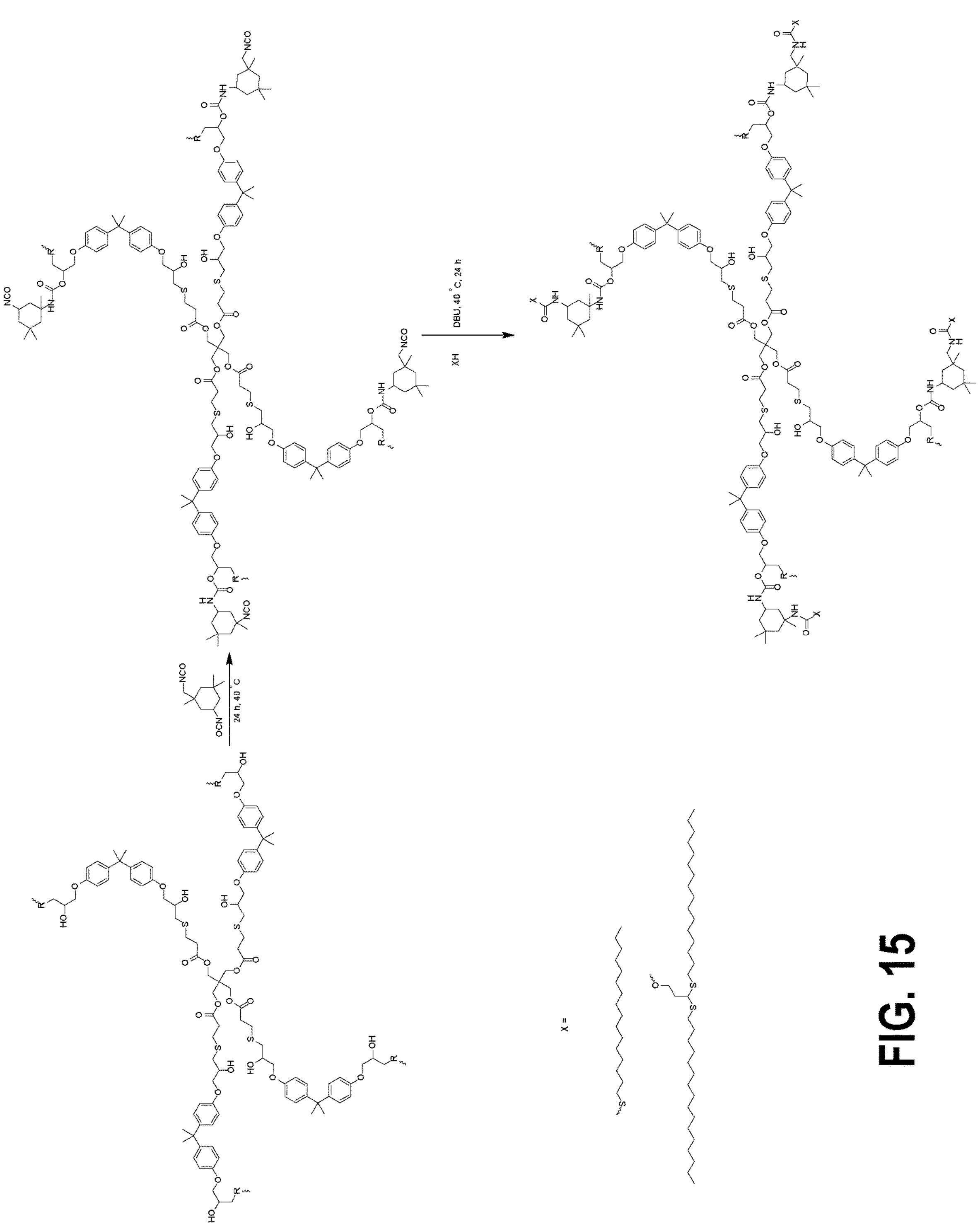
FIG. 15 shows post-foaming functionalization of the BADGE network repeat unit, displaying idealized functionalization using the reaction of the diisocyanate IPDI with residual alcohols in step 1, followed by formation of a urethane or thiourethane linkage in a subsequent step.

Based upon the material stability studies, and assuming an environmental application, the BADGE foams were selected for post-foaming modifications as the most likely translational candidate with regards to oil remediation and collection after spills. This application, which ideally encompasses a combination of shape recovery in lipophilic or hydrophilic solvents preferably to water or alcohols as well as a high upper swelling limit, would see materials deployed in aqueous environments similar to polyethylene sheeting after an oil spill. The foams would then be used to collect residual and surface oil, thereby cleaning the local environment more rapidly, using a technique with scalable potential. However, the residual alcohol groups would be likely a limitation for the collection of large amounts of oil, and post-foaming functionalizations would likely be needed. At least one technique to achieve such modifications includes the use of designer nanoparticles. A reaction formula showing the reaction of post-foaming functionalization of a BADGE SMP foam is shown in FIG. 15. As shown in FIG. 15, post-foaming functionalization of the BADGE network repeat unit are shown. Idealized functionalization is displayed using the reaction of diisocyanate IPDI with residual alcohols, followed by formation of a urethane or thiourethane linkage in a subsequent step.

Reclamation of oil was first examined using the original SMP foams, immersed in a 1:1 volumetric amount of hydraulic oil and water at room temperature. The mass of the compress, shape set foam was determined at 6 h after immersion, and the majority species of the taken up material was determined volumetrically as well. Based on materials stability and mechanical properties (specifically the final brittleness), N Epoxide was excluded from this study. IPDI Epoxide materials were found to take up primarily water, with approximate 3× mass $H_2O$ taken by the material, a trend which was repeated at 30° C. and ultimately resulted in expansion of the material. Interestingly, the IPDI-derived materials floated primarily in the water layer for the duration of the studies.

Figure 16:
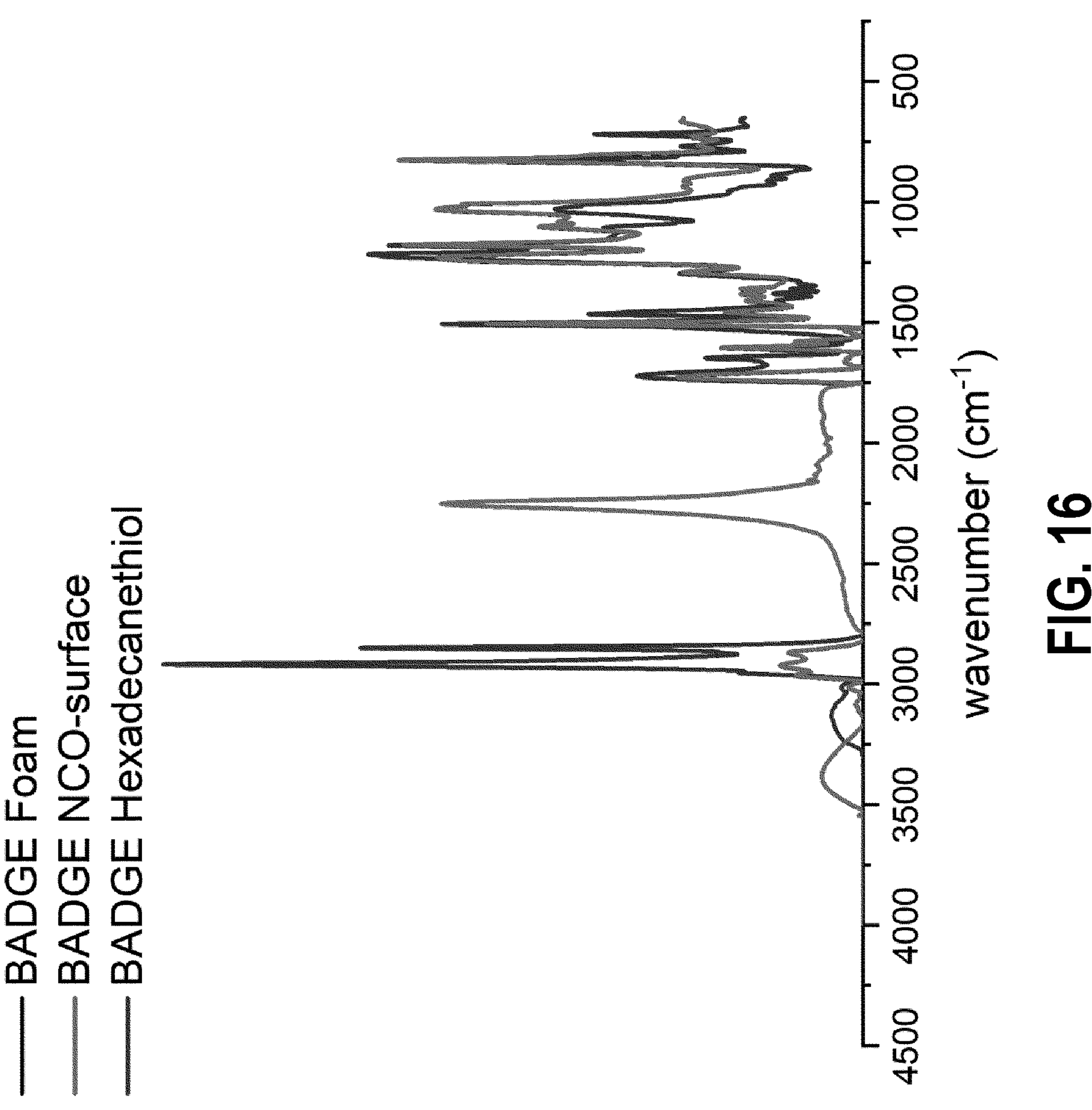
FIG. 16 shows FT-IR spectra of BADGE foams after cleaning (dark), after 6 h incubation in IPDI solution (light), and after 6 h incubation in hexadecanethiol solution (with 1 wt % DBU for a catalyst).

Importantly, the average volumetric recovery of the samples was low. It was hypothesized that part of mechanism for this would be the residual alcohols formed from the epoxide ring opening, leaving a number of alcohol moieties which would initially reduce the lipophilicity but also could be leveraged to enhance it with subsequent functionalization. IPDI was selected as a common, readily available, and reactive surface modifier, and SMP foam cubes were incubated in a 80 wt % solution of IPDI and tetrahydrofuran (THF) over night, followed by a 5 min wash in THF. The residual isocyanate groups on the foam surface, confirmed by FT-IR (FIG. 16), could be further exploited by immersing the foam substrate in solutions containing amines, alcohols, thiols, etc. In this instance, hexadecanethiol and a propargyl alcohol derivative which had first been bifunctionalized using two measures of hexadecanethiol were respectively examined. Specifically, FIG. 16 shows FT-IR spectra of BADGE foams after cleaning, after 6 h incubation in IPDI solution, and after 6 h incubation in hexadecanethiol solution (with 1 wt % DBU for a catalyst).

As stated, the functionalization was monitored by FT-IR, with the BADGE SMP foams displaying characteristics bands for the thioether, alcohol groups and carbonyl groups. After immersion in the isocyanate solution, the characteristic isocyanate band was found at 2286 to 2229 $cm^{-1}$, and the subsequent shift from 1727 to 1721 $cm^{-1}$ indicated the formation of the urethane linkage, denoted that tethering of the IPDI molecules onto the surface of the foams. Further treatment using hexadecanethiol demonstrated the formation of a new peak at 1646 $cm^{-1}$, likely due to the altered orientation of the hydrogen bonding in the new thiourethane linkage that is formed by reaction with the surface isocyanate groups. Importantly, the isocyanate peak was consumed after 24 h in the second solution.

Collection of Oil

Figures 17, 18:
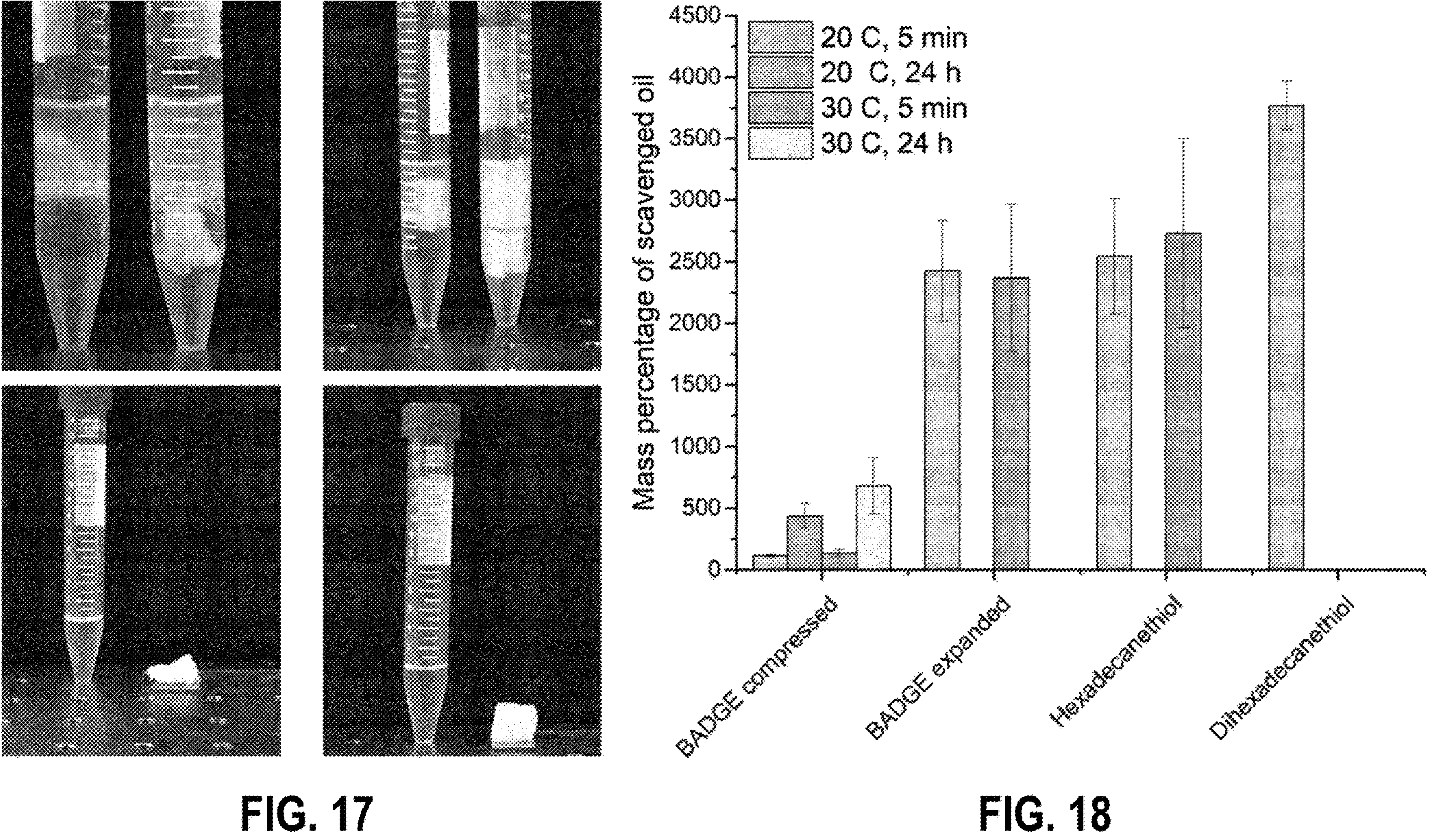
FIG. 17 shows the mass of collected oil from BADGE SMP foams in 1:1 layered mixture of hydraulic oil and water at 20° C. and 30° C. (n=3).
FIG. 18 shows a bar graph showing the mass of collected oil from BADGE SMP foams in 1:1 layered mixture of hydraulic oil and water at 20° C. and 30° C. (n=3).

The foams described herein, such as poly(β-thioether), can be used to collect oil from the environment. The naturally occurring oil often needs to be harvested from spaces where existing technologies are ineffective, destructive, or harmful to the environment. At least due to the rapid foaming, tunable expansion, scavenging properties of hydrophobic liquids, and potential for subsequent functionalization after foaming at least to change the hydrophobicity of the foams, the foams described herein may be used to collect oil or other natural resources in a safe, effective, and healthy way by absorbing oil to which it is exposed, particularly because the poly(β-thioether) is capable of tunable expansion and scavenging properties to absorb hydrophobic liquids, such as oil and/or crude oil. The foam, having absorbed oil therein, may be collected and subsequently treated to harvest the oil from the foam. This method of harvesting may replace otherwise hazardous procedures such as fracking, and has the benefit of avoiding the detrimental environmental effects. Moreover, the high porosity of the shape memory polymer foams described herein lead to vast surface area upon which the crude oil can be absorbed. A qualitative example of oil collection is shown in FIG. 17. In FIG. 17, the photographs shown are a compressed BADGE foam (left) and IPDI Epoxide foam (right) at 20° C., and 30° C. (B), and FIG. 18 is an accompanying quantitative plot of various SMP foams performances of scavenging oil. Specifically, FIG. 18 shows the mass percentage of scavenged oil at various temperatures and times of exposure for a variety of SMP foams, such as BADGE compressed, BADGE expanded, hexadecanethiol, and dihexadecanethiol foams according to the invention. As further explanation, FIG. 18 shows a bar graph showing the mass of collected oil from BADGE SMP foams in 1:1 layered mixture of hydraulic oil and water at 20° C. and 30° C. (n=3).

Blood Flow Stability and Breast Implant Applications

The foams described herein, such as poly(β-thioether), have myriad applications, several of which include medical applications. Particularly, at least due to the rapid foaming, tunable expansion, scavenging properties of hydrophobic liquids, and potential for subsequent functionalization after foaming at least to change the hydrophobicity of the foams, the foams described herein may be used to stabilize blood flow. For example, medical patients that have suffered a stroke or aneurysm occlusion often have hydrophobic material in their blood that must be removed to restore stability of the patient's blood flow, or expanding the diameter of blood vessels to allow for the stabilization of blood flow beyond obstructions in the blood vessels.

Furthermore, the foams described herein, such as poly(β-thioether), may be used in breast implant applications. For example, a housing material acceptable to be implanted in a human breast, for cosmetic or medical purposes, may encase the foams described herein and may be particularly sized per the need or desire of the patient at least because the foaming is a tunable expansion.

3-D Printing

The foams described herein may be formed from a 3-D printer. The epoxide and thiol monomers in the presence of an organobase. Particularly, the shape memory polymer foams described herein may be formed by reacting pentaerythritoltetra(3-mercaptopropionate) and bisphenol A diglycidyl ether in the presence of 1,8-diazabicyclo[5.4.0]undec-7-ene to form a filament. The filament may be printed using a 3-D printer to form desired structures.

Oil Remediation and Cost Analysis

The BADGE foams were then studied alongside the IPDI foams for potential in scavenging surface oil slicks after spills. Modern techniques that have been utilized for this problem have focused on polyethylene sheeting, however a number of smaller, less economically-viable solutions have been explored with differing effects. Polymeric foams have emerged on the forefront of possible technologies used to combat oil spills, and to aid in the remediation of otherwise tainted environments. For example, polyHIPEs of polystyrene, a surfactant and $SiO_2$ microparticles have been demonstrated to be utilized in producing highly porous materials (0.186 to 0.036 g $cm^3$ reported), but the oil recovery never exceeded the mass of the composite material, even when using ideal organic solvents. Similarly, polypropylene foams containing polytetrafluoroethylene nanoparticles produced through extrusion and subsequent super critical carbon dioxide resulted in approximately 10 μm pores and oil absorptions of nearly 5× the original mass of the polymer (8× for organic solvents), but unfortunately material density and porosity were not reported. Similarly, polypropylene foams containing polytetrafluoroethylene nanoparticles produced through extrusion and subsequent super critical carbon dioxide resulted in approximately 10 μm pores and oil absorptions of nearly 5× the original mass of the polymer (8× for organic solvents), but unfortunately material density and porosity were not reported.

Figure 50:
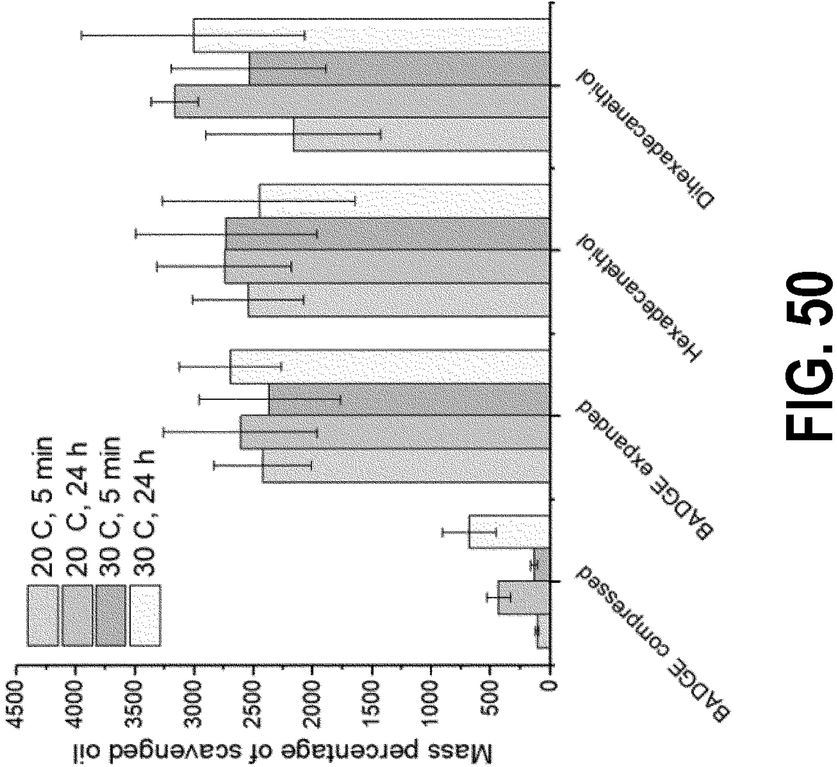
FIG. 50 shows a bar graph of the effectiveness of oil scavenging of various foams. The various foams include compressed BADGE foam, expanded BADGE foam, Hexadecacantethiol, and dihexadecanethiol.
Figure 49:
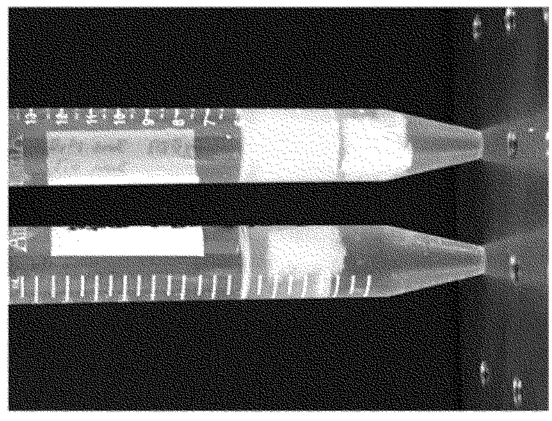
FIG. 49 shows a representative image of compressed BADGE foam (left in each image) and IPDI Epoxide foam (right in each image) at 20° C. (left image), and 30° C. (right image). The mass of collected oil from BADGE SMP foams in 1:1 layered mixture of hydraulic oil and water at 20° C. and 30° C. (n=3).
Figure 49:
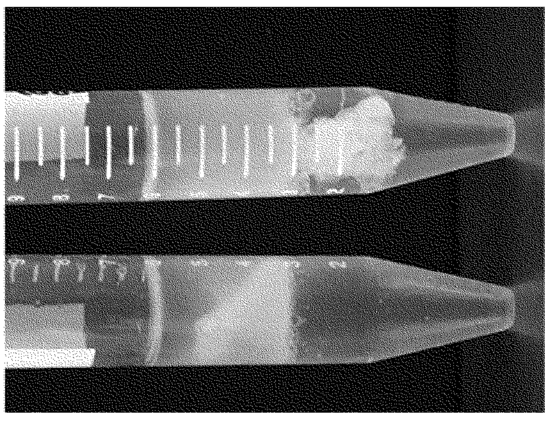

Images of compressed BADGE and IPDI Epoxide foams are shown in FIG. 49. Specifically, FIG. 49 shows a representative image of compressed BADGE foam (left in each image) and IPDI Epoxide foam (right in each image) at 20° C. (left image), and 30° C. (right image). The mass of collected oil from BADGE SMP foams in 1:1 layered mixture of hydraulic oil and water at 20° C. and 30° C. (n=3). The quantitative results of oil reclamation capabilities of various foams is represented in FIG. 50. Specifically, FIG. 50 shows a bar graph of the effectiveness of oil scavenging of various foams. The various foams include compressed BADGE foam, expanded BADGE foam, Hexadecacantethiol, and dihexadecanethiol.

Figure 52:
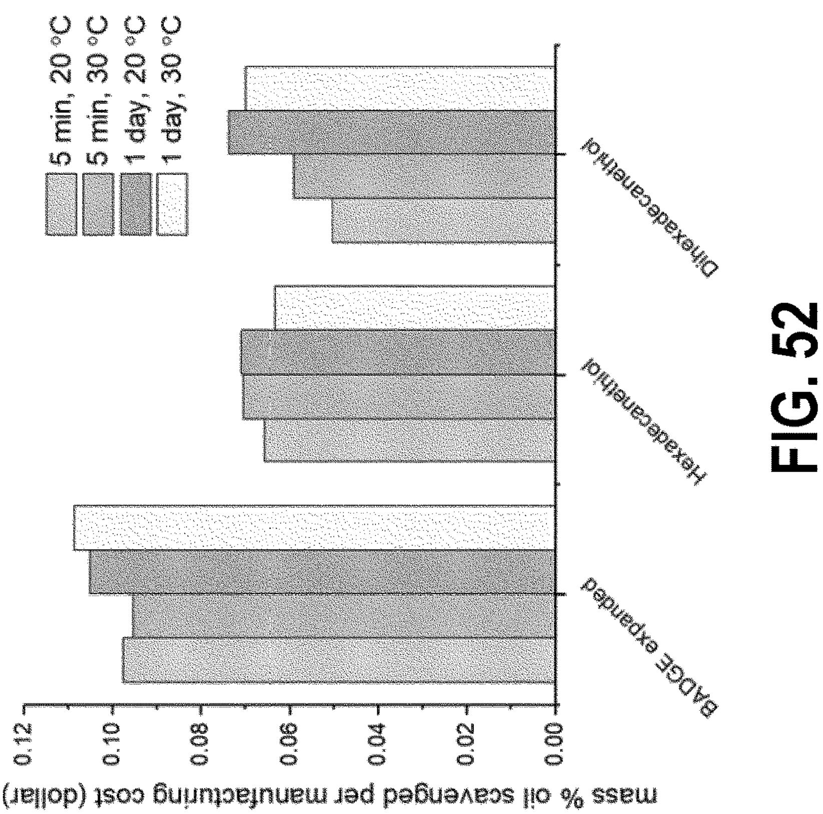
FIG. 52 shows a bar graph of the mass percentage of oil scavenged per manufacturing cost of various foams. The various foams include expanded BADGE foam, Hexadecacantethiol, and dihexadecanethiol.
Figure 51:
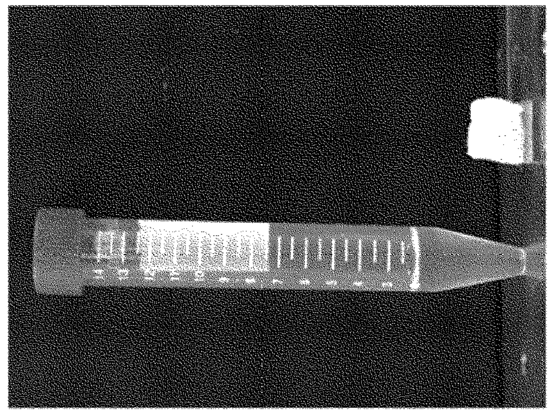
FIG. 51 shows a representative image of compressed BADGE foam (left) and IPDI Epoxide foam (right) at 20° C. (A), and 30° C. (B). The mass of collected oil from BADGE SMP foams in 1:1 layered mixture of hydraulic oil and water at 20° C. and 30° C. (n=3).
Figure 51:
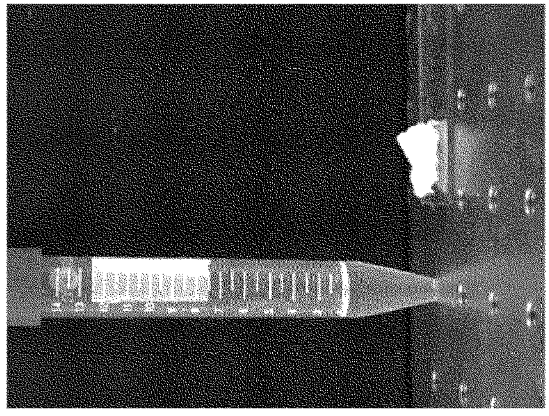

Additional images of compressed foams is shown in FIG. 51. FIG. 51 shows a representative image of compressed BADGE foam (left) and IPDI Epoxide foam (right) at 20° C. (A), and 30° C. (B). The mass of collected oil from BADGE SMP foams in 1:1 layered mixture of hydraulic oil and water at 20° C. and 30° C. (n=3). The quantitative results of oil reclamation capabilities of various foams is represented in FIG. 52. FIG. 52 shows a bar graph of the mass percentage of oil scavenged per manufacturing cost of various foams. The various foams include expanded BADGE foam, Hexadecacantethiol, and dihexadecanethiol.

The use of the BADGE foams at 20° C. was found to allow for scavenging up to 5× the foam mass in the compressed foams (SMPs in the temporary, secondary shape which are too far below the $T_g$ to expand), and this was dramatically increased to nearly 25× the mass in the expanded BADGE materials. In the compressed samples, longer exposure times resulted in greater uptake of remedial oil, which was not significantly found in the expanded BADGE samples. Increased temperature resulted in greater uptake, likely due to the greater mobility of the polymer network which would allow for more swelling, even if the majority of the material is still thermally constrained. However, the temperature at which the materials are tested does not seem to influence the uptake of oil as much as the accessible porosity of the material.

Surface functionalization using the hexadecanethiol was found to provide marginal increases in the uptake of oil, while the dihexadecanethiol modification displayed more significant increases. However, as demonstrated by the raw comparisons, the porous nature of the materials themselves seem to be the dominating factor compared with surface functionalizations, as confirmed by cost analysis.

Analysis of the return on scavenged oil was done for 1 kg and 100 kg of material, assessing the efficiency of the methods. The unmodified BADGE foams display the highest efficiency by this analysis, which excludes processing time and worker-time costs; including these costs, which are difficult to accurately calculate, would only further improve the BADGE foam.

The original foam was found to yield approximately 10% of its mass in recovered oil from the oil:water mixture when accounting for the manufacturing cost, while the hexadecanethiol and dihexadecanethiol modified materials were below 8%, regardless of the immersion time or examined temperatures. This is especially insightful, as it means in the case of environmental remediation after a spill, time does not need to be wasted by performing multi-step modifications and processing for the raw material. Rather, the raw material seems best suited for the performance and can be rapidly developed then deployed.

Another important factor to consider here is the water uptake of the materials, as both the oil reclamation and the TGA studies indicated the presence of water in the materials, although this appears to be very low amounts and would be consistent with a hydroxyl-containing porous material. A dried material, while providing a higher efficiency for such testing, would not be a feasible test article for oil reclamation on a large scale due to the impracticalities of maintaining a water-free environment for storage and transportation on the scales necessary for environmental remediation. Additionally, these assessments do not fully encompass the reclamation process involving isolating pure oil and reusing it. These types of studies will be necessary for more application-specific testing. Finally, material degradation with regards to cost analysis and the energy needs for full recycling or decomposition are not included in this evaluation, and will be factors of consideration moving forward to greater scales of production and assessment.

Conclusions

In conclusion, we present the development of low density, high porosity shape memory poly(β-thioether) foams in a rapid reaction of economically-scalable epoxide and thiol monomers in the presence of the organobase DBU. The rapid reaction allows for the production of controlled pore morphology and density in SMP foams, with 5 min required from the addition of monomers to the final material product. The use of a BPA derivative, a tertiary amine-containing epoxide, and an epoxide with two urethane linkages demonstrated the tunability of thermomechanical properties and biostability. The formation of the poly(β-hydroxythioether) network, which produces alcohol groups during the epoxide ring opening, was then leveraged for post-foaming functionalization using first isophorone diisocyanate followed by either hexadecanethiol or a di-hexadecanethiol monomer to compare both the efficiencies and the idealized economics of these materials in oil scavenging using hydraulic motor oil. While the porous materials are suitable for recovering large masses and volumes of oils selectively from oil:water mixtures, ultimately the unmodified BADGE materials demonstrated the most economic route towards oil recovery with regards to both the recoverable oil from polluted environments, and the cost effectiveness of such a method, providing a feasible route to aid in environmental recovery plans globally.

Example 2

General: Chemicals were purchased and used without purification from TCI® (having a place of business in Tokyo, Japan).

Foam Synthesis: Polymer foam was produced by adding the epoxide monomer, PETMP, acetone and the organobase catalyst into a single container with salt. For the Neopentyl foam synthesis, Neopentyl glycol diglycidyl ether monomer was added to a beaker with stoichiometric amounts of PETMP and mixed until the reagents were homogeneous. A small amount of DBU was added into the beaker containing Neopentyl and mixed for approximately 30 s before being poured into the container containing salt. The mixture was placed on a room temperature surface and allowed to completely settle around the salt particles for. The foam solidified over a 10 min period and was placed in a 120° C. oven for 12 h to carry the reaction to completion. Following the curing process, the foam was removed and cut into cubes and placed in a heated (90° C.) beaker with water. The foams were left in the beaker for 72 h with a magnetic stir bar to keep the water oscillating, replacing the water every 24 h. After washing, the foams were dried at 50° C. overnight using the Across International AT09-UL Vacuum Drying Oven (Across International®, having a place of business in Livingston, NJ) and used for subsequent characterizations.

Rheology Characterization: Stoichiometric amounts of PETMP and the corresponding epoxide were first mixed together and then added to the parallel plate geometry on the rheometer (500 μm) at room temperature, at which time the samples were subjected to uniaxial rotation and oscillatory shears. Subsequent testing of the reaction kinetics was done including 0.1 wt % DBU, added immediately prior to shearing. These kinetic studies were conducted over 5000 s, measuring storage and loss moduli using oscillatory testing at 1 Hz frequency and 1% oscillatory rotation.

Dynamic Mechanical Analysis: The mechanical properties of the foams were analyzed using a TA Instruments DMA 800 in compression mode. 1 $cm^3$ foam cubes were centered in the test platens and equilibrated at 25° C. and 37° C. at which the sample was compressed at 50%×$min^{-1}$ to failure. Elastic moduli, strain at failure, toughness, and ultimate stress and strain were calculated from the corresponding stress-strain curves. This test was completed both with dry and submerged foams to look at how the plasticization effects the mechanical properties. Thermal properties of the foams were characterized using the same instrument with samples incubated.

Thermal Analysis: Using differential scanning calorimetry (DSC) and thermal gravimetric analysis (TGA), the thermal transitions of foams were analyzed. DSC was used to determine the $T_g$ using a TA Instruments Q200 equipped with TA Refrigerated Cooling System 90 (TA Instruments, New Castle, DE). To obtain the wet $T_g$, DSC samples (approximately 10 mg) were placed in hot water (approximately 90° C.) for 10 minutes. Samples were taken out and squeezed with a paper towel to remove any excess water. Samples were then sealed in a Hermetic Tzero pan with a small hole poked in the lid before being heated from −90° C. to 200° C. at 10° C.x$min^{-1}$. Using TA Analysis software (TA Instruments®, having a place of business in New Castle, DE, USA), the half-height transition of the DSC thermogram was determined as the $T_g$. A TA Instruments SDT Q600 (TA Instruments®, having a place of business in New Castle, DE, USA) was used to determine the thermal decomposition temperature (TD), characterized as the point of 5% mass loss. Samples were isothermally equilibrated at 120° C. for 30 mins to remove any residual moisture before being heated to 500° C. at 30° C.xmin-, followed by rapid heating to 1000° C. at 50° C.x$min^{-1}$.

Cytocompatibility

Spin coating: The BADGE and Neopentyl mixtures were prepared by adding 10 wt % polymer to dissolve in chloroform and a small amount of the catalyst DBU. The solution was then spun onto 12 mm glass slides for 10 secs at 50 RPM and another 10 secs at 110 RPM using a KW-4A spin coater. Once the slides were spin coated they were placed in an oven at 120° C. for 24 hours to allow the foam to cure.

Cell Culture and Proliferation: Raw 264.7 cells were cultured in Dulbecco's modified eagle'e medium (DMEM) growth media supplemented with 10% fetal bovine serum (FBS) and 1% penicillin-streptomycin solution. Cells were kept in a humidified 37° C. incubator with a 5% CO2 atmosphere before being seeded onto the polymer spin coated slides. To prepare for the cyto-compatibility study, the spin coated slides were immersed in isopropyl alcohol (IPA) for 10 mins, removed and repeated 4-5 times. After the last rinse, IPA was removed from the slides and replaced with 70% ethanol for 15 min, followed by exposure to UV light for 20 min. RAW 264.7 cells were seeded at a density of 10000 cells/mL in the respective growth media. A 3D study was conducted by cutting the foam into a 10 mm disc with a height of 3-4 mm. These foam samples were cleaned by soaking in 200 mL of water at 90° C. for 48 hours, changing the water every 12 hours. Next the foams were rinsed with IPA the same way the spin coated slides were. RAW 264.7 cells were seeded at a density of 20000 cell/mL in their respective growth media. Using CellTiter 96 AQueous® one solution cell proliferation assay (MTS), cell viability was determined by absorbance measurements obtained using a Synergy HTX® multi-mode microplate reader from Biotek® at 490 nm. These measurements were taken on day 1, day 3, day 5, and day 7 for the 2D study and days 2, 4, 7, 10, 14, 17, 21, 25, and 30 for the 3D study allowing for the cells to integrate into the porous sample. Invitrogen CellTracker CMAC Blue Dye® (7-amino-4-chloromethylcoumarin) was used to stain cells which were then imaged using a Nikon eclipse Ti inverted fluorescence microscope.

Results and Discussion

The thiol-epoxy "click" reaction was previously found to occur rapidly in the presence of DBU when using the BADGE monomer (bisphenol A (BPA) derivative), yielding gas-blown foams with tunable physical pore morphology. However, the use of the Neopentyl monomer (NEO) noticeably reduced the curing rate of the networks. In fact, the reduction prevented gas blown foam formation from occurring at all (foams would collapse due to the reduced mechanical properties), as noted with the rheological analysis of the BADGE and NEO thermoset networks. The BADGE network is several orders of magnitude greater in both storage and loss moduli, with a distinct difference between the two. This indicates the final materials is glassier than the NEO network, where the loss and storage moduli are approximately the same, indicating a material is close to its phase transition region. These differences in network behaviors ultimately resulted in the need for a different foaming approach, with saltleached scaffold templating selected due to its robustness, low cost, and ease of implementation.

Figure 53:
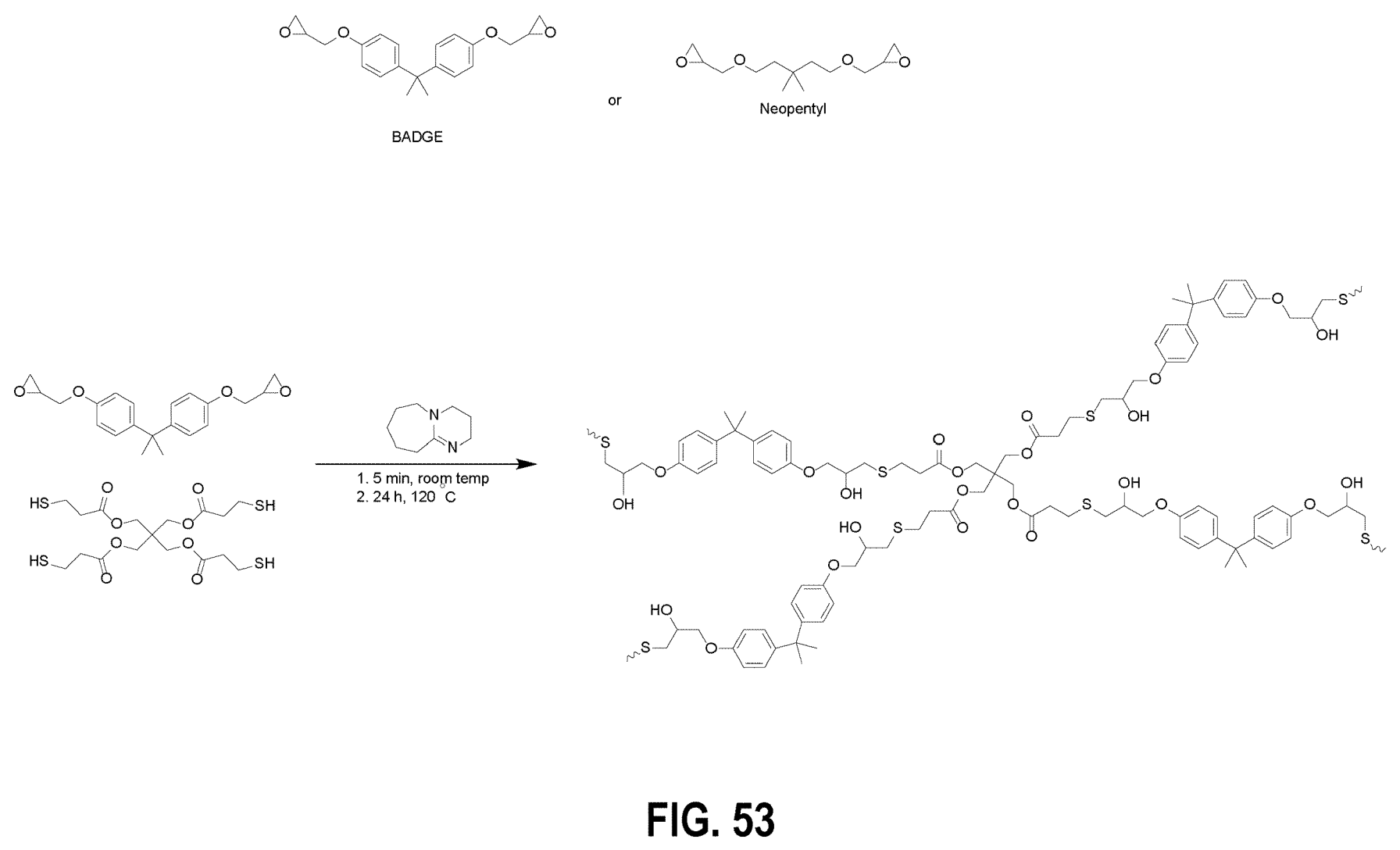
Figure 54:
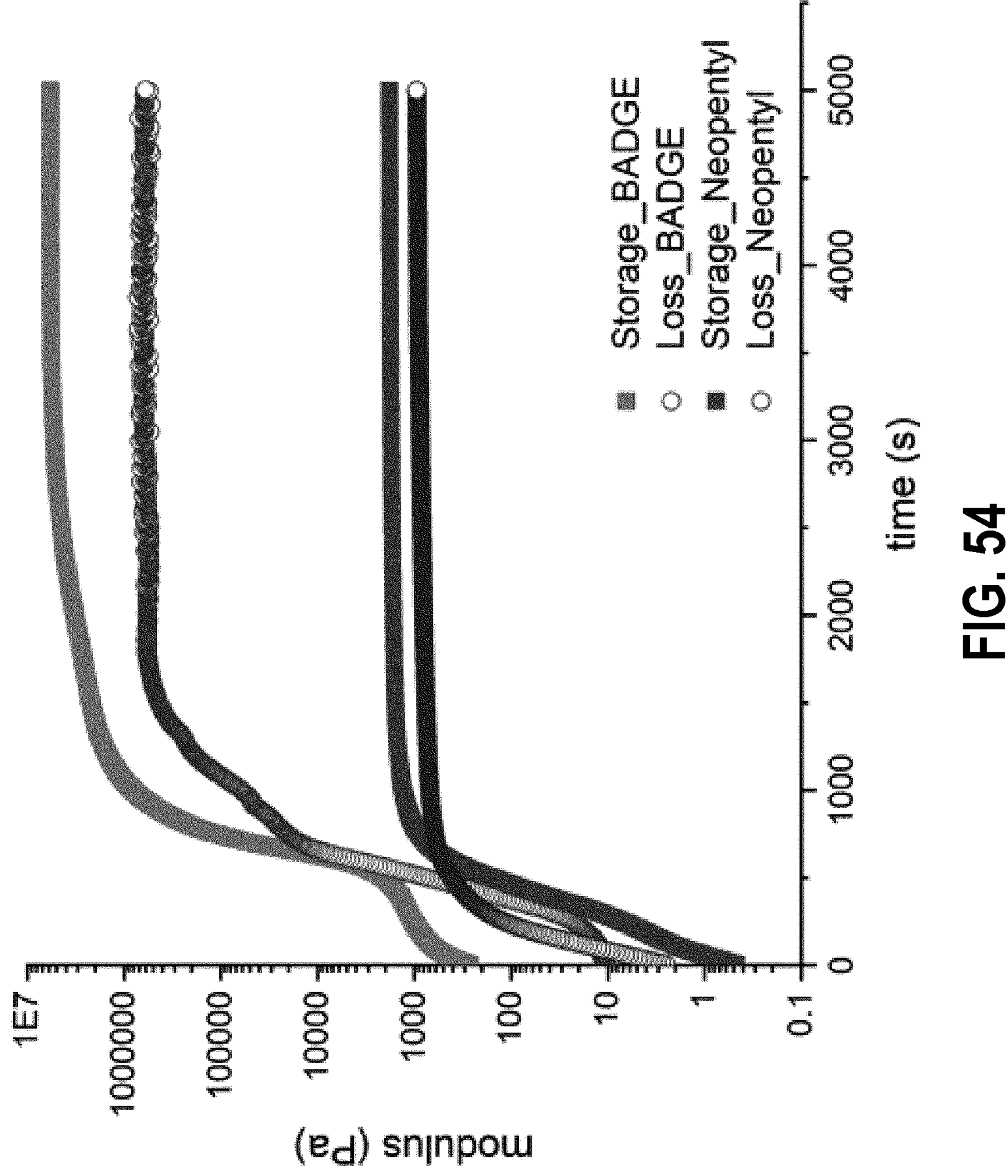
FIG. 54 shows the resultant rheological analysis of the β-hydroxythioethers produced by the formula shown in FIG. 53 as a function of cure time, including storage and loss moduli after the addition of 0.5 wt % DBU.

FIG. 53 shows an idealized reaction scheme for thiol-epoxy "click" network formation of the β-hydroxythioethers, catalyzed by the organobase DBU, with the two diepoxides of interest, being BADGE and NEO. The resultant rheological analysis of the p-hydroxythioethers as a function of cure time, including storage and loss moduli after the addition of 0.5 wt % DBU is shown in FIG. 54.

Figure 58:
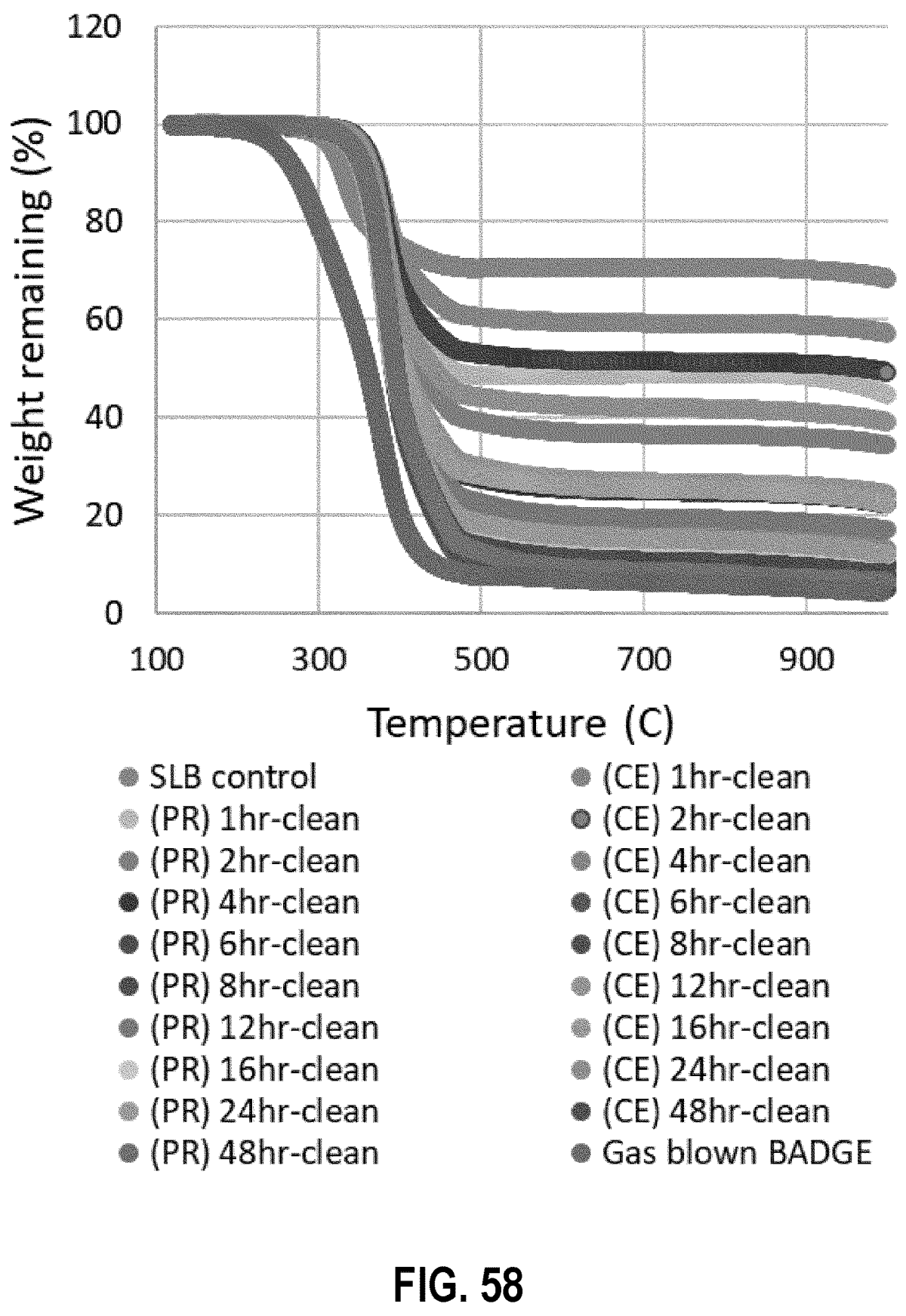

The salt template was washed from the foams with simple water extraction over a 7 day period, resulting in porous scaffolds with pore diameters less than 500 μm repeatedly, providing an alternative method of achieving such pores compared with gas-blown foaming. The removal of salt was confirmed by both SEM (visual inspection) and using TGA (gravimetric inspection)(data shown in FIGS. 56-58). Thermomechanical analysis of the foams was used to probe the impact of epoxide monomer on network rigidity, as well as the influence of environmental conditions on long-term mechanical performance. DSC and DMA were used to determine T+s of the networks, with the BADGE networks being glassier (dry $T_g$~45° C., wet $T_g$~26° C.) compared with the NEO networks (dry $T_g$~−10° C., wet $T_g$~−20° C.).

Figure 55:
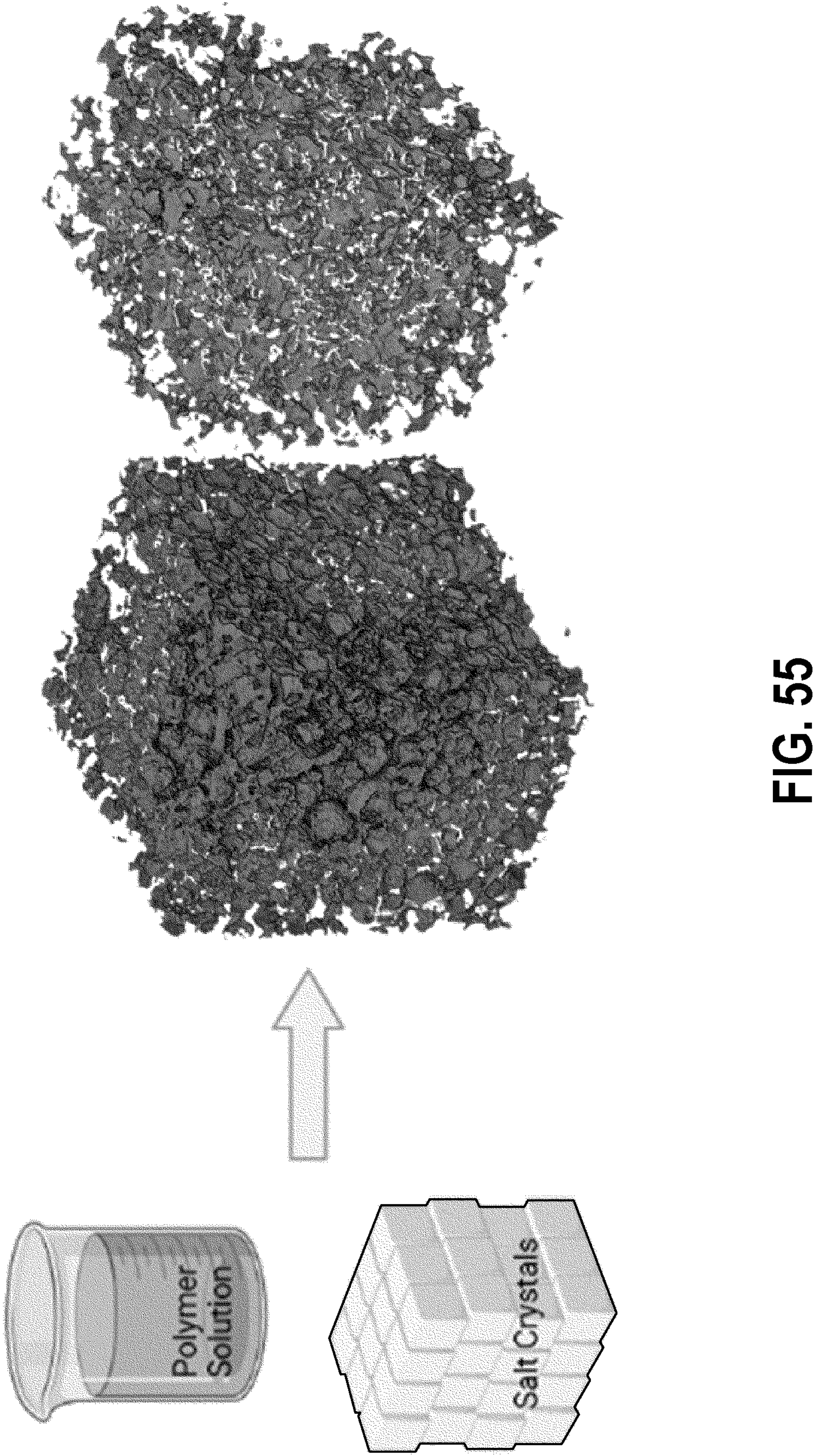
FIG. 55 shows a polymer solution including a hydroxythioether together with a salt crystal including a diepoxide to form a β-hydroxythioether foam.

Micro-CT imaging of the foams reveals no significant differences between the BADGE and NEO derived p-hydroxythioether networks (FIG. 55). The resultant pores are approximately 200 μm by this analysis, with a consistent interconnectivity of pores achieved at template loadings of greater than 60%.

Figure 56:
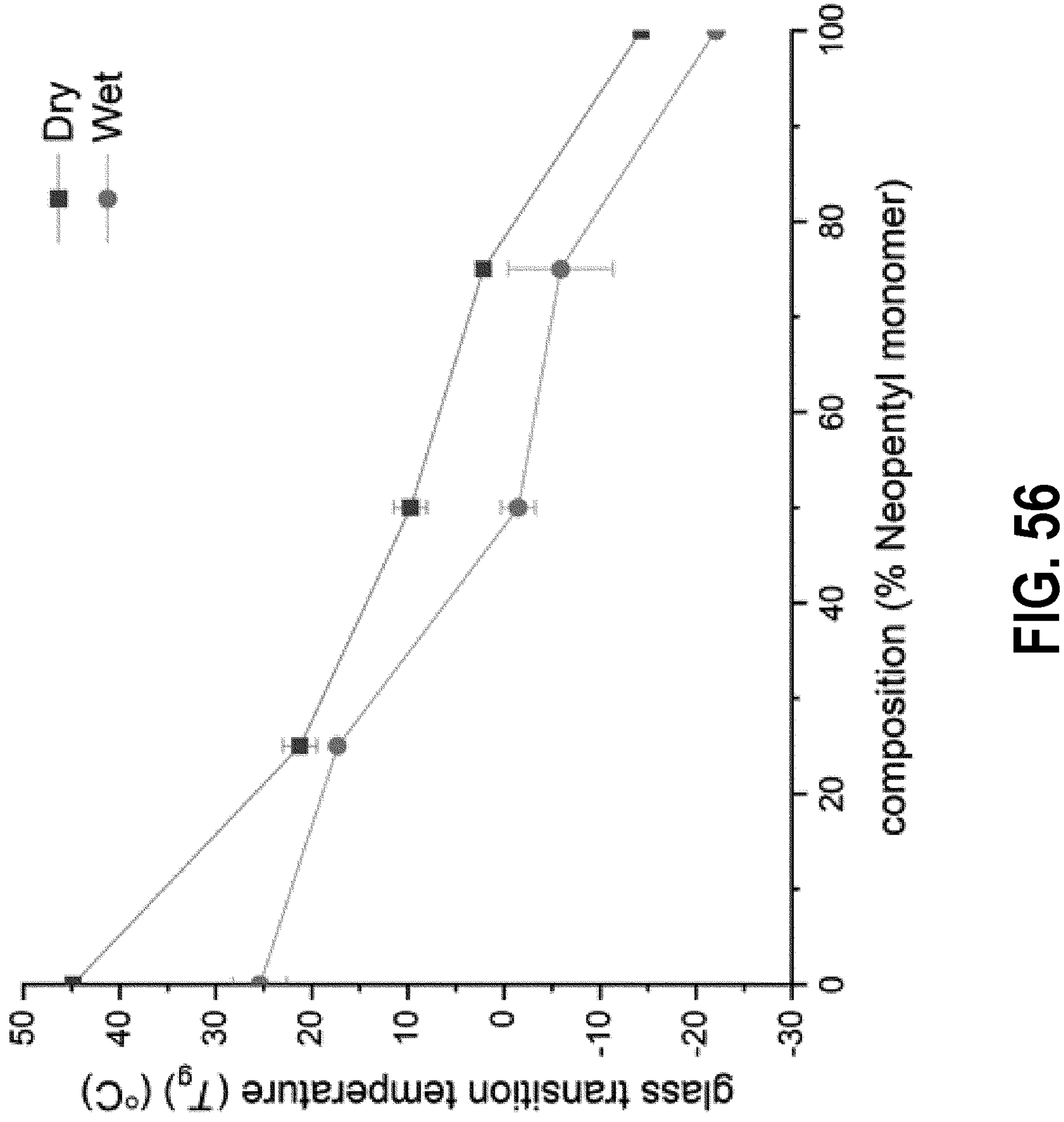
FIG. 56 shows a graph of a glass transition temperature of a foam formed in accordance with an embodiment of the invention described herein versus a Neopentyl monomer concentration of that foam. The data shown in FIG. 56 was collected keeping constant stoichiometric balance with PETMP, and is represented in the graph in accordance with both a dry foam and a plasticized foam.
Figure 57:
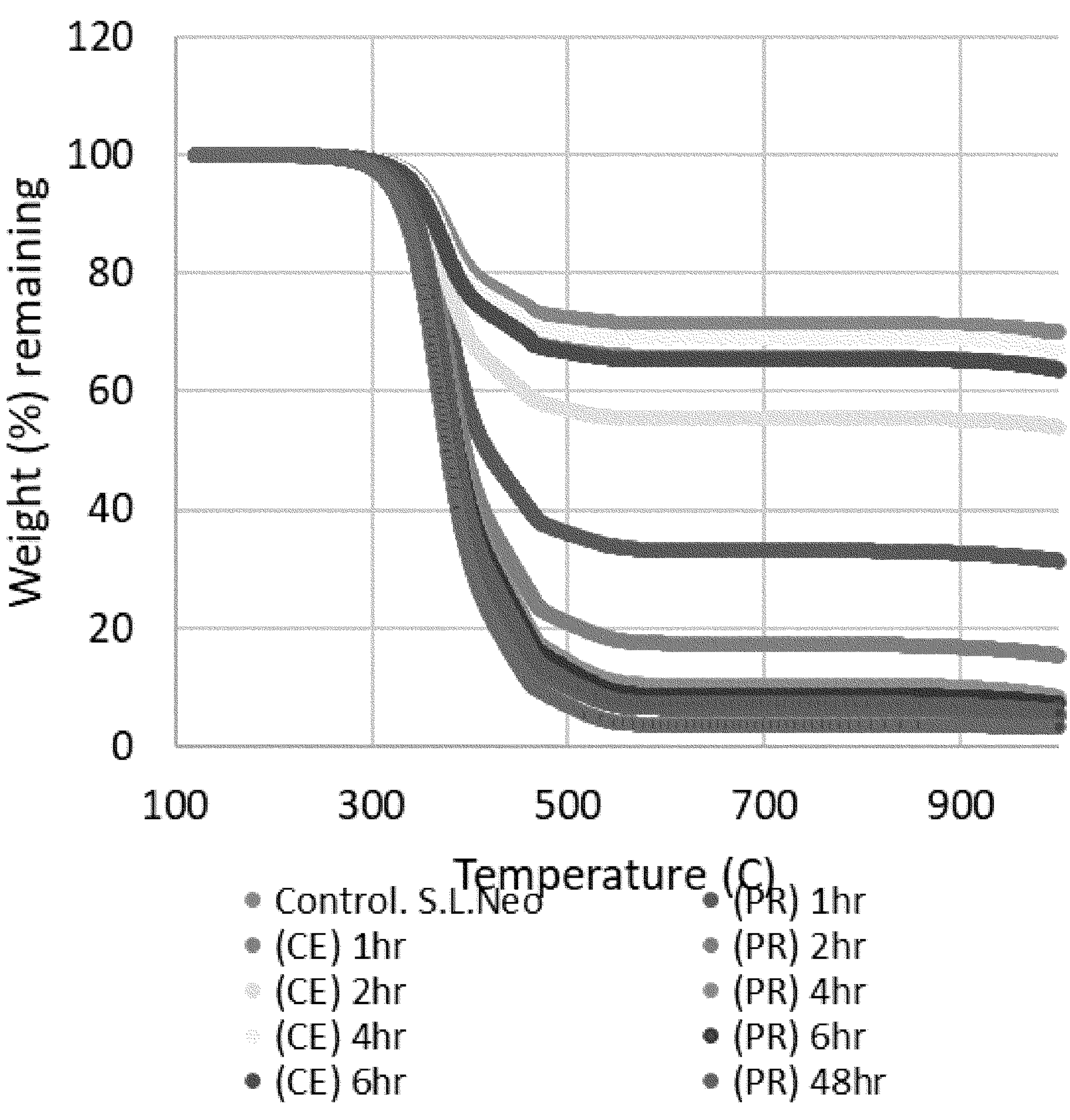
FIG. 57 shows a representative thermogravimetric analysis of a foam according to an embodiment of the invention formed using BADGE.

FIG. 56 shows glass transition temperatures of the foams as a function of Neopentyl monomer concentration (constant stoichiometric balance with PETMP) in both dry and plasticized (wet) foams. Representative TGA gravimetric analysis of BADGE, shown in FIG. 57, and NEO, shown in FIG. 58, foams as a function of cleaning time, demonstrating the removal of salt template from the material over 120 hr.

Figure 60:
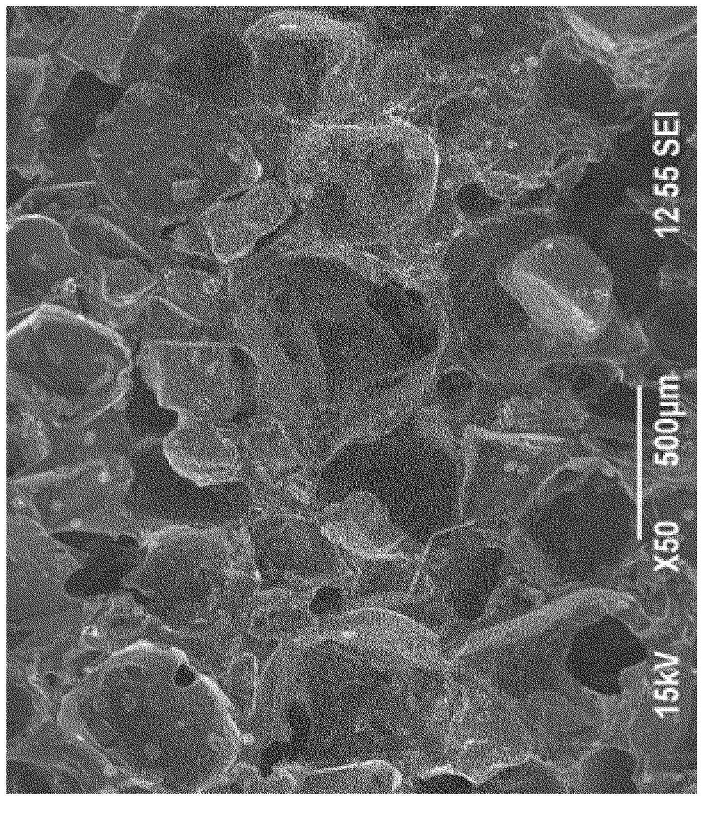
FIG. 60 shows a representative SEM image of a β-hydroxythioether network after a salttemplate has been removed.
Figure 59:
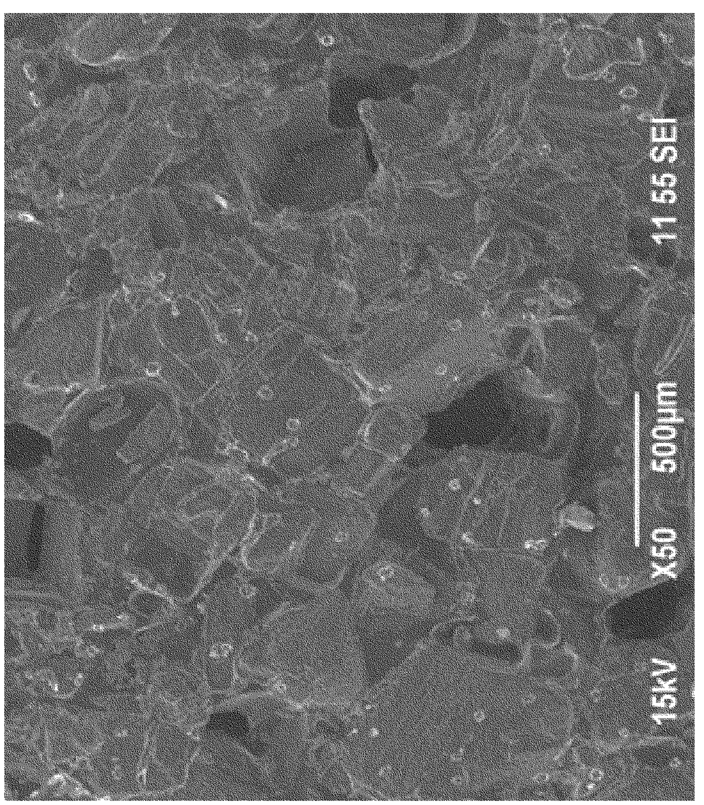
FIG. 59 shows a representative SEM image of a salttemplate with a β-hydroxythioether network.
Figure 62:
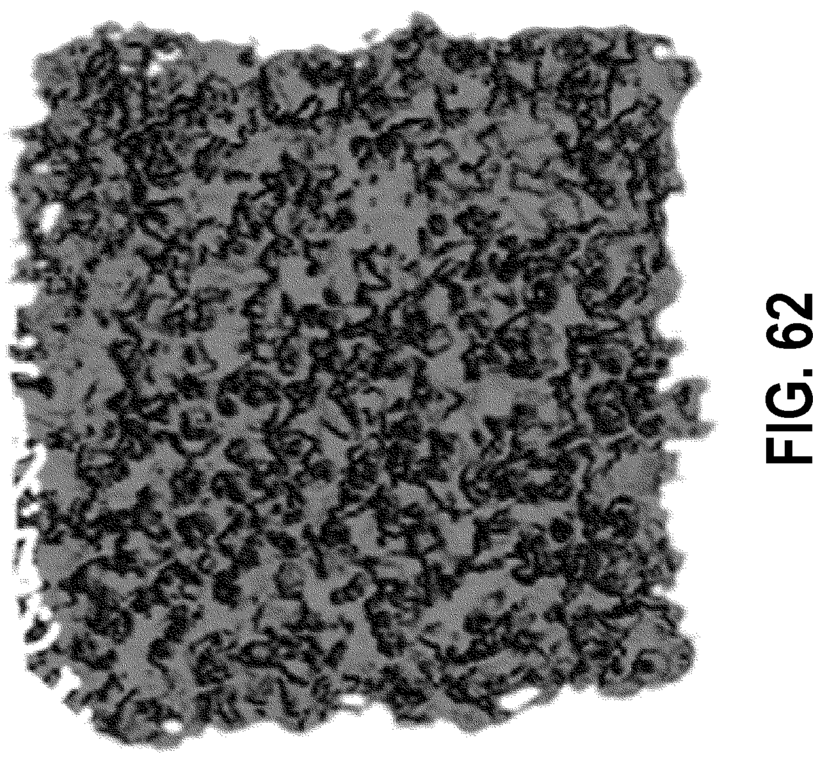
FIG. 62 shows a MicroCT reassembled structure of foam formed according to an embodiment of the present invention with NEO.
Figure 61:
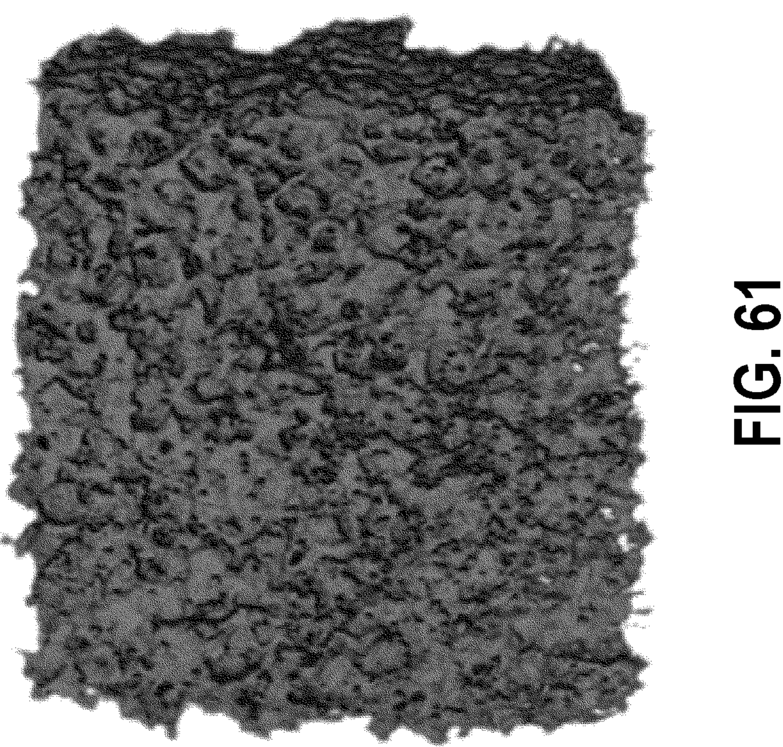
FIG. 61 shows a MicroCT reassembled structure of foam formed according to an embodiment of the present invention with BADGE.

FIG. 59 shows a representative SEM image of the salt template with p-hydroxythioethers network surrounding the particles and the resultant foam after template removal with water is shown in FIG. 60. MicroCT reassembled structures of the BADGE, shown in FIG. 61, and NEO, shown in FIG. 62, foams correspond with the SEM images. Cytocompatibility testing was performed on the foams using macrophages over 7 and 30 day periods (FIG. 4). 2D and 3D scaffold constructs were tested, both displaying excellent cytocompatibility over this period. Importantly, the macrophages were shown to grow without problem for 30 days on the surface of the foams, infiltrating the materials.

Figure 63C:
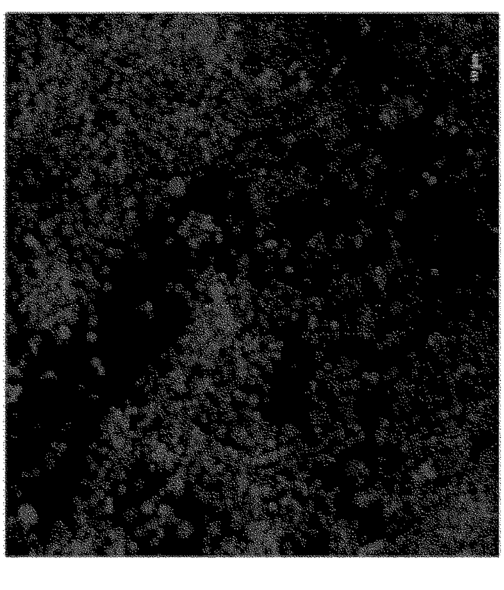
FIG. 63C shows a representative fluorescence microscopy image of a 2D surface of a foam formed according to an embodiment of the present invention with NEO.
Figure 63B:
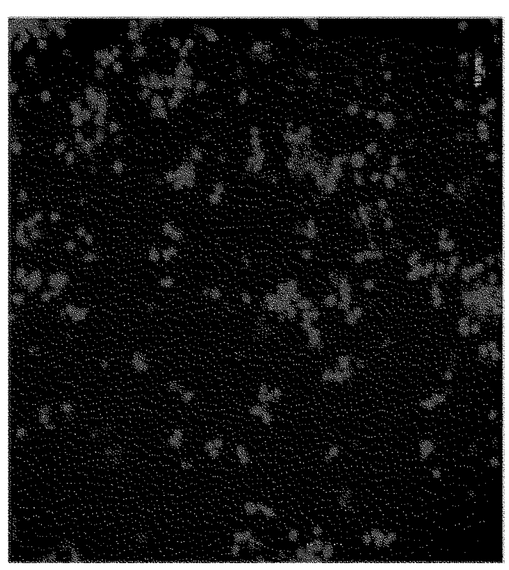
FIG. 63B shows a representative fluorescence microscopy image of a 2D surface of a foam formed according to an embodiment of the present invention with BADGE.
Figure 63A:
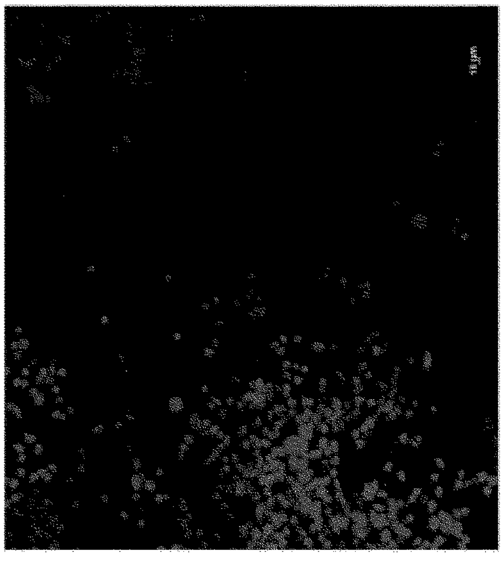
FIG. 63A shows a representative fluorescence microscopy image of a 2D surface of a control foam.
Figure 64:
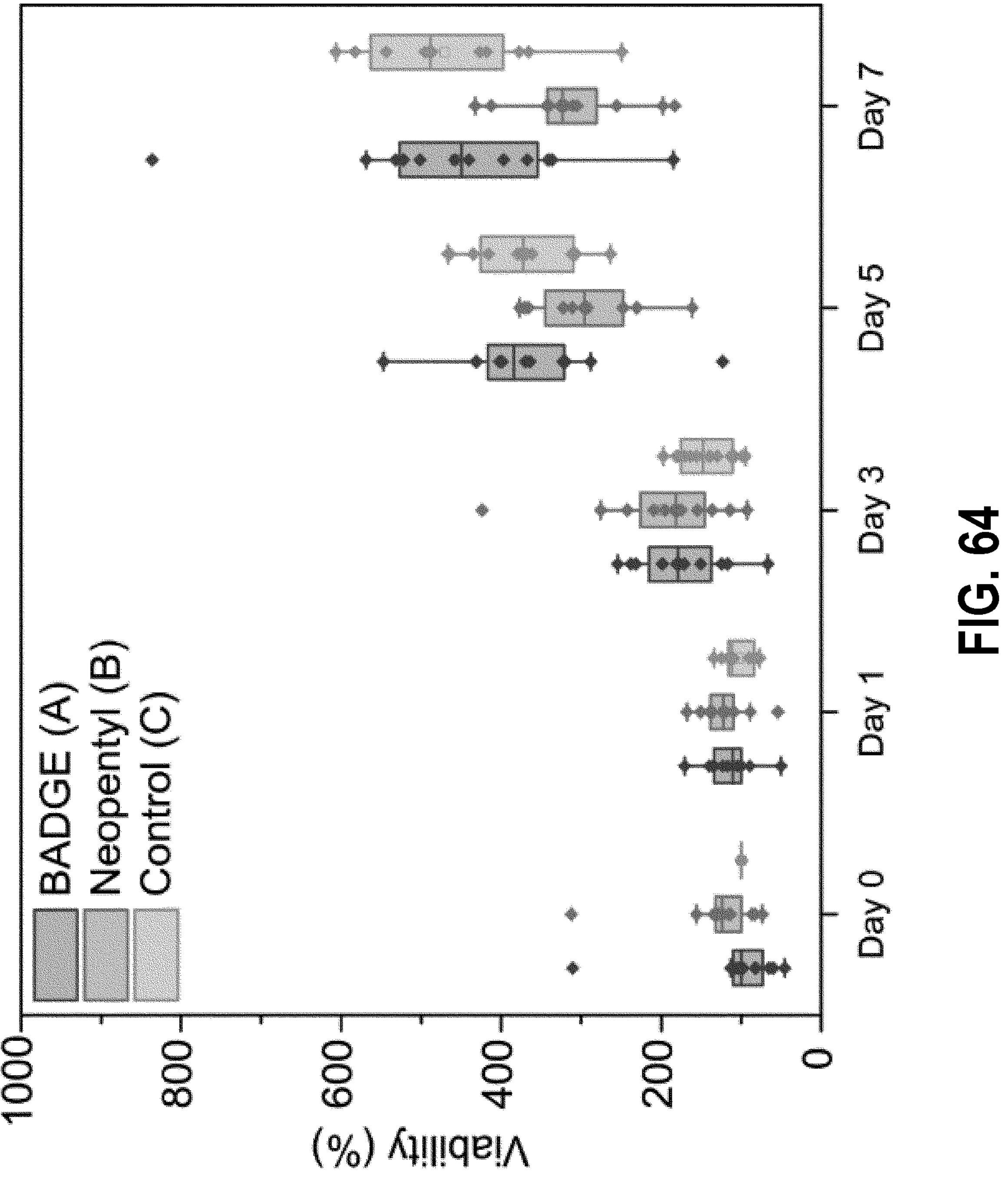
FIG. 64 is a plot of foam cell viability versus time of the representative foams shown in FIGS. 63A-63C.
Figure 65:
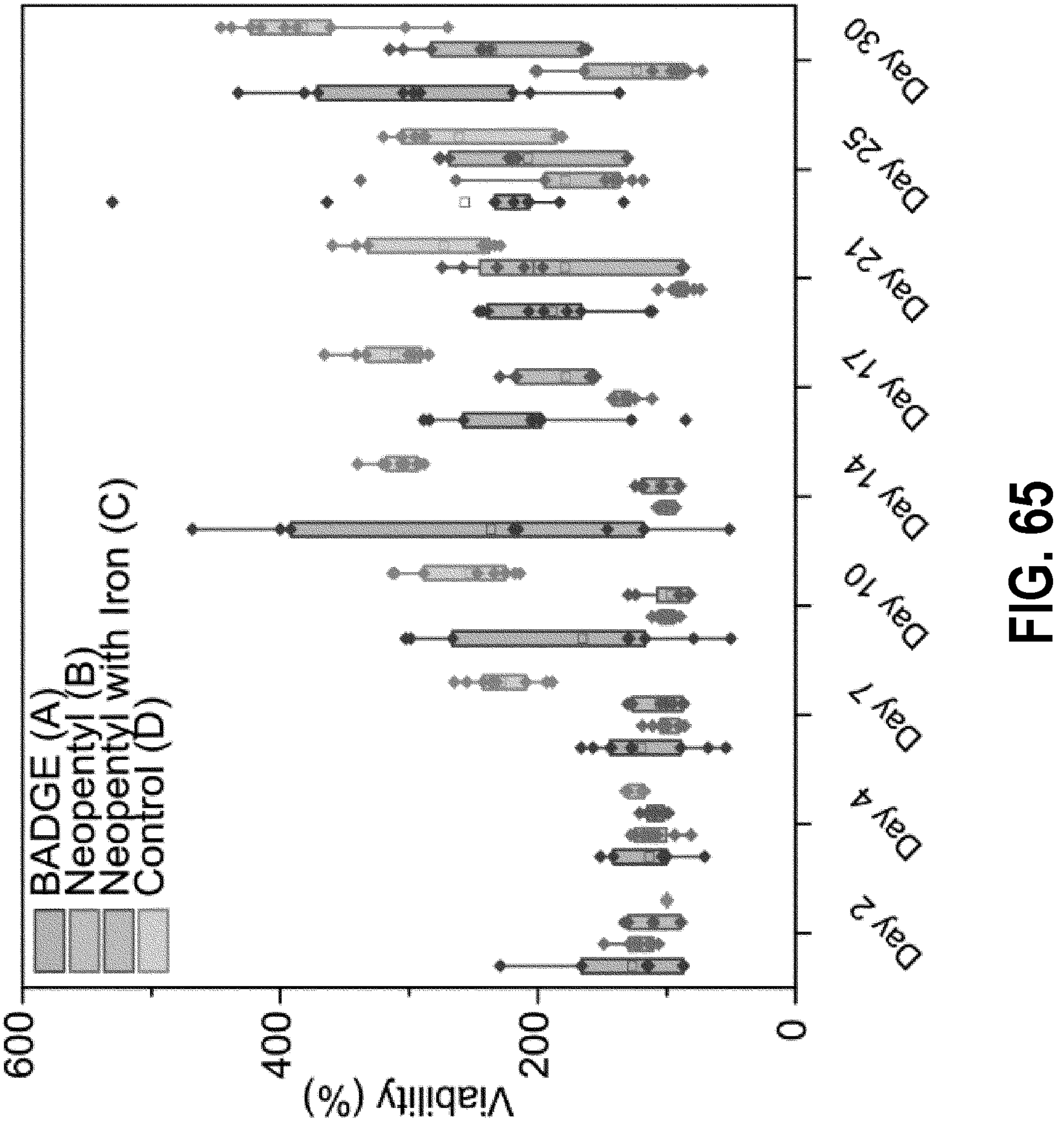
FIG. 65 is a plot of foam cell viability versus time of the representative foams shown in FIGS. 66A-66D.
Figures 66A, 66B, 66C, 66D:
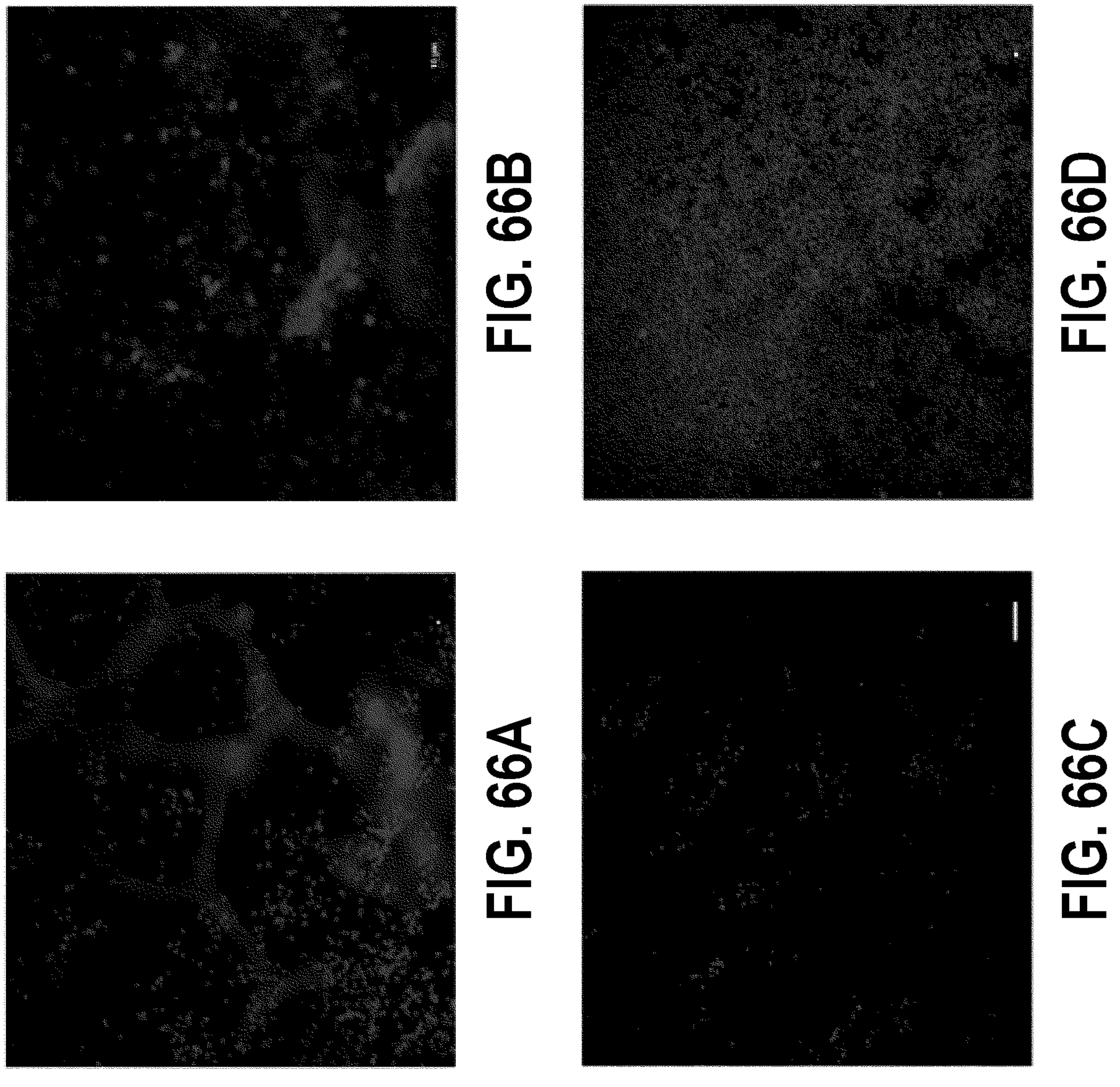
FIG. 66A shows a representative fluorescence microscopy image of a 3D surface of a foam formed according a control foam.
FIG. 66B shows a representative fluorescence microscopy image of a 3D surface of a foam formed according to an embodiment of the present invention with BADGE.
FIG. 66C shows a representative fluorescence microscopy image of a 3D surface of a foam formed according to an embodiment of the present invention with NEO.
FIG. 66D shows a representative fluorescence microscopy image of a 3D surface of a foam formed according to an embodiment of the present invention with NEO composited with 10 wt % $FeO_2$ nanoparticle additives.

FIGS. 63A-C show representative fluorescence microscopy images of the 2D surfaces. Particularly, FIG. 63A displays the control foam network, FIG. 63B displays the BADGE foam network, and FIG. 63C displays the NEO foam network films at day 7. A corresponding cell viability as measured by metabolic assay for the same time period is shown in FIG. 64. FIG. 65 is a graph of a 30-day analysis that was conducted using 3D foams compared with the same 2D glass slide control, again accompanied by representative fluorescence images at 30 days, shown in FIGS. 66A-D. Particularly, FIG. 66A displays the control foam network, FIG. 66B displays the BADGE foam network, FIG. 66C displays the NEO foam network, and FIG. 66D displays a composited NEO (10% $FeO_2$ nanoparticle additives) foam network.

The embodiments of the present invention recited herein are intended to be merely exemplary and those skilled in the art will be able to make numerous variations and modifications to it without departing from the spirit of the present invention. Notwithstanding the above, certain variations and modifications, while producing less than optimal results, may still produce satisfactory results. All such variations and modifications are intended to be within the scope of the present invention as defined by the claims appended hereto.

What is claimed is:

1. A method of making a shape memory polymer foam, the method comprising:

reacting an epoxide with a thiol monomer in the presence of an organobase to form the shape memory polymer foam;

wherein the reacting the epoxide with the thiol monomer is further in the presence of acetone.

2. The method of claim 1, wherein the organobase comprises 1,8-diazabicyclo[5.4.0]undec-7-ene.

3. The method of claim 1, wherein the thiol monomers comprise pentaerythritoltetra(3-mercaptopropionate).

4. The method of claim 1, wherein the epoxide comprises bisphenol A diglycidyl ether.

5. The method of claim 1, wherein the shape memory polymer foam comprises poly(β-thioether).

6. A method of making a shape memory polymer foam, the method comprising:

reacting an epoxide with a thiol monomer in the presence of an organobase, a salt, and acetone to form a shape memory polymer foam-salt composite removing at least a portion of the salt from the shape memory the shape memory polymer foam-salt composite to form the shape memory polymer foam.

7. The method of claim 6, wherein removing at least the portion of the salt is done by washing the shape memory polymer foam-salt composite.

8. The method of claim 6, wherein the epoxide is selected from a group consisting of bisphenol A diglycidyl ether (BADGE), BADGE derivatives, neopentyl monomer (NEO), NEO derivatives, N epoxide, Isophorone di(oxiran-2-methyl carbamate) (IDPI) epoxide, IDPI epoxide derivatives, and combinations thereof.

9. A method of making a shape memory polymer foam, the method comprising:

reacting pentaerythritoltetra(3-mercaptopropionate) and bisphenol A diglycidyl ether in the presence of 1,8-diazabicyclo[5.4.0]undec-7-ene to form a filament;

printing the filament into a form using a 3-D printer.

10. A method of making a shape memory polymer foam, the method comprising:

reacting an epoxide with a thiol monomer in the presence of an organobase to form the shape memory polymer foam;

wherein the organobase comprises 1,8-diazabicyclo[5.4.0]undec-7-ene.

11. The method of claim 10, wherein the thiol monomers comprise pentaerythritoltetra(3-mercaptopropionate).

12. The method of claim 10, wherein the epoxide comprises bisphenol A diglycidyl ether.

13. The method of claim 10, wherein the shape memory polymer foam comprises poly(β-thioether).

14. The method of claim 10, wherein the reacting the epoxide with the thiol monomer is further in the presence of acetone.

* * * * *